US012779170B2

(12) United States Patent
Beach

(10) Patent No.: US 12,779,170 B2
(45) Date of Patent: Nov. 3, 2026

(54) INTRAVASCULAR LITHOTRIPSY CATHETER

(71) Applicant: COVELLUS LLC, Belmar, NJ (US)

(72) Inventor: Bradley Beach, Belmar, NJ (US)

(73) Assignee: COVELLUS LLC, Lexington, KY (US)

( * ) Notice: Subject to any disclaimer, the term of this patent is extended or adjusted under 35 U.S.C. 154(b) by 453 days.

(21) Appl. No.: 18/241,720

(22) Filed: Sep. 1, 2023

(65) Prior Publication Data

US 2023/0405268 A1 Dec. 21, 2023

Related U.S. Application Data

(63) Continuation-in-part of application No. 18/144,208, filed on May 7, 2023, now abandoned, which is a (Continued)

(51) Int. Cl.
*A61M 25/00* (2006.01)

(52) U.S. Cl.
CPC ..... *A61M 25/0029* (2013.01); *A61M 2210/12* (2013.01)

(58) Field of Classification Search
CPC .................... A61B 2017/22007–22008; A61B 2017/22025; A61B 2017/22039;

(Continued)

(56) References Cited

U.S. PATENT DOCUMENTS 4,068,660 A 1/1978 Beck
4,123,091 A 10/1978 Cosentino (Continued)

FOREIGN PATENT DOCUMENTS

AU 2022259717 B2 12/2024
CA 3190813 A1 2/2022

(Continued)

OTHER PUBLICATIONS

Canadian Intellectual Property Office, Office Action of Nov. 29, 2022 and Search Report, Canadian Patent Application No. 2,990,676.

(Continued)

*Primary Examiner* — Brigid K Byrd
(74) *Attorney, Agent, or Firm* — Campbell IP Law LLC

(57) ABSTRACT

A medical device catheter comprises a first tube comprising a first cavitation solution lumen having a distal opening; and a second tube housing the first tube and comprising a cavitation bubble chamber, a second cavitation solution lumen in fluid communication with the first cavitation solution lumen through the distal opening, and a distal plug at a distal end of the cavitation bubble chamber to create a distal boundary of the cavitation bubble chamber. A proximal rapid exchange guidewire exit is positioned distal to the distal boundary of the cavitation bubble chamber and in communication with a guidewire lumen; and a first powered electrode extends through the first tube and the first cavitation solution lumen and cavitation bubble chamber and into the distal plug beyond the distal boundary of the cavitation bubble chamber.

20 Claims, 30 Drawing Sheets

Related U.S. Application Data continuation-in-part of application No. 18/095,992, filed on Jan. 11, 2023, now abandoned.

(60) Provisional application No. 63/298,282, filed on Jan. 11, 2022.

(58) Field of Classification Search
CPC .... A61B 2017/22021; A61B 17/22022; A61B 17/2202; A61B 17/22004
See application file for complete search history.

(56) References Cited

U.S. PATENT DOCUMENTS

| | | | | |
|---|---|---|---|---|
| 4,634,432 | A | 1/1987 | Kocak | |
| 4,932,419 | A | 6/1990 | de Toledo | |
| 4,955,862 | A | 9/1990 | Sepetka | |
| 5,057,092 | A | 10/1991 | Webster, Jr. | |
| 5,256,150 | A | 10/1993 | Quiachon | |
| 5,265,150 | A | 11/1993 | Helmkamp | |
| 5,458,652 | A | 10/1995 | Uebelacker | |
| 5,571,073 | A | 11/1996 | Castillo | |
| 5,706,827 | A * | 1/1998 | Ehr | A61M 25/09 600/585 |
| 5,788,653 | A | 8/1998 | Lorenzo | |
| 5,830,189 | A | 11/1998 | Chang | |
| 6,036,661 | A | 3/2000 | Schwarze | |
| 6,080,119 | A | 6/2000 | Schwarze | |
| 6,113,560 | A | 9/2000 | Simnacher | |
| 6,117,106 | A | 9/2000 | Wasicek | |
| 6,176,839 | B1 | 1/2001 | Michael | |
| 6,186,963 | B1 | 2/2001 | Schwarze | |
| 6,241,710 | B1 | 6/2001 | Vantassel | |
| 6,368,292 | B1 | 4/2002 | Ogden | |
| 6,390,995 | B1 | 5/2002 | Ogden | |
| 6,547,766 | B1 | 4/2003 | Fitz | |
| 6,613,062 | B1 | 9/2003 | Leckrone | |
| 6,666,834 | B2 | 12/2003 | Restle | |
| 6,849,994 | B1 | 2/2005 | White | |
| 6,972,116 | B2 | 12/2005 | Brill | |
| 7,229,431 | B2 | 6/2007 | Houser | |
| 7,976,557 | B2 | 7/2011 | Kunis | |
| 7,985,189 | B1 | 7/2011 | Ogden | |
| 8,092,401 | B2 | 1/2012 | Schultheiss | |
| 8,100,884 | B2 | 1/2012 | Schweikert | |
| 8,523,840 | B2 | 9/2013 | Powers | |
| 8,690,859 | B2 | 4/2014 | Drake | |
| 8,888,788 | B2 | 11/2014 | Hakala | |
| 8,905,998 | B2 | 12/2014 | Stephens | |
| 9,072,534 | B2 | 7/2015 | Hawkins | |
| 9,138,249 | B2 | 9/2015 | Adams | |
| 9,174,008 | B1 | 11/2015 | Kramer | |
| 9,180,280 | B2 | 11/2015 | Hawkins | |
| 9,204,928 | B2 | 12/2015 | Erdman | |
| 9,237,984 | B2 | 1/2016 | Hawkins | |
| 9,282,991 | B2 | 3/2016 | Schur | |
| 9,522,011 | B2 | 12/2016 | Cioanta | |
| 9,550,046 | B1 | 1/2017 | Allen | |
| 9,808,276 | B2 | 11/2017 | Silvestro | |
| 9,867,629 | B2 | 1/2018 | Hawkins | |
| 10,357,264 | B2 | 7/2019 | Kat-Kuoy | |
| 10,420,569 | B2 | 9/2019 | Adams | |
| 10,478,202 | B2 | 11/2019 | Adams | |
| 10,561,428 | B2 | 2/2020 | Eggert | |
| 10,702,293 | B2 | 7/2020 | Adams | |
| 10,765,440 | B2 | 9/2020 | Tozzi | |
| 10,814,120 | B2 | 10/2020 | Beach | |
| 10,856,893 | B2 | 12/2020 | Eggert | |
| 10,898,213 | B2 | 1/2021 | Grace | |
| 10,912,922 | B2 | 2/2021 | Beach | |
| 11,020,135 | B1 * | 6/2021 | Hawkins | A61M 25/104 |
| 11,026,707 | B2 | 6/2021 | Ku | |
| 11,439,459 | B2 | 9/2022 | Ko | |
| 11,478,261 | B2 | 10/2022 | Nguyen | |
| 11,517,338 | B2 | 12/2022 | Hawkins | |
| 11,633,200 | B2 | 4/2023 | Anderson | |
| 11,672,585 | B2 | 6/2023 | Schultheis | |
| 11,707,289 | B2 | 7/2023 | McCaffrey | |
| 11,766,271 | B2 | 9/2023 | Adams | |
| 11,771,449 | B2 | 10/2023 | Adams | |
| 11,826,067 | B2 | 11/2023 | Ju | |
| 11,896,248 | B2 | 2/2024 | Batchelder | |
| 11,911,056 | B2 | 2/2024 | Anderson | |
| 11,918,285 | B2 | 3/2024 | Sun | |
| 12,011,185 | B2 | 6/2024 | Vo | |
| 12,035,932 | B1 | 7/2024 | Nunes | |
| 12,064,129 | B2 | 8/2024 | Nguyen | |
| 12,096,950 | B2 | 9/2024 | Hakala | |
| 12,102,342 | B2 | 10/2024 | Hawkins | |
| 12,102,384 | B2 | 10/2024 | Cook | |
| 12,114,874 | B2 | 10/2024 | Nguyen | |
| 12,144,516 | B2 | 11/2024 | Betelia | |
| 12,156,668 | B2 | 12/2024 | Anderson | |
| 2001/0044633 | A1 | 11/2001 | Klint | |
| 2002/0095102 | A1 | 7/2002 | Winters | |
| 2003/0078562 | A1 | 4/2003 | Makower | |
| 2003/0125727 | A1 | 7/2003 | Truckai | |
| 2003/0130599 | A1 | 7/2003 | Restle | |
| 2003/0195428 | A1 | 10/2003 | Brockway | |
| 2004/0082879 | A1 | 4/2004 | Klint | |
| 2004/0181207 | A1 | 9/2004 | Vitullo | |
| 2004/0260271 | A1 | 12/2004 | Huyser | |
| 2005/0061697 | A1 | 3/2005 | Moberg | |
| 2005/0075588 | A1 | 4/2005 | Simnacher | |
| 2005/0080411 | A1 | 4/2005 | Ouchi | |
| 2005/0261664 | A1 | 11/2005 | Rome | |
| 2005/0274384 | A1 | 12/2005 | Tran | |
| 2006/0004286 | A1 | 1/2006 | Chang | |
| 2006/0074398 | A1 | 4/2006 | Whiting | |
| 2006/0253183 | A1 | 11/2006 | Thagalingam | |
| 2006/0259005 | A1 | 11/2006 | Konstantino | |
| 2007/0049960 | A1 | 3/2007 | Stephens | |
| 2007/0244440 | A1 | 10/2007 | Pal | |
| 2008/0033323 | A1 | 2/2008 | Meirer | |
| 2008/0097251 | A1 | 4/2008 | Babaev | |
| 2008/0183251 | A1 | 7/2008 | Azar | |
| 2008/0275427 | A1 | 11/2008 | Sage | |
| 2009/0163915 | A1 | 6/2009 | Potter | |
| 2010/0016862 | A1 | 1/2010 | Hawkins | |
| 2011/0127767 | A1 | 6/2011 | Wicks | |
| 2011/0275894 | A1 | 11/2011 | Mackin | |
| 2012/0116289 | A1 | 5/2012 | Hawkins | |
| 2012/0203255 | A1 | 8/2012 | Hawkins | |
| 2013/0030431 | A1 | 1/2013 | Adams | |
| 2013/0046296 | A1 | 2/2013 | Laufer | |
| 2013/0184654 | A1 | 7/2013 | Drake | |
| 2014/0094688 | A1 | 4/2014 | Tegg | |
| 2014/0191501 | A1 | 7/2014 | Brugger | |
| 2014/0276757 | A1 | 9/2014 | Ellman | |
| 2015/0007650 | A1 | 1/2015 | Rose | |
| 2015/0105771 | A1 | 4/2015 | Sim | |
| 2015/0173782 | A1 | 6/2015 | Garrison | |
| 2015/0283372 | A1 | 10/2015 | Maritan | |
| 2016/0135828 | A1 | 5/2016 | Hawkins | |
| 2017/0001000 | A1 * | 1/2017 | Beach | A61M 39/105 |
| 2017/0119428 | A1 | 5/2017 | Boyle | |
| 2018/0304053 | A1 | 10/2018 | Eggert | |
| 2018/0360482 | A1 | 12/2018 | Nguyen | |
| 2019/0029703 | A1 * | 1/2019 | Wasdyke | A61B 17/22022 |
| 2020/0171295 | A1 | 6/2020 | Beach | |
| 2020/0383724 | A1 | 12/2020 | Adams | |
| 2021/0220047 | A1 | 7/2021 | Curran | |
| 2021/0220052 | A1 | 7/2021 | Cook | |
| 2021/0267685 | A1 | 9/2021 | Schultheis | |
| 2021/0307828 | A1 | 10/2021 | Schultheis | |
| 2021/0378743 | A1 | 12/2021 | Massimini | |
| 2022/0071704 | A1 | 3/2022 | Le | |
| 2022/0125453 | A1 | 4/2022 | Nguyen | |
| 2022/0152364 | A1 | 5/2022 | Cope | |
| 2022/0183708 | A1 | 6/2022 | Phan | |
| 2022/0183738 | A1 | 6/2022 | Flores | |
| 2022/0273324 | A1 | 9/2022 | Schultheis | |
| 2022/0287730 | A1 | 9/2022 | Chisena | |
| 2022/0313359 | A1 | 10/2022 | Schultheis | |

(56) References Cited

U.S. PATENT DOCUMENTS

| | | | | |
|---|---|---|---|---|
| 2023/0038388 | A1 | 2/2023 | Batchelder | |
| 2023/0038663 | A1 | 2/2023 | Batchelder | |
| 2023/0040190 | A1 | 2/2023 | Batchelder | |
| 2023/0040420 | A1 | 2/2023 | Batchelder | |
| 2023/0041407 | A1 | 2/2023 | Batchelder | |
| 2023/0043475 | A1 | 2/2023 | Adams | |
| 2023/0044926 | A1 | 2/2023 | Batchelder | |
| 2023/0218309 | A1 | 7/2023 | Beach | |
| 2023/0255635 | A1 | 8/2023 | Schultheis | |
| 2023/0270459 | A1 | 8/2023 | Bradley | |
| 2023/0310054 | A1 | 10/2023 | Schultheis | |
| 2023/0338089 | A1 | 10/2023 | Schultheis | |
| 2023/0380903 | A1 | 11/2023 | Chisena | |
| 2023/0381472 | A1 | 11/2023 | Chisena | |
| 2024/0138862 | A1 | 5/2024 | Beach | |
| 2024/0374269 | A1* | 11/2024 | Hoye | A61B 17/00234 |
| 2025/0176984 | A1 | 6/2025 | Hasenberg | |
| 2025/0235228 | A1 | 7/2025 | Beach | |

FOREIGN PATENT DOCUMENTS

| | | | |
|---|---|---|---|
| CN | 103282074 | A | 9/2013 |
| CN | 106620995 | A | 5/2017 |
| CN | 116867445 | A | 10/2023 |
| CN | 116940289 | A | 10/2023 |
| DE | 29723605 | U1 | 12/1998 |
| EP | 1467349 | A1 | 10/2004 |
| EP | 1727125 | A1 | 11/2006 |
| EP | 2879597 | B1 | 9/2016 |
| EP | 4134018 | A1 | 2/2023 |
| EP | 4051154 | B1 | 7/2023 |
| EP | 4259012 | A1 | 10/2023 |
| EP | 4034004 | B1 | 12/2023 |
| EP | 4117563 | B1 | 2/2024 |
| JP | H07527 | A | 1/1995 |
| JP | H08243169 | A | 9/1996 |
| JP | H1033681 | A | 2/1998 |
| JP | H10503673 | A | 4/1998 |
| WO | 2009045793 | A1 | 4/2009 |
| WO | 2015007650 | A1 | 1/2015 |
| WO | 2022125525 | A1 | 6/2022 |
| WO | 2022125807 | A1 | 6/2022 |
| WO | 2022187058 | A1 | 9/2022 |
| WO | 2023015047 | A1 | 2/2023 |
| WO | 2023059967 | A1 | 4/2023 |
| WO | 2023154327 | A1 | 8/2023 |
| WO | 2023211810 | A1 | 11/2023 |

OTHER PUBLICATIONS

Extended European Search Report of European Application No. 16818897.7 dated Jan. 24, 2019.

International Search Report and Written Opinion of PCT/US2020/0117149 dated May 7, 2020.

International Search Report and Written Opinion, Application No. PCT/US23/10626, dated Apr. 24, 2023, 9 pages.

International Search Report, PCT/US2016/040725, dated Sep. 16, 2016.

Machine Translated Office Action of Japanese Application No. 2017-568259 dated May 15, 2020.

Office Action (Notice of Allowance and Fees Due (PTOL-85)) dated May 28, 2026 for U.S. Appl. No. 18/411,005 (pp. 1-8).

International Search Report and Written Opinion issued in PCT/US2023/021286, dated Jul. 27, 2023 (pp. 1-8).

International Search Report and Written Opinion issued in PCT/US2023/031907, dated Jan. 23, 2024 (pp. 1-7).

International Search Report & Written Opinion issued in PCT/US2024/011308 dated Apr. 26, 2024 (pp. 1-9).

International Search Report and Written Opinion issued in PCT/US2025/024265 dated May 27, 2025 (pp. 1-10).

Japanese Office Action (including English translation) issued in JP2025540796 dated Apr. 23, 2026 (pp. 1-8).

* cited by examiner

Section CS2

Section CS1

Section CS4

Section CS3

Section CS5

Section CS7

Section CS6

Section CS8

Section CS9

Section CS11

Section CS12

Section CS13

Section CS13

Section CS14

INTRAVASCULAR LITHOTRIPSY CATHETER

CROSS REFERENCE TO RELATED APPLICATIONS

This application is a continuation-in part of U.S. application Ser. No. 18/144,208 filed on May 7, 2023, which is a continuation-in-part of U.S. application Ser. No. 18/095,992 filed on Jan. 11, 2023 (which claims the benefit of U.S. Provisional Application No. 63/298,282 filed on Jan. 11, 2022), the entire contents of these applications hereby incorporated by reference.

BACKGROUND

The present disclosure relates generally to a design of a medical device for use in the body, and more specifically to a catheter, such as an intravascular lithotripsy catheter.

Catheter type devices are typically long tubular structures with an inner lumen suitable for a guidewire used to navigate the vasculature, inject contrast or therapeutic materials, aspirate thrombus, or provide a means to deliver other devices or therapies to a target site within the vasculature or other body lumen. Catheter type devices are typically inserted through a small opening in the skin or another opening under visual guidance and tracked to the target location within the body. Catheters for minimally invasive procedures are typically one-piece, unitary constructions combining structural, therapeutic and diagnostic elements at the distal end of the catheter.

U.S. Patent Application Publication No. 2007/0244440 discloses a medical device including a catheter with an expandable tip for use with at least two different sizes of wire guides. The catheter includes a wire guide lumen sized to receive a first wire guide of a first diameter. The catheter may also include a tip lumen that extends in a distal direction from a first opening in communication with the wire guide lumen to a second opening. The first opening is sized to receive the first wire guide, and the second opening is sized to receive a second wire guide of a smaller diameter than the first wire guide. The catheter also includes one or more longitudinal expansion features capable of radially expanding the tip lumen to receive a wire guide of a diameter up to the first diameter through the second opening.

U.S. Pat. No. 8,100,884 discloses an adapter assembly for connecting a catheter assembly to a tunneler having a generally tubular body having a first end, a second end and a longitudinal axis extending there through between the first end and the second end. The first end of the adapter is constructed to engage the proximal end of a trocar. The second end of the adapter is constructed to releasably engage at least one catheter lumen. A slider is disposed about the adapter and is longitudinally slidable along the adapter. When the slider is slid towards the second end of the adapter, the slider engages a plurality of legs on the adapter and biases the plurality of legs toward each other and the longitudinal axis of the adapter.

U.S. Pat. No. 8,523,840 discloses coupler assemblies to be used with a catheter to connect a proximal end of the catheter to extracorporeal medical equipment. An exemplary coupler assembly includes a spherical linkage coupler for a catheter. The coupler comprises a first cylinder portion for connecting to a structure, and a second cylinder portion for connecting to a distal end of a body of the catheter. The coupler also comprises a spherical linkage including at least two link arms. Each of the two link arms are connected on one end to the first cylinder portion and on the other end to the second cylinder portion. The two link arms connect a portion of the structure to the distal end of the catheter and enable the structure to move relative to the distal end of the catheter in response to an external force exerted on the structure.

U.S. Pat. Nos. 9,282,991; 9,808,276; 7,976,557; and U.S. Publication No. 2006/0259005 describe variations of a method of delivering a therapeutic agent, such as a drug, using a cutting balloon wherein the cutting or scoring members may comprise the therapeutic agent coated thereon. The cutting or scoring members are integral with the construction of the balloon and catheter system itself.

U.S. Publication No. 2008/0275427 describes a catheter connection system to connect catheter tubes together to form a secure and leak resistant connection. As described the connection system includes a threaded connector inserted into an end of a catheter lumen where an inner portion of the catheter lumen is elastically compliant to conform to the threaded structure of the connector.

U.S. Pat. No. 8,956,371 describes a shockwave balloon catheter system that uses shockwaves generated inside the inflatable balloon of an angioplasty balloon catheter to aid in treating vascular lesions blocking blood vessels. The shockwave can aid in breaking up calcium deposits in these vascular lesions. Similar shockwave technology has been used in lithotripter medical devices to help break up kidney stones in the body, as described in U.S. Pat. No. 5,047,685, for example.

It is desirable to provide an improved adapter and modular system designed with features that expand, augment, or modify the configuration or intended use of a medical device or parent module, such as by providing lithotripsy functionality. The adapter including geometry, mechanical and/or thermal properties to expeditiously attach to the medical device, such as a catheter.

Alternatively, it is desirable to provide an improved catheter designed with useful features including lithotripsy functionality, for example, whether as part of a modular system or unitary design.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In one aspect, a medical device catheter comprises a cavitation bubble chamber configured to contain a cavitation solution, and at least two electrodes positioned within the cavitation bubble chamber to be in contact with the cavitation solution and to form an electrode gap. A proximal end of the medical device catheter is adapted to remain outside the body of the patient during use of the catheter, and a first lumen is in fluid communication with the cavitation bubble chamber and the proximal end, configured to deliver the cavitation solution from the proximal end of the medical device catheter to the cavitation bubble chamber. The at least two electrodes are configured to generate sparking or arcs across the electrodes which creates a shockwave and cavitation bubbles when powered by a high voltage pulse generator.

In another aspect, a medical device catheter comprises a first tube comprising a first cavitation solution lumen having a distal opening; and a second tube housing the first tube and comprising a cavitation bubble chamber, a second cavitation solution lumen in fluid communication with the first cavitation solution lumen through the distal opening, and a distal plug at a distal end of the cavitation bubble chamber to create a distal boundary of the cavitation bubble chamber. A proximal rapid exchange guidewire exit is positioned distal to the distal boundary of the cavitation bubble chamber and in communication with a guidewire lumen; and a first powered electrode extends through the first tube and the first cavitation solution lumen and cavitation bubble chamber and into the distal plug beyond the distal boundary of the cavitation bubble chamber.

DETAILED DESCRIPTION

Figure 1:
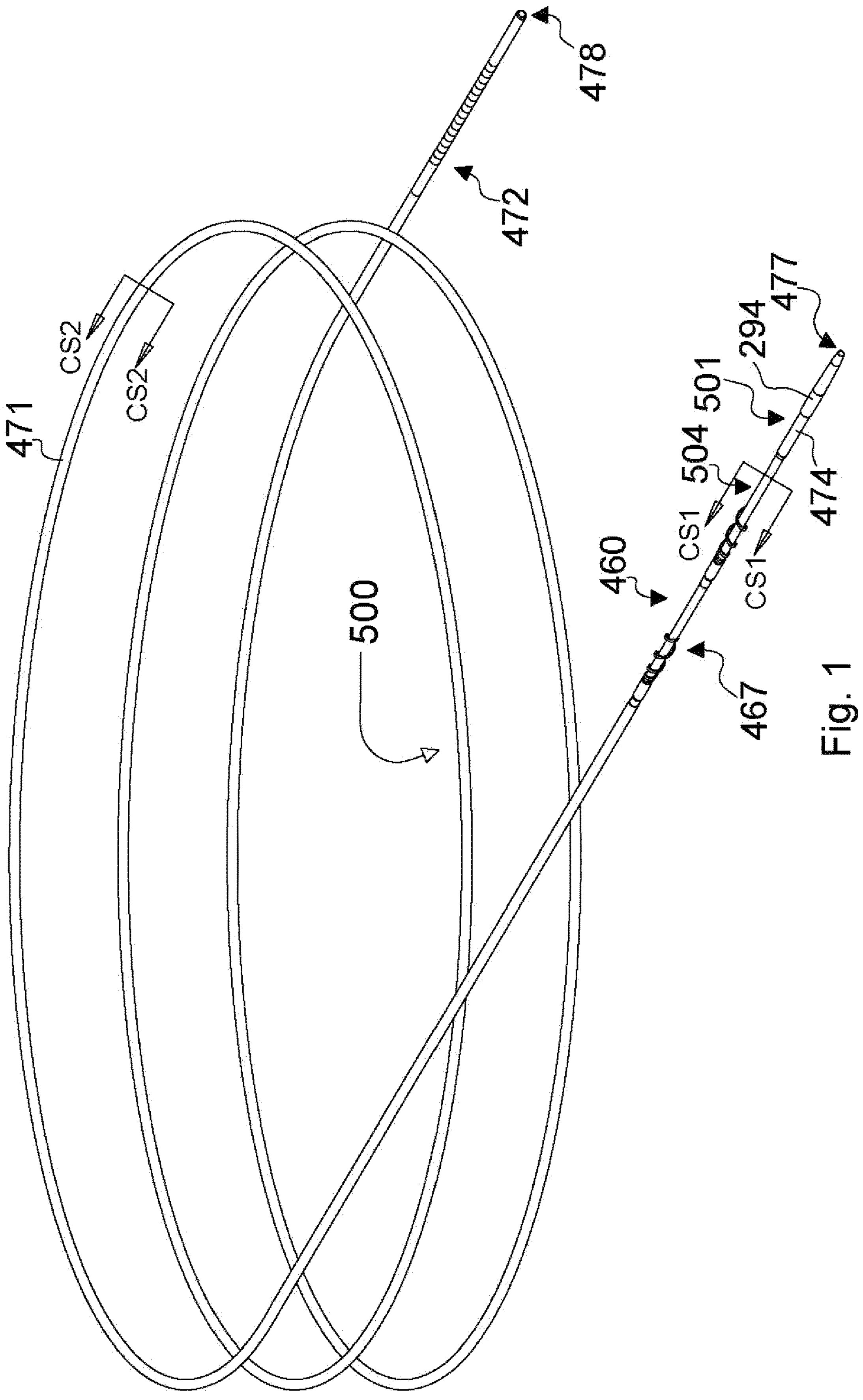
FIG. 1 is a schematic, perspective, view of an adapter according to the present disclosure.

In accordance with the present disclosure, in one aspect an adapter may be constructed to have a proximal portion that interfaces with a medical device or parent module and a distal portion that modifies, augments, or extends the configuration or intended use of the medical device. As an example, the medical device may be a catheter. The adapter or adapter module is also a medical device and can be thought of as an accessory to the parent module medical device, augmenting the performance or functionality. In another aspect, an attachment mechanism of the adapter may secure the adapter to the distal end of the medical device catheter during use. The distal portion of the adapter may extend distally from the distal end of the catheter and is designed with features that expand, augment, or modify the configuration or intended use of the medical device catheter, such as with lithotripsy functionality as described further herein.

The proximal portion of the adapter may be designed to couple, such as through an interference fit, with an internal lumen of the medical device such that during subsequent use the adapter remains securely attached. The proximal portion may be additionally designed to be easily inserted into the internal lumen of a medical device. The proximal portion of the adapter may include an attachment mechanism, more completely described below, that provides securement between the adapter and medical device. The adapter and medical device comprise two modules of a modular medical device catheter system. The attachment mechanism allows an adapter module and a medical device module, also referred to as the parent module, to be combined as required by the physician or physician's staff in the operating room during a medical procedure to create a modular medical device catheter system. Varying combinations of adapter modules, or adapters and parent modules or parents, allows multiple variants of a medical device catheter to be flexibly created according to the dynamic needs and challenges of each patient and procedure. The modular medical device catheter system according to the present disclosure provides the physician with the benefit of flexibility to construct a medical device catheter of their choosing, combining structural, therapeutic, and diagnostic elements at the distal end for a specific procedural need. It also provides the hospital with inventory benefits, i.e. more medical device catheter variants from fewer inventory items or modules.

The medical device or parent module typically has a proximal end that remains outside the body of the patient and a distal end that goes inside the body of the patient. Examples of parent modules include but are not limited to: balloon catheters, stent delivery system catheters, transcatheter replacement valves and associated delivery catheters, stent graft delivery catheters, dissection repair catheters, atherectomy catheters, ablation catheters, aspiration catheters, and thrombectomy catheters.

An example of a suitable modular catheter system for use with the present disclosure is described in U.S. Pat. No. 11,660,439B2 by the inventor, issued on May 30, 2023, and hereby incorporated by reference in its entirety.

If the adapter module of a modular medical device catheter system includes an internal lumen, additional adapter modules can be added using this internal lumen to further add features, creating an enhanced modular medical device catheter, such as a parent plus a plurality of adapters. The modular arrangement allows a parent and adapter combination to become a parent in a new parent and adapter combination.

The adapter may also include conductors to transmit electrical signals from outside the patient body to the distal end of the parent device. One application of this may be an adapter with a distal portion that includes electrodes powered or activated in a manner similar to an electrophysiology catheter. The conductor in electrophysiology catheters are sometimes fine scale copper magnet wire, e.g. 35 gauge, or other polymer coated wire conductors, and similar conductors could be used in an electrophysiology adapter. Conductors may be housed inside the central tube, electrically connecting the distal portion of the adapter to outside the patient. The tube, wire or mandrel could extend proximally all the way out the proximal end of the target catheter or device.

In another aspect of the present disclosure, a medical device catheter is provided having improved functionality, such as through the incorporation of lithotripsy elements and functionality as described further herein. The catheter may either be utilized as part of a modular catheter system as described, for example, with reference to FIGS. 1-28, or as a unitary catheter design as described, for example, with reference to FIGS. 29-54, among other relevant disclosures. In some embodiments, the unitary catheter may be a balloon catheter incorporating lithotripsy elements and functionality.

In another aspect, a medical device catheter may comprise a first tube comprising a first cavitation solution lumen having a distal opening; and a second tube housing the first tube and comprising a cavitation bubble chamber, a second cavitation solution lumen in fluid communication with the first cavitation solution lumen through the distal opening, and a distal plug at a distal end of the cavitation bubble chamber to create a distal boundary of the cavitation bubble chamber.

In another aspect, a proximal rapid exchange guidewire exit may be positioned distal to the distal boundary of the cavitation bubble chamber and in communication with a guidewire lumen.

In another aspect, a first powered electrode may extend through the first tube and the first cavitation solution lumen and cavitation bubble chamber and into the distal plug beyond the distal boundary of the cavitation bubble chamber.

In another aspect, a portion of the second tube may overlap a portion of the guidewire lumen.

In another aspect, a distal end of the second tube may comprise a distal edge that extends beyond a proximal edge of the second tube and the distal edge may overlap the portion of the guidewire lumen.

In another aspect, the first powered electrode may overlap a portion of the guidewire lumen.

In another aspect, the distal opening of the first cavitation solution lumen may be proximal to the distal boundary of the cavitation bubble chamber.

In another aspect, at least a portion of the second cavitation solution lumen may be disposed around the outside of the first tube.

In another aspect, at least a portion of the second tube may form the cavitation bubble chamber and at least a portion of the second cavitation solution lumen.

In another aspect, a distal end of the first tube may comprise a distal edge that extends beyond a proximal edge of the tube.

In another aspect, the first tube may be biased off-axis relative to the second tube.

In another aspect, the first powered electrode may be biased off-axis relative to the first tube or the second tube.

In another aspect, a portion of the second tube may be disposed between a portion of the first powered electrode and a portion of the guidewire lumen.

In another aspect, a portion of the first powered electrode may be disposed between a portion of the second tube and a portion of the guidewire lumen.

In another aspect, a second powered electrode may be disposed outside of the first tube.

In another aspect, at least one intermediate electrode may be disposed outside of the first tube to create a first electrode gap between the at least one intermediate electrode and the first powered electrode, and a second electrode gap between the at least one intermediate electrode and the second powered electrode.

In another aspect, the at least one intermediate electrode comprises a semi-circular cylinder.

In another aspect, the at least one intermediate electrode may be coaxial with the first cavitation solution lumen.

In another aspect, the first powered electrode does not comprise an insulative coating in the region of the cavitation bubble chamber.

In another aspect, a polymer jacket may form at least a portion of the second tube and the cavitation bubble chamber.

In another aspect, an inflatable balloon may be positioned proximal to the cavitation bubble chamber.

In another aspect, a portion of the guidewire lumen may comprise a third tube.

In another aspect, the second tube may comprise an elongated element of an IVL adapter for use with a modular medical device catheter system, including adapter features described with reference to FIGS. 1-28, for example. This includes but is not limited to elongated element 462 described further below in reference to the Figures.

The electrodes referenced throughout the present disclosure may be positioned or otherwise configured to create a shockwave and cavitation bubbles in a cavitation solution for intravascular lithotripsy therapies, for example. The positioning, operation and function of the electrodes will be apparent with reference to the figures and description provided further herein.

FIG. 1 is a schematic, perspective, view of an electrical adapter 500 according to an aspect of the present disclosure. Electrical adapter 500 includes a distal portion 501, which includes an electrical active element 294 and runway 474. Electrical adapter 500 includes a distal end 477 and a proximal end 478. Electrical adapter 500 includes a proximal portion 504 that incorporates an attachment mechanism 467 and elongate body 460. Electrical adapter 500 also includes a tubular extension 471 and electrical connector 472.

Figure 2:
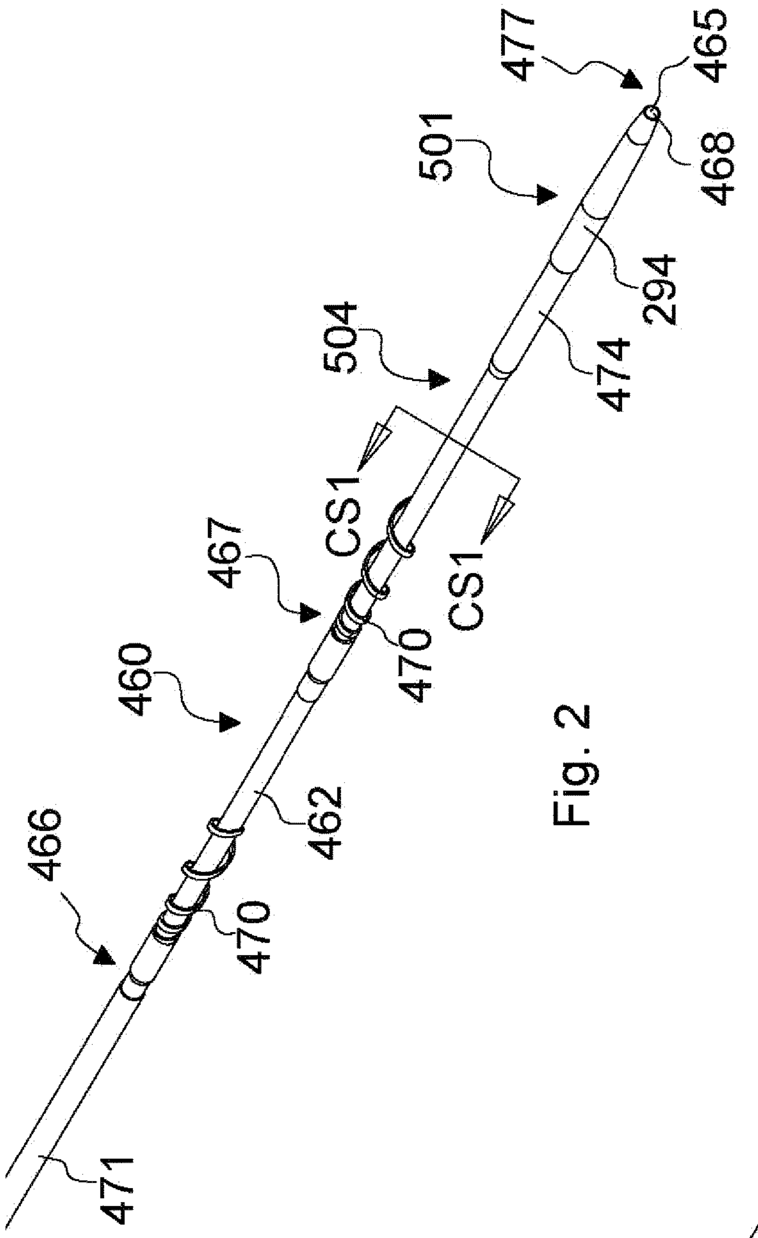
FIG. 2 is an enlarged detailed view of FIG. 1, showing part of a distal portion of the adapter, the attachment mechanism, and other features.

FIG. 2 is an enlarged detailed view of the proximal portion 504 of electrical adapter 500, distal portion 501 of electrical adapter 500, attachment mechanism 467, and elongate body 460. Attachment mechanism 467 includes elongated element or central tube 462 and interfacing elements 470. Elongate body 460 includes a tubular extension 471, extending from the proximal end 466 of central tube 462. The distal portion 501 includes a distal exit 468 for a central lumen 465 at the distal end 477 of the adapter 500.

Figure 3:
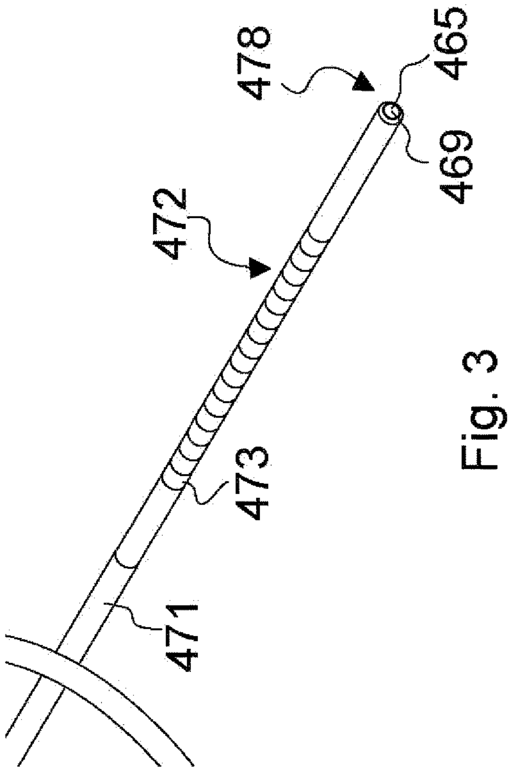
FIG. 3 is an enlarged detailed view of FIG. 1, showing a proximal end of the adapter, including the electrical connector.

FIG. 3 is an enlarged detailed view of the proximal end 478 of electrical adapter 500 showing a proximal exit 469 for a central lumen 465 at the proximal end 478 of adapter 500, tubular extension 471, and electrical connector 472 which includes ring electrical contacts 473.

Figure 4:
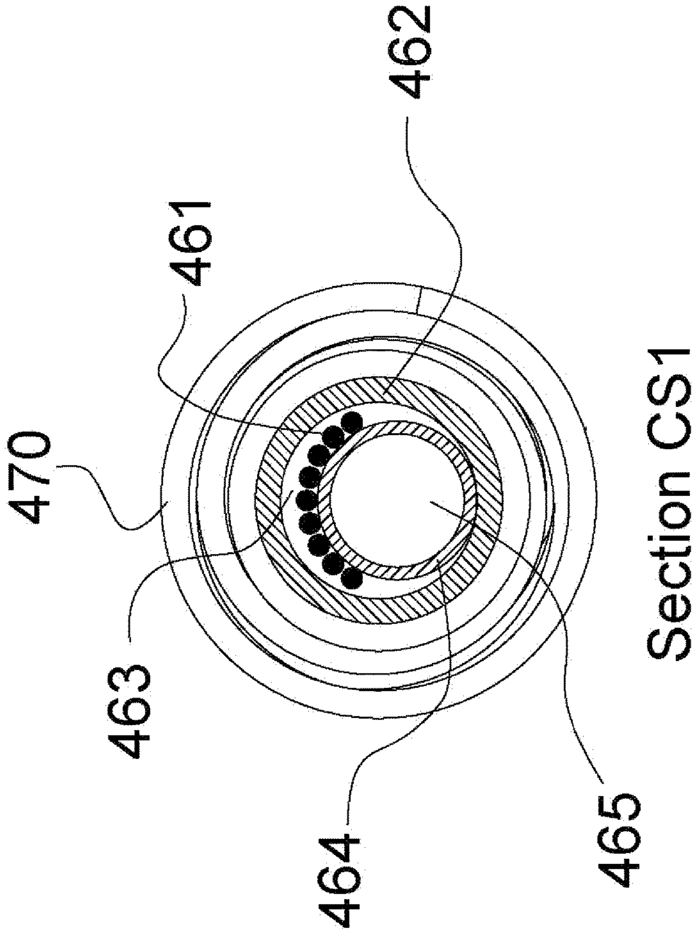
FIG. 4 is a partial schematic, transverse, cross-sectional view CS1 of the adapter of FIG. 1.

FIG. 4 is a partial schematic, transverse, cross-sectional view of electrical adapter 500 at CS1 as illustrated in FIG. 1 showing electrical conductors 461 and second central tube 464, that creates central lumen 465, within the lumen 463 of elongated element 462, as well as interfacing element 470 bonded to the outside of elongated element 462.

Figure 5:
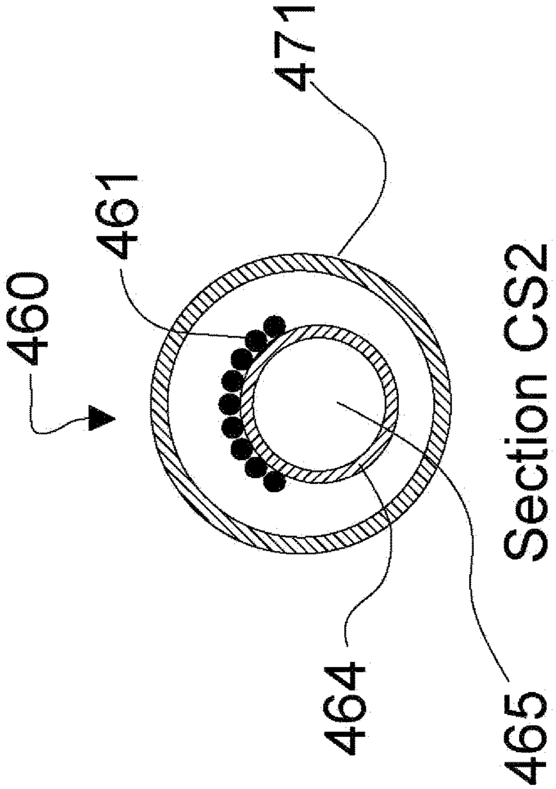
FIG. 5 is a partial schematic, transverse, cross-sectional view CS2 of the adapter of FIG. 1.

FIG. 5 is a partial schematic, transverse, cross-sectional view of electrical adapter 500 at CS2 as illustrated in FIG. 1 showing tubular extension 471 of the elongated body 460 which provides a lumen or conduit for both the electrical conductors 461 and second central tube 464, which creates a central lumen 465.

FIGS. 1-5 show electrical adapter 500, which includes a distal portion 501 that may comprise, for example, electrically active elements 294 such as intravascular ultrasound (IVUS) transducers, lithotripsy electrodes, pressure sensors, imaging sensors, thermocouples, ablation electrodes, and other features requiring electrical signal transmission or electrical power. Electrical adapter 500 may also include a proximal portion 504 that incorporates an attachment mechanism 467 and elongate body 460. The elongate body 460 of electrical adapter 500 includes electrical conductors 461, for example, to facilitate electrical communication between the electrical connector 472 and electrodes described further herein. In this configuration, the conductors 461 extend proximally from the distal portion 501 of adapter 500 through the lumen 463 of the central tube or elongated element 462 but outside the lumen 465 of a second central tube 464 within the central tube 462. The second central tube 464 may be used by a physician as a guidewire lumen using over the wire techniques after the electrical medical device catheter system 600 is assembled.

The second central tube 464 may also be omitted from the design, for example, if a guidewire lumen is not necessary, which may be the case for rapid exchange style configurations of the adapter 500. In the case where a central tube lumen 463 is not needed for a guidewire, the central tube lumen 463 could be used both as a passageway for conductors as well as an inflation lumen in alternate configurations of the distal portion 501 of the adapter 500, for example, where the adapter 500 includes a balloon to be inflated in-vivo. In either case, the second central tube 464 could extend proximal to or past the proximal end 219 of a medical device catheter 201 (shown in FIG. 6 and FIG. 7, for example). It may be advantageous for the proximal end 466 of central tube 462 to only extend far enough for the attachment mechanism 467 to incorporate compressible interfacing elements 470 to ensure secured coupling between the adapter 500 and a medical device catheter 201. The compressible interfacing elements 470 are designed to compress to interface with a lumen 211 at the distal end 213 of medical device catheter 201 to secure the electrical adapter 500 at the distal end 213 of medical device catheter 201. These compressible interfacing elements 470 are also described with reference to U.S. Pat. No. 11,660,439B2 by the inventor, referenced above and incorporated by reference in its entirety.

In an alternate embodiment, the proximal end 466 of central tube 462 could extend to a position proximal to a proximal end 219 of a medical device catheter 201. It may be advantageous when using the adapter 500 to have the conductors 461 bonded or attached to the outer surface of the second central tube 464. Alternatively heat shrink tubing, such as thin-walled polyester heat shrink tubing, could be used to hold the conductors 461 against the outer surface of the second central tube 462 in regions proximal to the proximal end 466 of central tube 462, creating a cohesive structure. Another alternative is to reflow a polymer jacket around the conductor 461 and second central tube 464 configurations in a manner similar to other catheter manufacturing techniques, such as guide catheter manufacturing. Another alternative is to incorporate a metallic or polymer spiral or coil around the length of the conductor 461, second central tube 464, and central tube 462 configuration in a manner similar to a conventional 0.035" guidewire and provide the buckling stability of a guidewire.

FIG. 4 is transverse cross-sectional view at location "CS1" of FIG. 1 and FIG. 2, illustrating an example of a nine (9) conductor 461 configuration. The electrical conductors 461 may comprise standard round 42 AWG magnet wire, for example. It can be appreciated that the configuration, geometry, and number of electrical conductors can be tailored to the requirements of the electrically active elements of the adapter 500.

FIG. 5 is a transverse cross-sectional view at location "CS2" of FIG. 1, illustrating elongate body 460 for adapter 500 which includes a tubular extension 471, extending from the proximal end 466 of central tube 462. Tubular extension 471 provides a conduit for both the electrical conductors 461 and second central tube 464.

The electrical conductors 461 can extend proximally from any electrically active elements 294 at distal portion 501 to a position proximal to the proximal end 219 of a medical device catheter 201, with or without central tube 462, second central tube 464, or tubular extension 471 also extending to a position proximal to the proximal end 219 of a medical device catheter 201.

In an alternate embodiment of electrical adapter 500, electrically active elements could be positioned proximal to the attachment mechanism 467 instead of at the distal portion 501.

As illustrated in FIGS. 1-5, the proximal end 478 of adapter 500 may comprise electrical connector 472 in electrical communication with the electrodes described further in the present disclosure. Connector 472 may comprise a ring electrical contact 473 for each conductor 461 used, for example, nine (9) ring electrical contacts 473 for each of the nine (9) electrical conductors 461. Second central tube 464 may include a distal exit 468 for lumen 465 at the distal end 477 of the adapter 500 and a proximal exit 469 at the proximal end 478 of adapter 500.

Figure 6A:
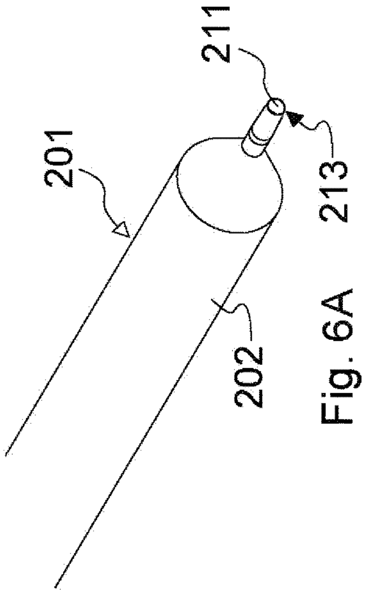
FIG. 6A is a partial schematic, perspective view of a balloon catheter parent before an adapter is attached to the distal end of the balloon catheter parent, and with the inflatable balloon represented as inflated for the purposes of illustration.

FIG. 6A is a partial schematic, perspective view of a balloon catheter or parent module 201, which is a medical device catheter, which includes a lumen 211 at the distal end 213, before electrical adapter 500 is attached to the distal end 213 of the balloon catheter 201, and with inflatable balloon 202 represented as inflated for the purposes of illustration.

Figure 6B:
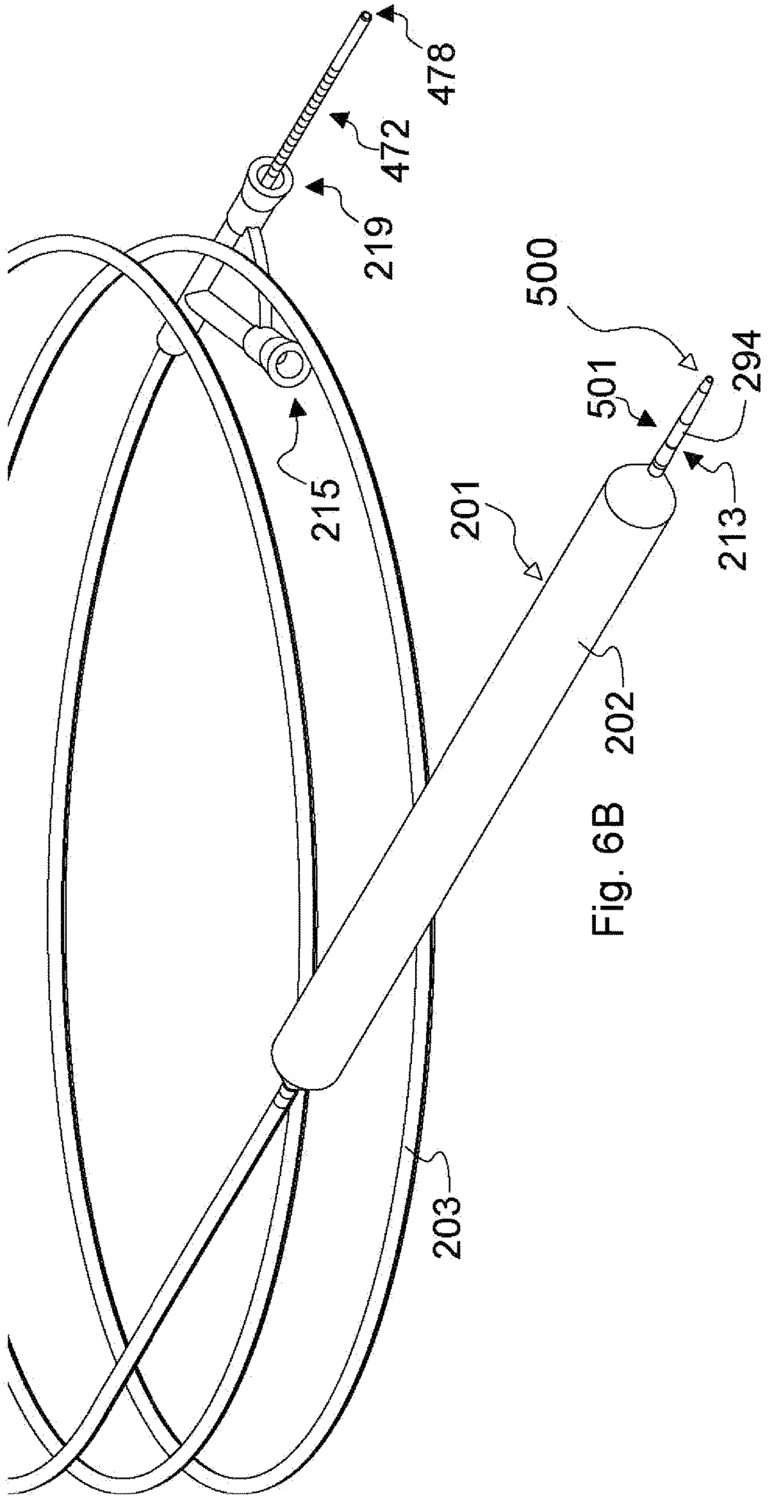
FIG. 6B is a partial schematic, perspective view of an adapter according to the present disclosure, attached to the distal end of a balloon catheter, and with the inflatable balloon represented as inflated for the purposes of illustration.

FIG. 6B is a partial schematic, perspective view of electrical adapter 500, according to an aspect of the present disclosure, attached to the distal end 213 of a balloon catheter 201, and with the inflatable balloon 202 represented as inflated for the purposes of illustration. As shown, the electrically active element 294 of distal portion 501 is distal to the distal end 213 of balloon catheter 201. The proximal end 478 of electrical adapter 500 and electrical connector 472 are proximal to the proximal end 219 of balloon catheter 201. Balloon catheter 201 includes a catheter shaft 203 to connect inflatable balloon 202 to a fitting assembly 215.

Figure 7:
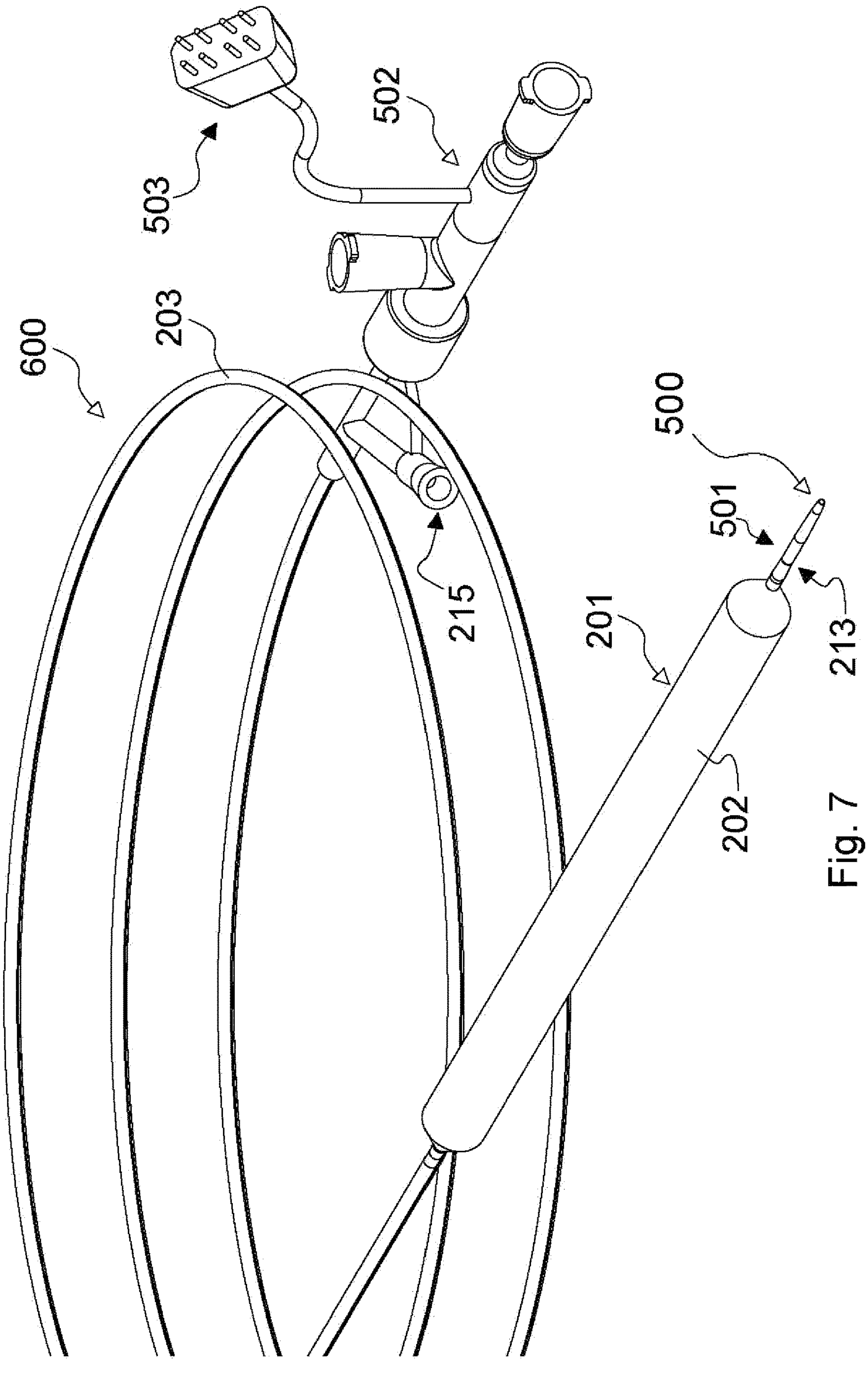
FIG. 7 is a schematic, perspective view of an adapter according to the present disclosure, attached to the distal end of a balloon catheter, and with a proximal electrical modular interface attached at the proximal end, forming an electrical modular catheter system. The balloon is represented as inflated for the purposes of illustration.

FIG. 7 is a schematic, perspective view of an assembled electrical modular catheter system 600 according to an aspect of the present disclosure. Assembled electrical modular catheter system 600 is a combination of medical device catheter 201 (also known as the parent module), electrical adapter 500, and proximal module 502. Proximal module 502, includes an electrical connector interface 503 and is attached to the proximal end 219 of fitting assembly 215 at the proximal end of the balloon catheter 201. The inflatable balloon 202 of balloon catheter 201 is represented as inflated for the purposes of illustration.

FIG. 6A and FIG. 6B illustrate the features of medical device balloon catheter 201 which includes a distal end 213 and proximal end 219. The balloon catheter 201 includes an inflatable balloon 202 positioned near the distal end 213. The inflatable balloon 202 is connected to a fitting assembly 215 near the proximal end 219 of medical device balloon catheter 201 by a catheter shaft 203. The catheter shaft 203 is typically a long tube with one or more lumens, at least one lumen 211 has an opening near the distal end 213.

FIG. 6B also illustrates electrical adapter 500 after it has been secured to medical device balloon catheter 201. Electrical adapter 500 is attached to medical device balloon catheter 201 by inserting the proximal end of adapter 478 into the distal end 213 of a lumen 211 of balloon catheter 201 until the attachment mechanism 467 has secured the adapter 500 to the balloon catheter 201. Interfacing elements 470, of the attachment mechanism 467, are attached or otherwise bonded to the elongated element 462 and configured to secure the electrical adapter 500 to a medical device catheter. Balloon catheter 201 is shown with the inflatable balloon 202 in an inflated state for illustration purposes but would normally be in a deflated state during the attachment of adapter 500 to balloon catheter 201. Alternatively, electrical adapter 500 could be attached to any other appropriate medical device catheter 201, for example a stent delivery system. Balloon catheter 201 may also include a fitting assembly 215 near the proximal end 219 of medical device balloon catheter 201 that includes a port to inflate the balloon and a port for "over-the-wire" guidewire access. The lumen 211 of a balloon catheter 201 is typically available to be used with a guidewire during a minimally invasive medical procedure. As described previously, electrical adapter 500 distal portion 501 may comprise, for example, electrically active elements 294, near the distal end 213 of the parent medical device catheter 201.

FIG. 7 illustrates the electrical adapter 500 after it has been secured to a medical device balloon catheter 201 and after a proximal module 502 has been attached to the proximal end 219 of the balloon catheter 201 and the proximal end 478 of electrical adapter 500. Proximal module 502 may include an electrical connector interface 503 to provide an electrical connection between the ring electrical contacts 473 of electrical connector 472 and a user interface or equipment for the electrically active adapter 500.

Figure 8:
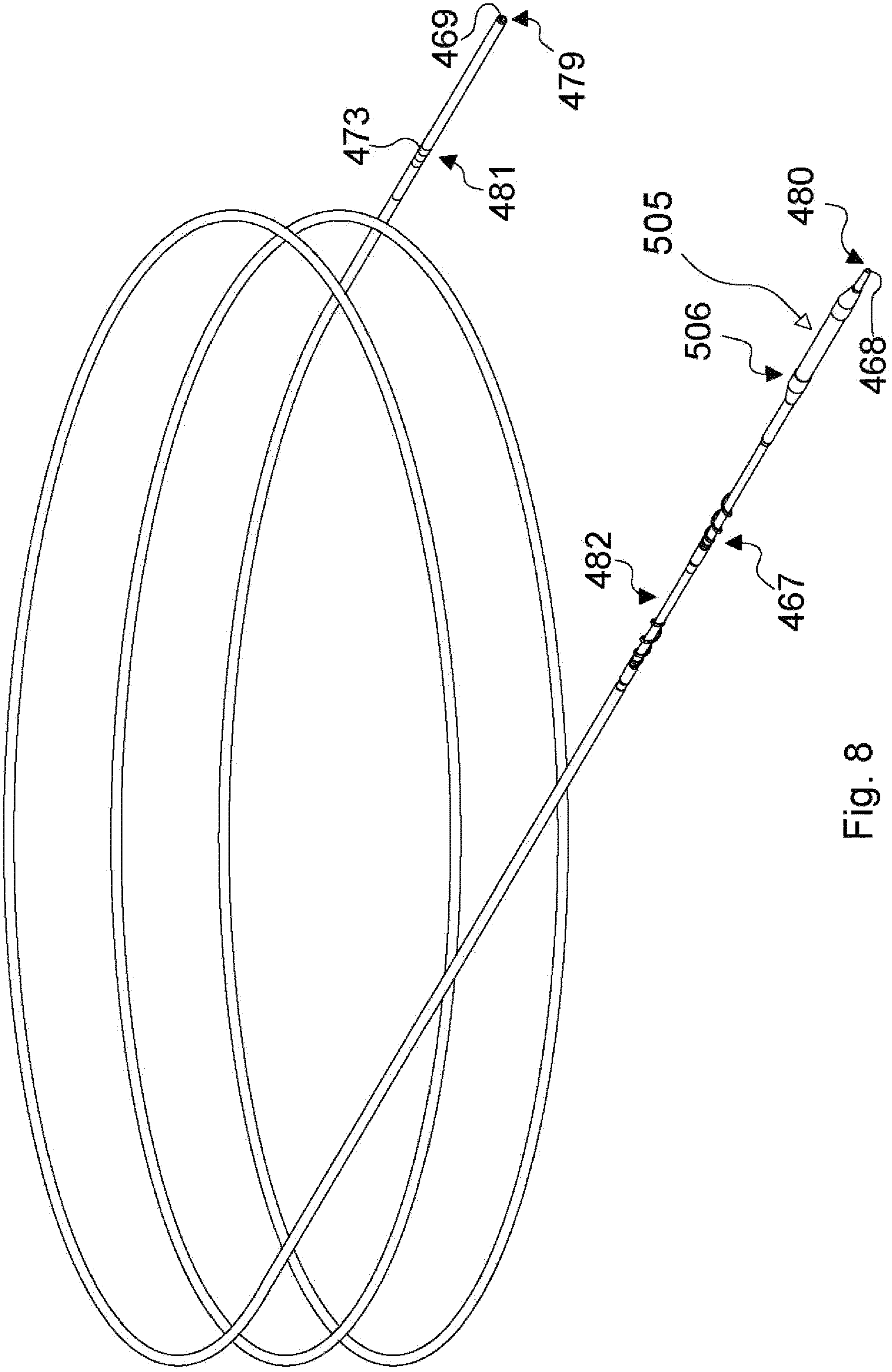
FIG. 8 is a schematic, perspective view of an adapter according to the present disclosure.

FIG. 8 is a schematic, perspective view of an over-the-wire (OTW) intravascular lithotripsy (IVL) adapter 505 according to an aspect of the present disclosure. OTW IVL adapter 505 includes a distal portion 506, which includes a distal exit 468 for a central lumen 465 at a distal end 480. OTW IVL adapter 505 also includes an attachment mechanism 467, elongate body 482, proximal end 479, proximal electrical connector 481, which includes ring electrical contacts 47. OTW IVL adapter 505 also includes proximal exit 469 at the proximal end 478 of OTW IVL adapter 505.

Figure 9:
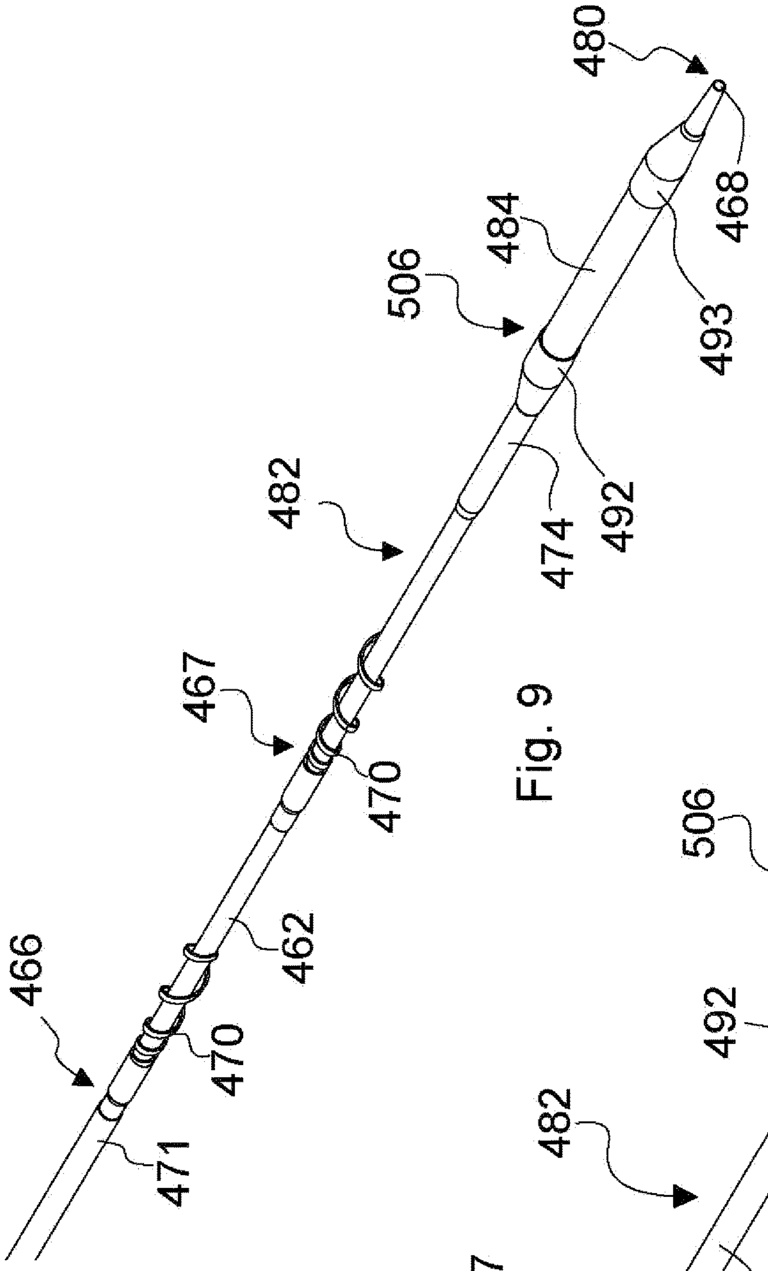
FIG. 9 is an enlarged detailed view of FIG. 8, showing part of a distal portion of the adapter, the attachment mechanism, and other features.

FIG. 9 is an enlarged detailed view, showing distal portion 506 of over-the-wire (OTW) intravascular lithotripsy (IVL) adapter 505, the attachment mechanism 467, and tubular extension 471 among other features. Distal portion 506 has a distal end 480 and includes runway 474, an outer tube 484, and the proximal and distal jacket or coverings 492 and 493 at the ends of outer tube 484. Attachment mechanism 467 includes elongated element 462 and interfacing elements 470. Elongated element 462 has a proximal end 466. FIG. 9 also shows elongate body 482.

Figure 10:
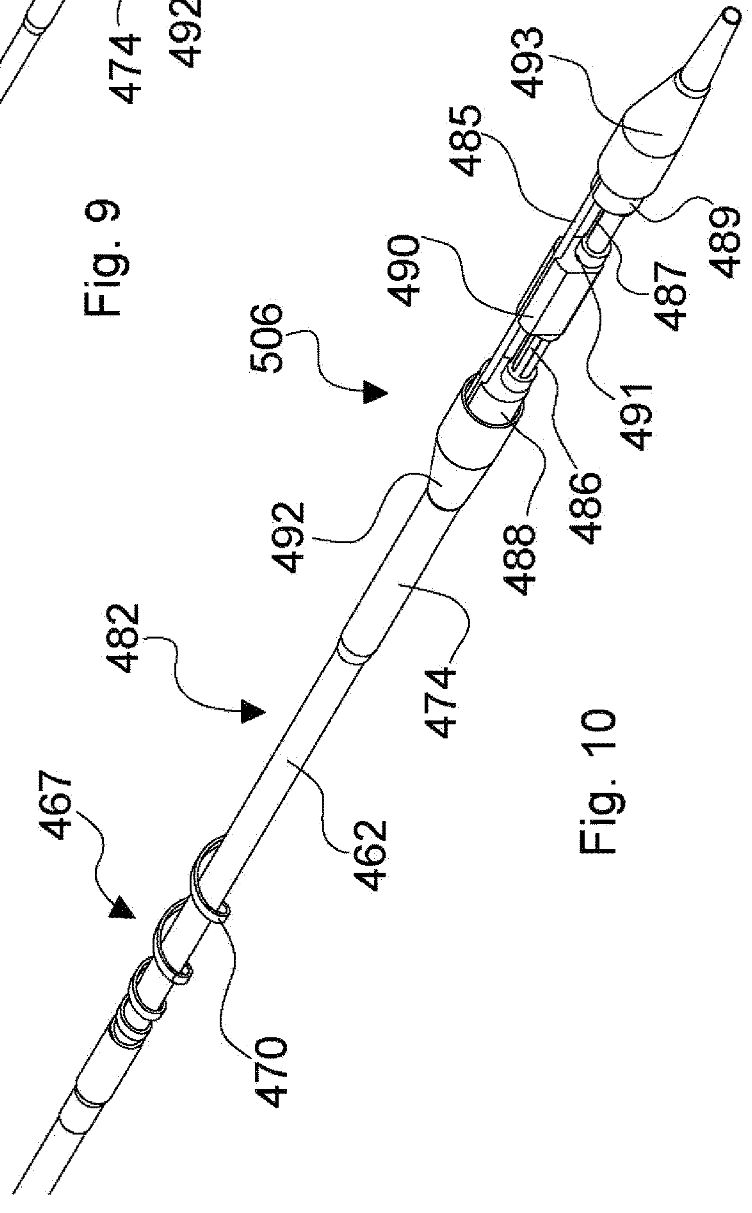
FIG. 10 is an enlarged detailed view of FIG. 8, showing the internal features and elements of a distal portion of the adapter.

FIG. 10 is an enlarged detailed view, showing distal portion 506 of over-the-wire (OTW) intravascular lithotripsy (IVL) adapter 505, like FIG. 9, but with outer tube 484 not shown to illustrate a cavitation bubble chamber 491, first electrode 486, second electrode 487, intermediate electrode 485, chamber separator 490, proximal plug 488, and distal plug 489.

Figure 11:
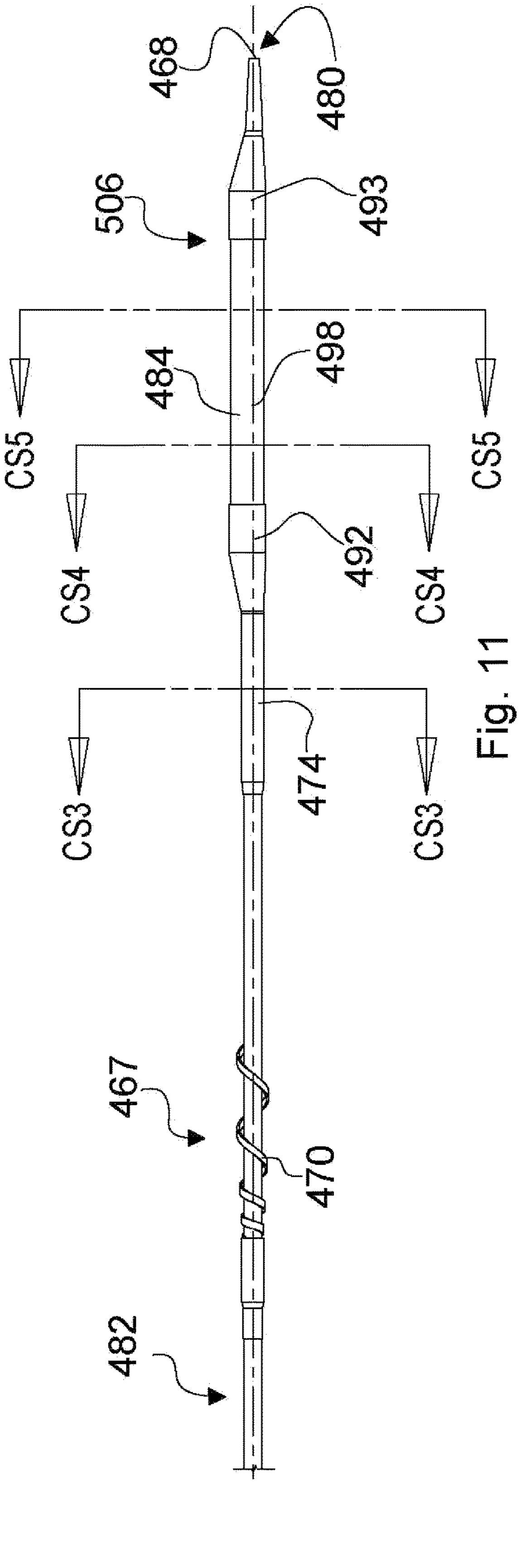
FIG. 11 is a partial schematic, longitudinal view of an adapter according to the present disclosure. Break line symbols are utilized to reduce the size of the drawing for clarity.

FIG. 11 is a partial schematic, longitudinal view of over-the-wire (OTW) intravascular lithotripsy (IVL) adapter 505 according to an aspect of the present disclosure. OTW IVL adapter 505 includes a distal portion 506, which includes a distal exit 468 for a central lumen 465 at a distal end 480 and includes runway 474, an outer tube 484, and the proximal and distal jacket or coverings 492 and 493 at the ends of outer tube 484. OTW IVL adapter 505 also includes an attachment mechanism 467 and elongate body 482. FIG. 11 also illustrates long or longitudinal axis 498 of the adapter 505 and cavitation bubble chamber 491.

Figure 12:
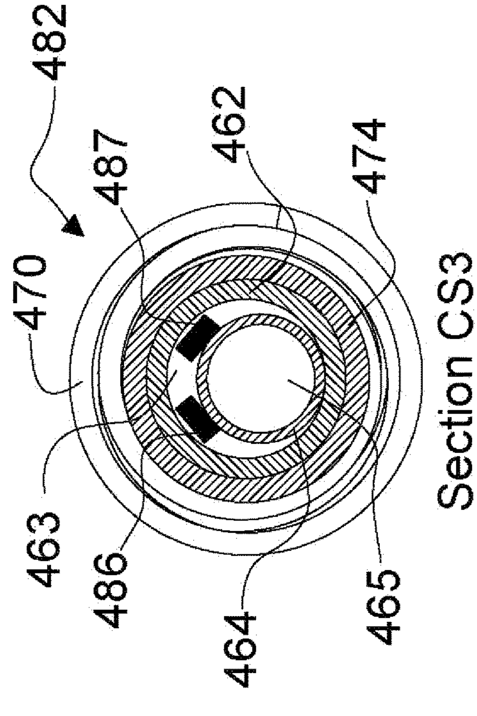
FIG. 12 is a partial schematic, transverse, cross-sectional view CS3 of the adapter of FIG. 11.

FIG. 12 is a partial schematic, transverse, cross-sectional view of OTW IVL adapter 505 at CS3 as illustrated in FIG. 11 showing elongate body 482 which includes first electrode 486, second electrode 487, second central tube 464, that creates central lumen 465, within the lumen 463 of elongated element 462. Also shown are interfacing element 470 bonded to the outside of elongated element 462, and runway 474.

Figure 13:
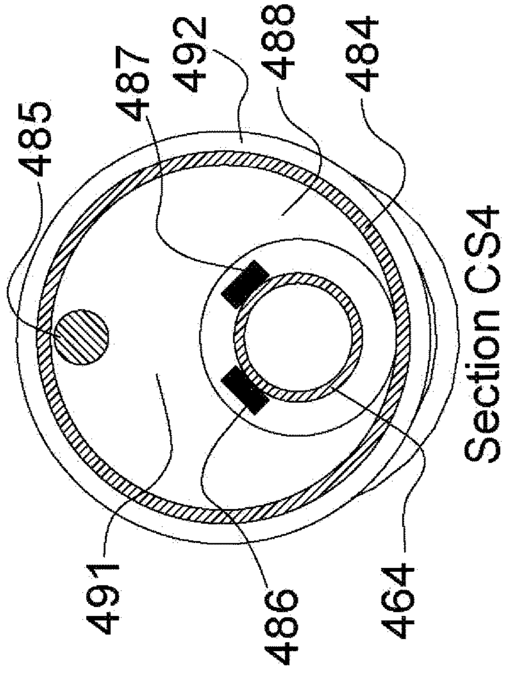
FIG. 13 is a partial schematic, transverse, cross-sectional view CS4 of the adapter of FIG. 11.

FIG. 13 is a partial schematic, transverse, cross-sectional view of OTW IVL adapter 505 at CS4 as illustrated in FIG. 11 showing outer tube 484, first electrode 486, second electrode 487, intermediate electrode 485, second central tube 464, cavitation bubble chamber 491, proximal plug 488, and proximal jacket or covering 492.

Figure 14:
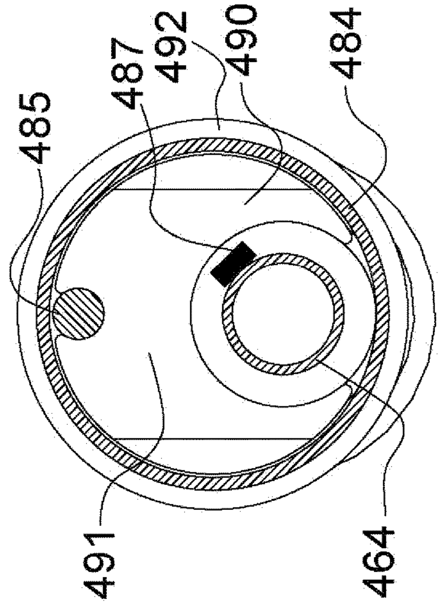
FIG. 14 is a partial schematic, transverse, cross-sectional view CS5 of the adapter of FIG. 11.

FIG. 14 is a partial schematic, transverse, cross-sectional view of OTW IVL adapter 505 at CS5 as illustrated in FIG. 11 showing outer tube 484, second electrode 487, intermediate electrode 485, second central tube 464, cavitation bubble chamber 491, chamber separator 490, and proximal jacket or covering 492

Figure 15:
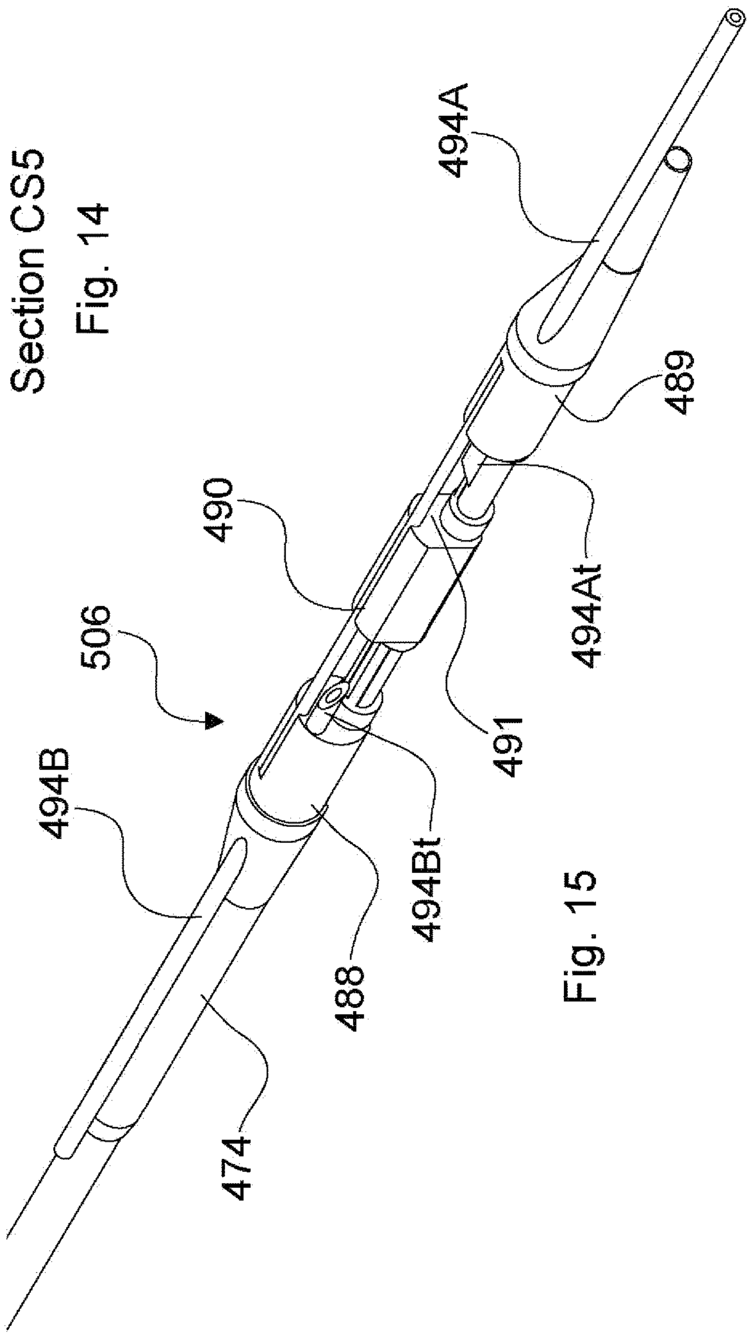
FIG. 15 is an enlarged detailed view of FIG. 8, showing the internal features and elements of a distal portion of the adapter.

FIG. 15 is an enlarged detailed view of distal portion 506 of OTW IVL adapter 505 like FIG. 9, but with outer tube 484, proximal jacket or covering 492, and distal jacket or covering 493 not shown to illustrate a cavitation bubble chamber 491, chamber separator 490, proximal plug 488, and distal plug 489. FIG. 15 also illustrates two needles 494A and B, which may be used to puncture the proximal plug 488 and distal plug 489, forming the boundary of the cavitation bubble chamber 491 along with the outer tube 484 (not shown), with the sharp tip of the needles 494At and/or 494Bt, penetrating and entering the cavitation bubble chamber 491.

FIGS. 8-10 illustrate an example of an over-the-wire (OTW) intravascular lithotripsy (IVL) adapter 505, with a distal end 480 and proximal end 479. OTW IVL adapter 505 is similar to the previously described electrical adapter 500 in that it comprises an elongate body 482, similar to elongate body 460, and attachment mechanism 467. OTW IVL adapter 505 also includes a distal portion 506 with a cavitation bubble chamber 491 within the body of the distal portion 506 for containing a cavitation solution. In one example, the cavitation bubble chamber 491 is filled with cavitation solution, typically with a conductivity solution below 20 micro-siemens per centimeter (μS/cm) during the manufacturing process. Viable cavitation solutions may include a 0.8M saccharose solution or deionized water, for example. Instead of filling the cavitation bubble chamber 491 during manufacturing, in an alternative embodiment, the cavitation bubble chamber 491 can be filled with a cavitation solution during a minimally invasive or endovascular procedure, for example, tableside in an operating room prior to inserting the adapter 505 and parent catheter 201 or combined modular system into the patient. When the cavitation bubble chamber is filled during a procedure, the cavitation solution may be saline or a mixture with saline, as non-limiting examples.

As shown with further reference to features of FIG. 11 and FIG. 12, the lumen 463 of the central tube 462 of the elongate body 482 could be used to fill the cavitation bubble chamber 491 with an appropriate solution during a procedure.

As illustrated in FIGS. 9-11, 13-15, the cavitation bubble chamber 491 is formed by an outer tube 484 located at distal portion 506 (note FIG. 10 illustrates distal portion 506 of adapter 505 without the outer tube 484 to show the internal features and elements relating to the cavitation bubble chamber 491). Additionally, the outer tube 484 is enclosed by a proximal plug 488 and a distal plug 489. The proximal plug 488 and distal plug 489 can be made from a polymer, typically through a molding manufacturing process or an extrusion process, with secondary reflow or bonding processes to enclose the proximal and distal ends of the outer tube 484 thereby creating the cavitation bubble chamber 491. Additionally, inside the outer tube 484 is a center chamber separator 490 to separate the chamber into two spaces where a cavitation bubble can be created between two distinct electrode sets, first electrode 486 and intermediate electrode 485, and second electrode 487 and intermediate electrode 485. The chamber separator 490 can also serve to support the center of the intermediate electrode 485, while the proximal plug 488 and distal plug 489 support the ends of the intermediate electrode 485.

In the example illustrated in FIG. 11 and the transverse cross-sectional views of FIGS. 12-14, the first electrode 486 and intermediate electrode 485, and second electrode 487 are illustrated as wires of various cross sections running parallel to each other along the long or longitudinal axis 498 of the adapter 505 and cavitation bubble chamber 491. The second electrode 487 and first electrode 486 may be configured as flat wires with a rectangular cross section, where the intermediate electrode 485 may be configured as a round wire, with a circular cross section. Other cross-sectional shapes could be useful, such as electrode wire with triangular cross sections. An advantage of this parallel electrode configuration is that the arcing or spark generation, and generated shockwave, between the electrodes can happen anywhere along the parallel lengths where the electrodes are mutually exposed (do not have electrical insulating coatings or covering). This may allow more cycles of arcing or spark generation because as the electrode wears with repeated arcing cycles the arcing can migrate to a fresh wire location farther along the parallel electrode wire set length. These electrodes may suitably be manufactured from copper, graphite, tungsten, stainless steel or other appropriate conducting materials. If the cavitation bubble chamber 491 is filled with the cavitation solution during the manufacturing process and will be in contact with the electrodes 487, 486 or 485, it may be advantageous to coat the conducting material with gold or other protective coating to minimize oxidation during an extended period of storage, such as during the shelf life of the product. If conductive wire is used as electrode 487 and 486, this wire can extend through the elongated body 482 to the ring electrical contacts 473 in electrical connector 481 of electrical adapter 505, to provide electrical continuity for communication with high voltage pulse generator 457 (such as shown with respect to FIG. 22). Alternatively, the electrodes 487 and 486 can be electrically connected to other electrical conductors 461 within or proximal to the cavitation bubble chamber 491 which are then electrically connected to the appropriate ring electrical contacts 473 in electrical connector 481 of adapter 505, such as shown in FIG. 8.

One method to fill the cavitation bubble chamber 491 with a cavitation solution is illustrated in FIG. 15. Note FIG. 15 illustrates distal portion 506 of OTW IVL adapter 505 without the outer tube 484, or the proximal and distal jacket or coverings 492 and 493 such as shown in FIG. 10. This is done to show the internal features and elements related to the cavitation bubble chamber 491. As shown, two needles 494A and B may be used to puncture the proximal plug 488 and distal plug 489 that form the boundary of the cavitation bubble chamber 491 along with the outer tube 484 (not shown), with the sharp tip of the needles 494At and/or 494Bt, penetrating and entering the cavitation bubble chamber 491. The cavitation solution may then be injected through the lumen of one or both of the needles 494A, B to fill the cavitation bubble chamber 491. It may be advantageous to inject the cavitation solution through one of the lumens of the needles 494A or B, while the other needle allows entrapped air to escape to enable a more complete filling of the cavitation bubble chamber 491. After the cavitation bubble chamber 491 is filled with the cavitation solution, it may be appropriate or necessary to cover the puncture sites in the proximal plug 488 and distal plug 489 with a proximal jacket or covering 492 and a distal jacket or covering 493 to seal the puncture sites (such as also shown in FIG. 9 and FIG. 10), ensuring the cavitation solution does not leak from the cavitation bubble chamber 491. The proximal jacket 492 and distal jacket 493 could be formed from a polymer and bonded, welded or attached to the distal portion 506. Alternatively, it may be advantageous to laser weld the puncture sites to seal the cavitation bubble chamber 491, among other techniques as may be appreciated in the art.

Figure 16:
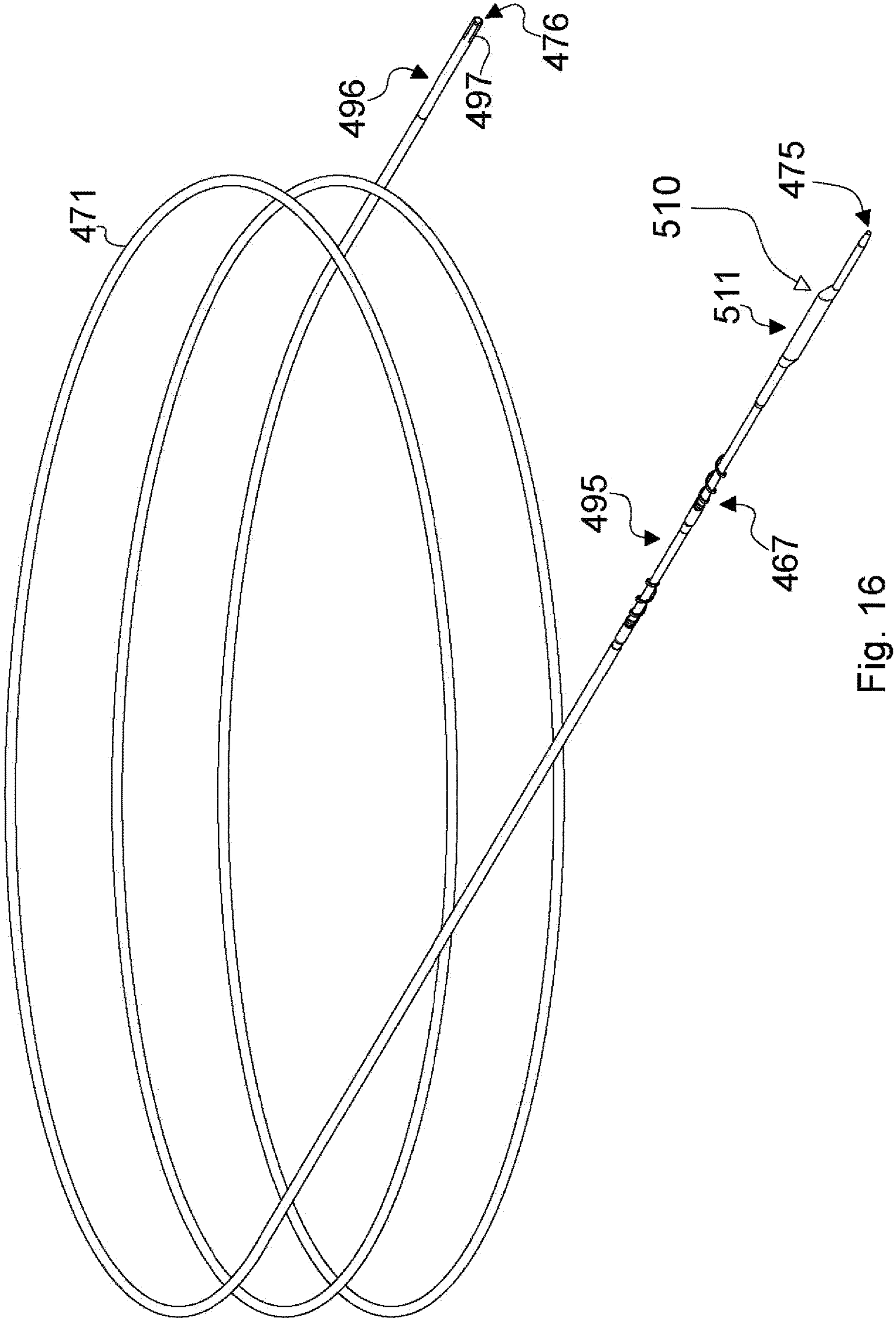
FIG. 16 is a schematic, perspective view of an adapter according to an embodiment of the present disclosure.

FIG. 16 is a schematic, perspective view of a rapid exchange (RX) intravascular lithotripsy (IVL) adapter 510 according to an aspect of the present disclosure. RX IVL adapter 510 includes a distal portion 511. RX IVL adapter 510 includes a distal end 475 and a proximal end 476. RX IVL Adapter 510 incorporates an attachment mechanism 467 and elongate body 495. RX IVL Adapter 510 also includes a tubular extension 471 and electrical connector 496, which includes tab electrical contacts 497.

Figure 17:
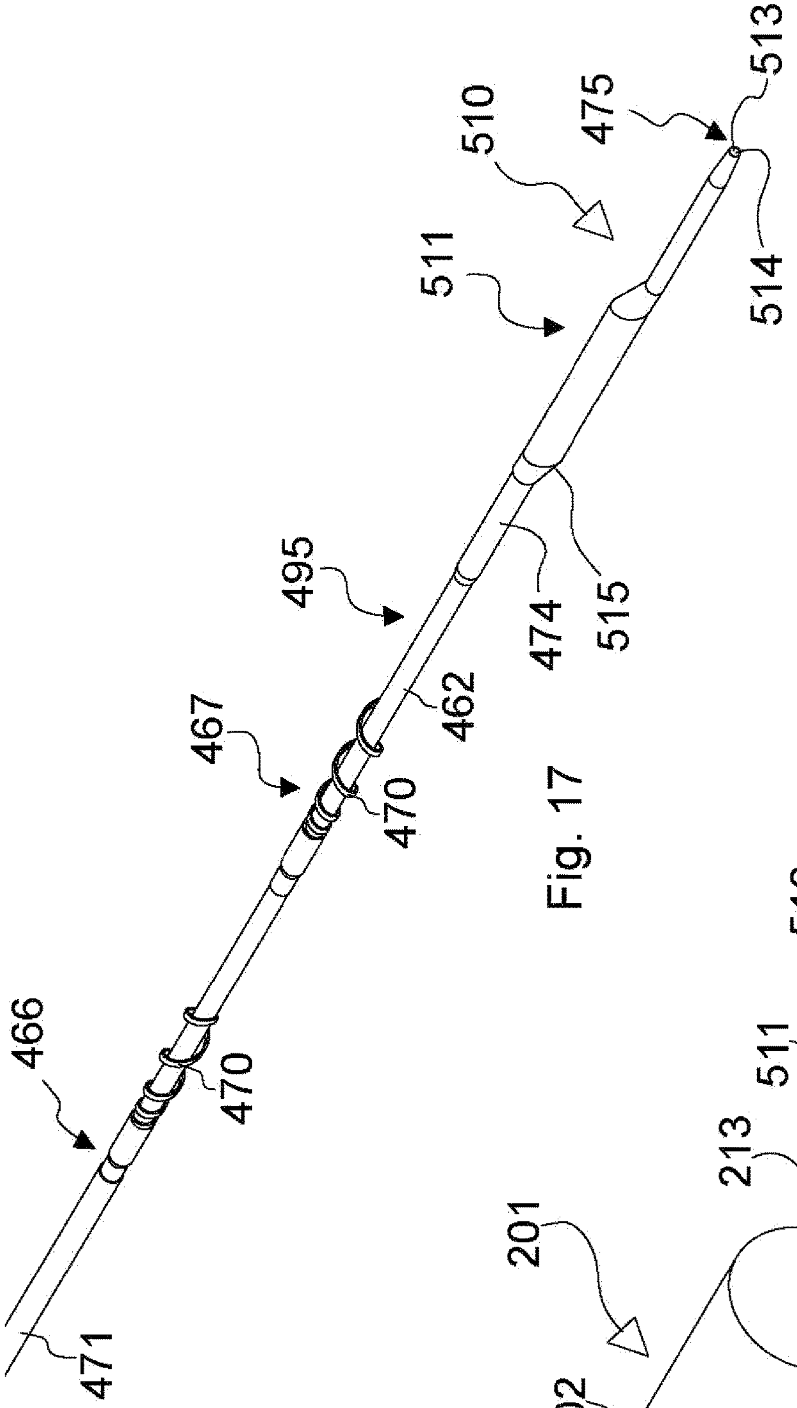
FIG. 17 is an enlarged detailed view of FIG. 16, showing part of a distal portion of the adapter, the attachment mechanism, and other features.

FIG. 17 is an enlarged detailed view of a rapid exchange (RX) intravascular lithotripsy (IVL) adapter 510 according to an aspect of the present disclosure illustrated in FIG. 16, showing distal portion 511 of RX IVL adapter 510, the attachment mechanism 467, elongate body 495, distal end 475, and proximal end 466 of elongated element, also known as central tube 462. Distal portion 511 includes rapid exchange lumen 513 with a distal end 514 and a proximal end 515, and runway 474. Attachment mechanism 467 includes interfacing elements 470 and elongated element 462.

Figure 18:
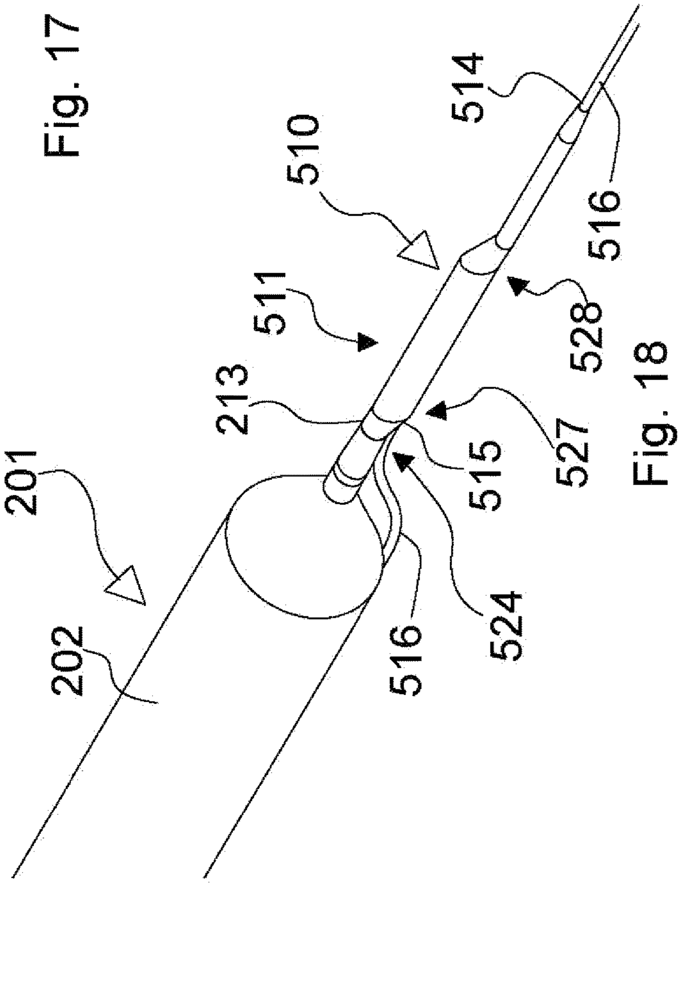
FIG. 18 is a partial schematic, perspective view of an adapter according to the present disclosure, attached to the distal end of a balloon catheter. The balloon is represented as inflated for the purposes of illustration.
Figure 21:
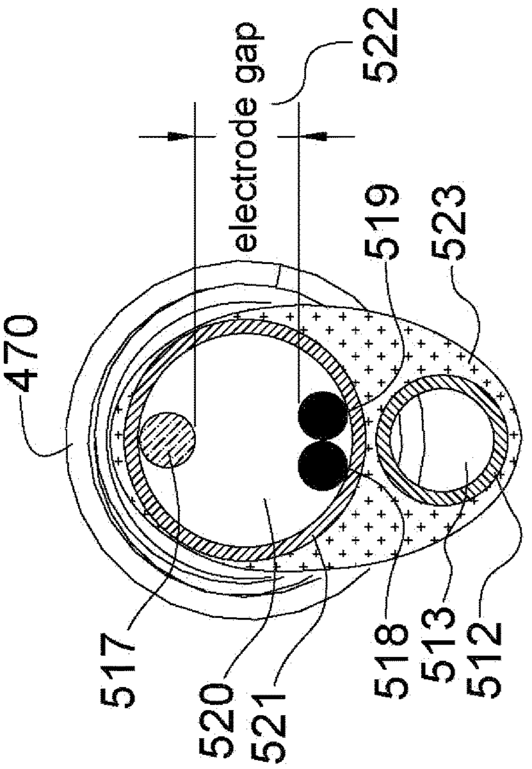
FIG. 21 is a partial schematic, transverse, cross-sectional view CS7 of the adapter of FIG. 19.

FIG. 18 is a partial schematic, perspective view of a rapid exchange (RX) intravascular lithotripsy (IVL) adapter 510 according to an aspect of the present disclosure, attached to a distal end 213 of a balloon catheter 201, where the inflatable balloon 202 is represented as inflated for the purposes of illustration, and a guidewire 516 is passing through distal end 514 and proximal end 515 of rapid exchange lumen 513 (illustrated in FIG. 17 and FIG. 21). Also illustrated in FIG. 18 is junction 524 between the distal portion 511 and distal end 213 of balloon catheter also known as parent module 201. Distal portion 511 of RX IVL adapter 510 includes cavitation bubble chamber 520 (illustrated in FIG. 21) which has a distal end 528 and a proximal end 527.

Figure 19:
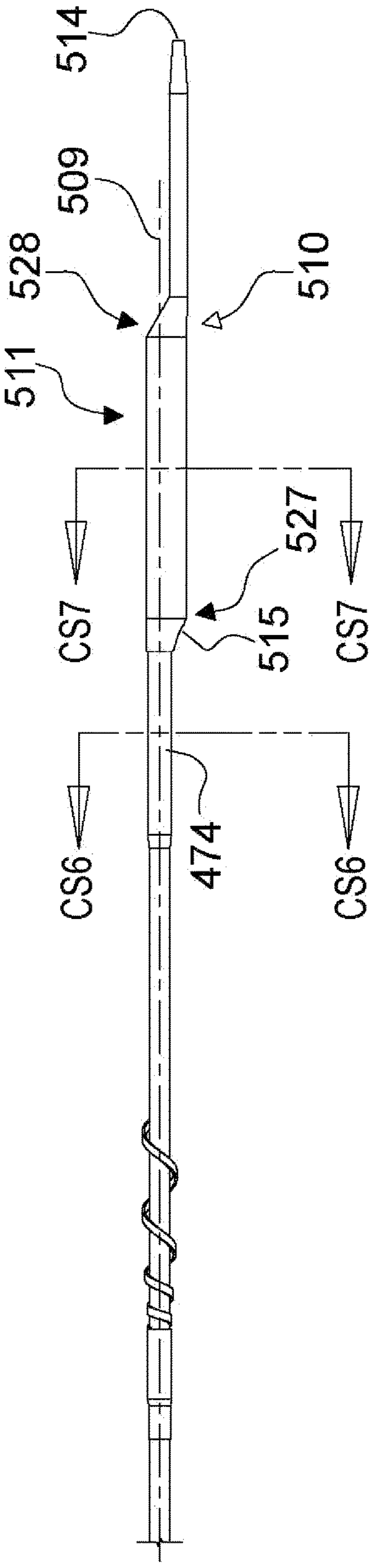
FIG. 19 is a partial schematic, longitudinal view of an adapter according to the present disclosure. Break line symbols are utilized to reduce the size of the drawing for clarity.

FIG. 19 is a partial schematic, longitudinal view of rapid exchange (RX) intravascular lithotripsy (IVL) adapter 510 according to an aspect of the present disclosure illustrated in FIG. 16, showing distal portion 511 of RX IVL adapter 510, Distal portion 511 includes rapid exchange lumen 513 (illustrated in FIG. 17 and FIG. 21) with a distal end 514 and a proximal end 515, runway 474, cavitation bubble chamber 520 (illustrated in FIG. 21) which has a distal end 528 and a proximal end 527. FIG. 19 also shows longitudinal or long axis 509 of the RX IVL adapter 510.

Figure 20:
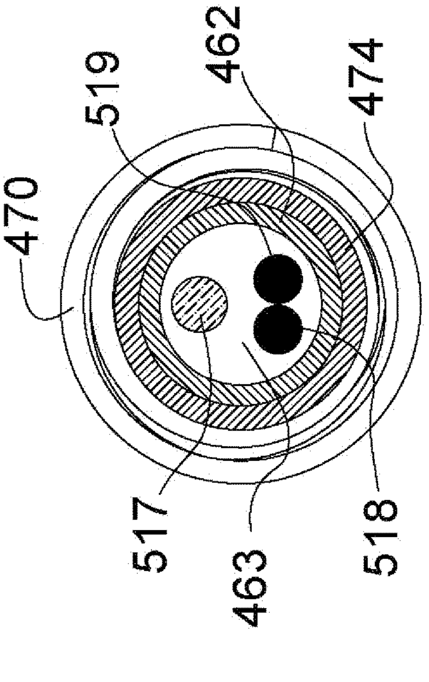
FIG. 20 is a partial schematic, transverse, cross-sectional view CS6 of the adapter of FIG. 19.

FIG. 20 is a partial schematic, transverse, cross-sectional view of RX IVL adapter 510 at CS6 as illustrated in FIG. 19 showing lumen 463 of elongated element 462, a first powered electrode 518, a second powered electrode 519, a ground electrode 517. Also shown is interfacing element 470, and runway 474.

FIG. 21 is a partial schematic, transverse, cross-sectional view of RX IVL adapter 510 at CS7 as illustrated in FIG. 19 showing cavitation bubble chamber 520, which is also the lumen of a cavitation bubble tube 521, a first powered electrode 518, a second powered electrode 519, a ground electrode 517, electrode gap 522 between electrodes, rapid exchange lumen 513 formed by a rapid exchange tube 512 surrounded by a polymer body 523. Also shown is interfacing element 470.

FIGS. 16-21 illustrate another example intravascular lithotripsy (IVL) adapter 510 according to the present disclosure. Adapter 510 comprises a distal portion 511, an elongate body 495 similar to 460 described previously, attachment mechanism 467 and electrical connector 496 with tab electrical contacts 497. Electrical conductors 461 electrically connect the three (3) tab contacts 497 on electrical connector 496 with the three (3) electrodes in the cavitation bubble chamber 520, a first powered electrode 518, a second powered electrode 519, and a ground electrode 517. Rapid exchange (RX) intravascular lithotripsy (IVL) adapter 510 has a distal end 475 and a proximal end 476. Distal portion 511 of RX IVL adapter 510 includes a rapid exchange lumen 513 (shown in FIG. 21) with a distal end 514 and a proximal end 515, the proximal end 515 is distal to the distal end 213 of the parent medical device catheter 201 (such as shown in FIG. 18), after the RX IVL adapter 510 has been attached to the distal end of the medical device catheter 201 by inserting the proximal end 476 of adapter 510 into a lumen 211 at the distal end 213 of medical device catheter 201. The distal portion 511 of RX IVL adapter 510 includes a runway 474 (also shown with reference to FIGS. 9-11 and 17-19). After attaching the RX IVL adapter 510 to parent module (balloon catheter) 201 a portion of the runway 474 fits within a lumen 211 at the distal end 213 of parent module 201. Typically, runway 474 is smaller than the lumen 211 at the distal end 213 of parent module 201 and is comprised of a polymer bonded or attached to the central tube 462. A purpose of the runway 474 is to provide a robust transition or junction 524 between the distal portion 511 of RX IVL adapter 510 and distal end 213 of parent module (balloon catheter) 201. The runway 474 would be designed to minimize kinking or buckling at the junction 524 between the distal portion 511 and distal end 213 of the parent module 201. The design of the runway 474 could include stainless steel braiding or higher durometer polymers to aid in providing a stable junction 524, for example.

The rapid exchange lumen 513, shown in FIG. 21, is designed through the choice of geometry and material to function as a rapid exchange lumen 513 for a guidewire 516 (shown in FIG. 18) to be used during a medical procedure. The rapid exchange lumen 513 could be formed by a separate rapid exchange tube 512 surrounded by a polymer body 523 (shown, for example, in FIG. 21). For example, a suitable rapid exchange tube 512 could be a thin walled, approximately 0.002" to 0.001", polyimide tube.

As shown in FIG. 17 to FIG. 21, the distal portion 511 of RX IVL adapter 510 also comprises a cavitation bubble chamber 520, which is also the lumen of a cavitation bubble tube 521. The cavitation bubble chamber 520 can be filled with a cavitation solution similar to cavitation bubble chamber 491 described previously. As illustrated, Cavitation bubble chamber 520 has a distal end 528 and a proximal end 527. Cavitation bubble chamber 520 can also include an opening at the distal end 528 to facilitate filling the cavitation bubble chamber 520 with a cavitation solution by allowing any entrapped air bubbles or vapor bubbles to escape. Within the cavitation bubble chamber 520 are three (3) electrodes, including a first powered electrode 518, a second powered electrode 519, and a ground electrode 517. The three (3) electrodes 517, 518, and 519 are illustrated as wires of round cross sections running parallel to each other along the longitudinal or long axis 509 of the adapter 510 and cavitation bubble chamber 520. The proximal end 515 of the rapid exchange lumen 513 is just proximal to the proximal end 527 of the cavitation bubble chamber 520. Alternatively, the proximal end 515 of the rapid exchange lumen 513 could be located anywhere between the distal end 528 of the cavitation bubble chamber 520 and the proximal end 527 of the cavitation bubble chamber 520. It may be advantageous to construct the distal portion 511 of RX IVL adapter 510 configured with the proximal end 515 of the rapid exchange lumen 513 distal to the distal end 528 of the cavitation bubble chamber 520. In this configuration, the rapid exchange lumen 513 would not have a portion running parallel to, or side by side with, the cavitation bubble chamber 520, as shown in FIG. 21, but could be characterized as a serial configuration, meaning the rapid exchange lumen 513 is more in line with cavitation bubble chamber 520. An advantage of the serial configuration would be a lower profile distal portion 511 with the drawback or tradeoff of a potentially longer distal portion 511.

The first powered electrode 518 and the second powered electrode 519 may also have an insulated coating that has been selectively removed or selectively applied such that a spark that generates a shockwave and cavitation plasma bubble 526 will be created across the electrode gap 522 at particular, or controlled uninsulated portions or locations along the length of the cavitation bubble chamber 520.

Figure 22:
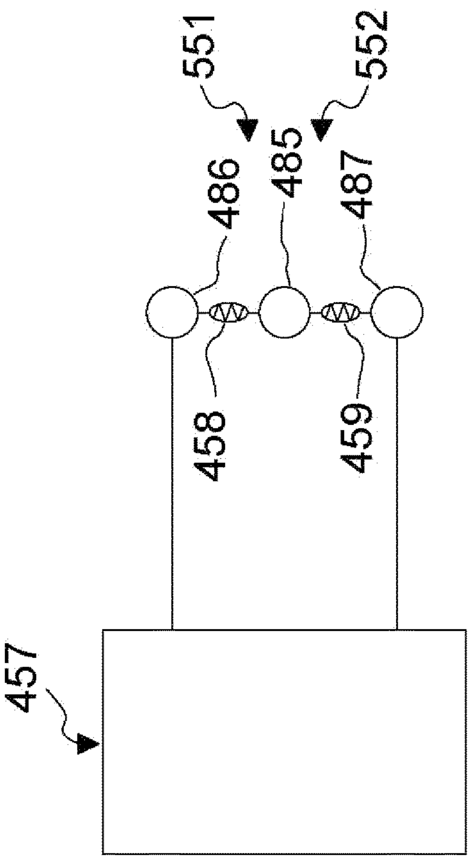
FIG. 22 is an example of a wiring schematic for use with an adapter according to the present disclosure.

FIG. 22 illustrates an example of a wiring circuit schematic suitable for use with over-the-wire (OTW) intravascular lithotripsy (IVL) adapter 505 according to an aspect of the present disclosure. FIG. 22 shows a high voltage pulse generator 457 which generates sparks and shockwaves that creates cavitation bubble 458 and cavitation bubble 459 by serially applying a high voltage potential difference between a first electrode set 551, the first electrode 486 and intermediate electrode 485, as well as between a second electrode set 552, intermediate electrode 485 and second electrode 487.

Figure 23:
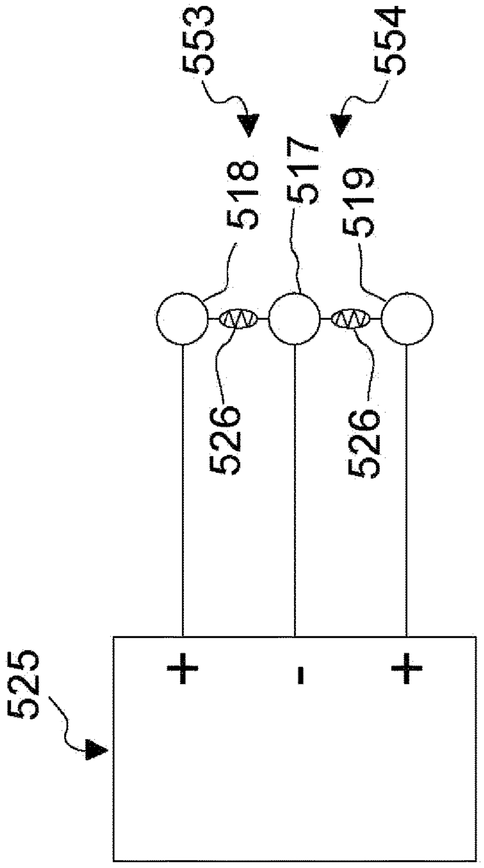
FIG. 23 is an example of another wiring schematic for use with an adapter according to the present disclosure.

FIG. 23 illustrates an example of wiring circuit schematic suitable for use with rapid exchange (RX) intravascular lithotripsy (IVL) adapter 510 according to an aspect of the present disclosure. As shown in FIG. 23 a high voltage pulse generator 525 creates an arc or spark generating a shockwave within the cavitation solution at the electrode gap 522 between the parallel lengths of the first powered electrode 518 and the ground electrode 517 as well as the second powered electrode 519 and ground electrode 517 in cavitation bubble chamber 520, which in turn creates cavitation bubbles 526 by applying parallel high voltage potential difference between a first electrode set 553, the first powered electrode 518 and the ground electrode 517, as well as between a second electrode set 554, the second powered electrode 519 and ground electrode 517.

Figure 24:
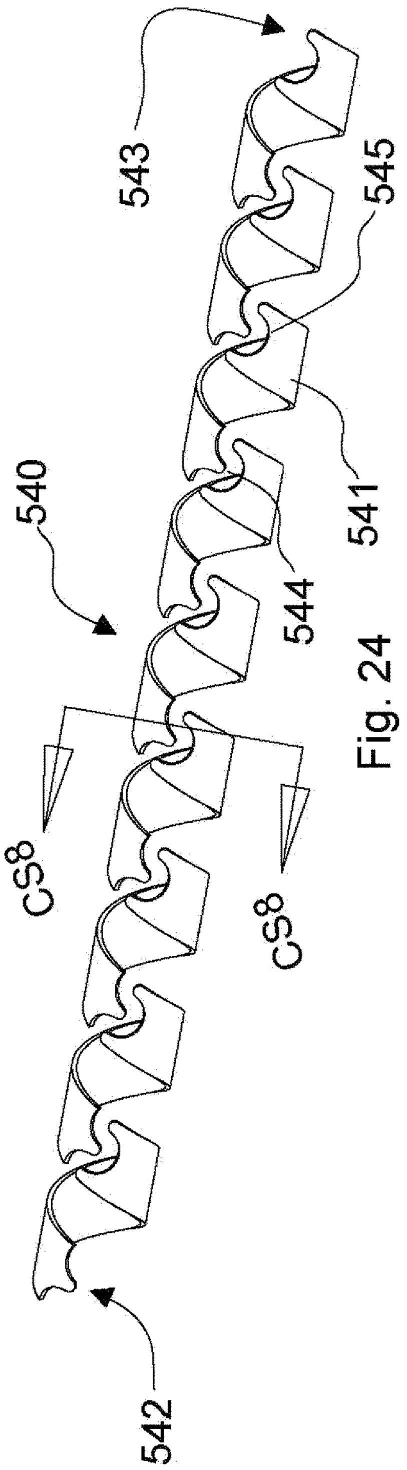
FIG. 24 is an alternate electrode configuration according to the present disclosure.

FIG. 24 illustrates a tubular electrode assembly 540 that could be incorporated into intravascular lithotripsy adapters according to an aspect of the present disclosure. Tubular electrode assembly 540 includes a series of tubular electrode elements 541 having a proximal end 544 and distal end 545 arranged in an end-to-end fashion, where the tubular electrode assembly 540 has a distal end 543 and proximal end 542.

Figure 25:
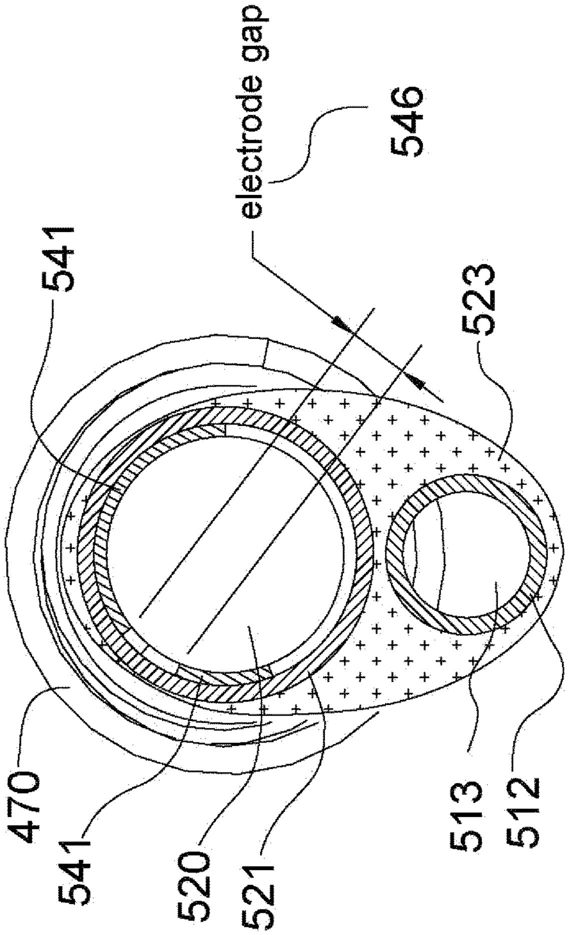
FIG. 25 is a partial schematic, transverse, cross-sectional view CS8 of the adapter of FIG. 24.

FIG. 25 is a partial schematic, transverse, cross-sectional view of a RX IVL adapter similar to RX IVL adapter 510. The cross-sectional view is like that of FIG. 21 showing section CS7 as illustrated in FIG. 19, but showing a cross-sectional view of a RX IVL adapter with tubular electrode assembly 540 at a location CS8 of FIG. 24. FIG. 25 illustrates tubular electrode elements 541 assembled in a cavitation bubble tube 521 forming cavitation bubble chamber 520, and electrode gap 546 between adjacent tubular electrode elements 541. FIG. 25 illustrates the other features, rapid exchange lumen 513 formed by a rapid exchange tube 512 surrounded by a polymer body 523, and interfacing element 470.

FIG. 24 and FIG. 25 illustrate an example of a suitable electrode configuration according to the present disclosure. In this example a series of tubular electrode elements 541 are arranged end to end, into a tubular electrode assembly 540. As shown in the example of FIG. 24, nine (9) tubular electrode elements 541 are arranged in a series forming the tubular electrode assembly 540 having eight (8) electrode gaps 546. In this example, the tubular electrode element 541 can be manufactured by laser cutting the spiral shape from tubular stock of an appropriate material with the required diameter and wall thickness. The electrode gap 546 is formed between the proximal end 544 of a tubular electrode element 541 and the distal end 545 of an adjacent tubular electrode element. As an alternative to the spiral shape of the tubular electrode element 541, the shape could be a circumferential ring, where an appropriate electrode gap is configured between adjacent circumferential ring electrode elements. The tubular electrode element 541 at the proximal end 542 of the tubular electrode assembly 540 is electrically connected to one side of a high voltage pulse generator 457 (such as shown in FIG. 22) and the other electrical side of the high voltage pulse generator is electrically connected to the tubular electrode element 541 at the distal end 543 of the tubular electrode assembly 540. When an appropriate high voltage pulse is applied, a spark, shockwave, and cavitation bubble will be created at each of the eight (8) electrode gaps 546. The tubular electrode assembly 540 could be incorporated into a distal portion of an adapter similar to distal portion 511 of adapter 510 described previously, but wherein the tubular electrode assembly 540 forms the cavitation bubble chamber 520. Cross-sectional view CS8 of FIG. 25 illustrates the adapter incorporating tubular electrode assembly 540 similar to RX IVL adapter 510 and the cross sectional view CS7 of FIG. 21 previously described, where the section arrows of FIG. 24 show approximate location of section CS8 of adapter 510 incorporating tubular electrode assembly 540. Electrode pair configurations, or electrode sets could include pairing a tubular electrode element with a wire or other electrode element.

Figure 26:
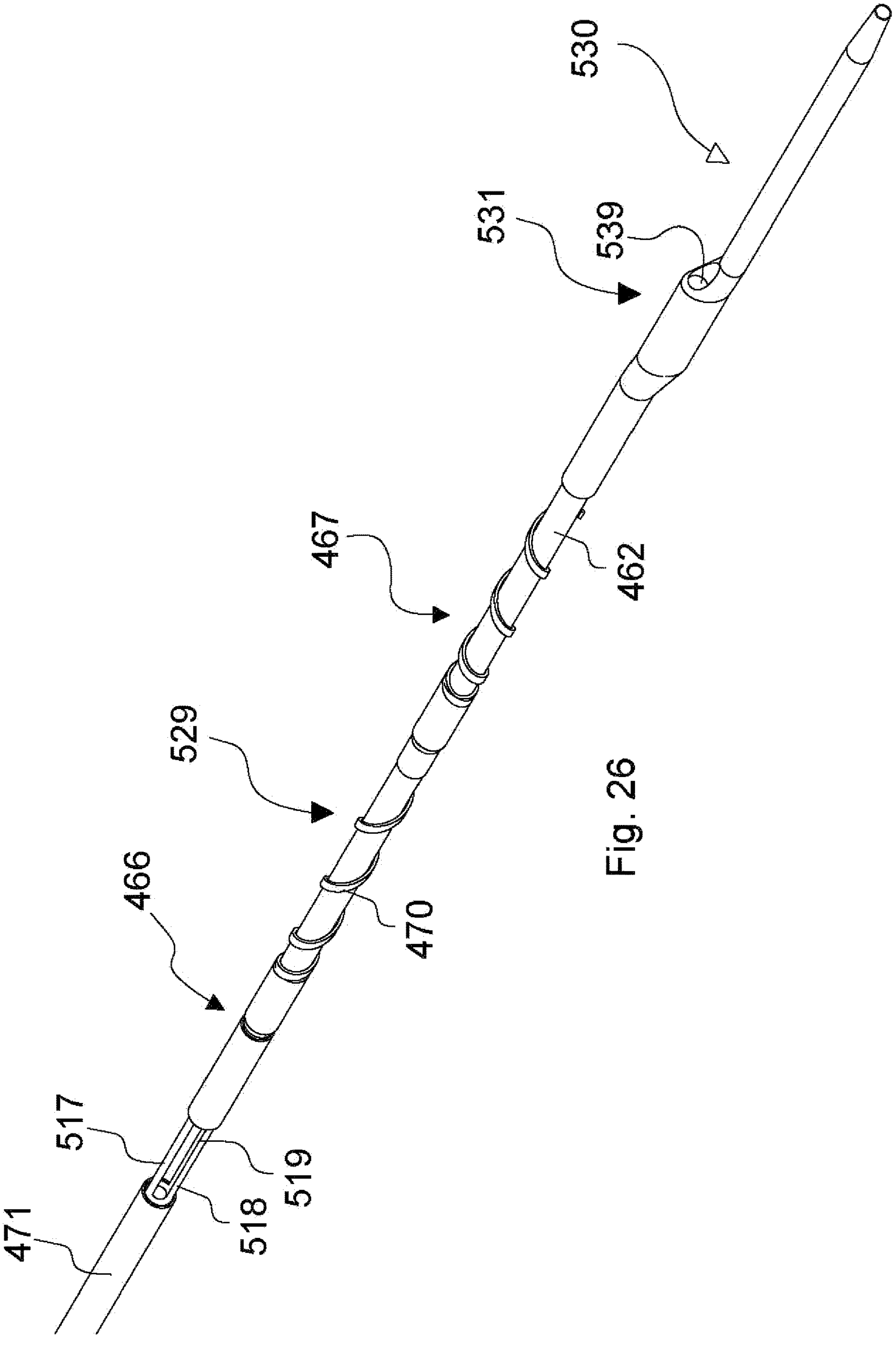
FIG. 26 is a partial schematic, perspective view of an adapter according to the present disclosure.

FIG. 26 is partial schematic view of an intravascular lithotripsy (IVL) adapter 530 according to an aspect of the present disclosure, showing distal portion 531 and proximal portion 529 of IVL adapter 530, attachment mechanism 467, and proximal end 466 of elongated element, also known as central tube 462. Distal portion 531 can include an opening 539 at the distal end to facilitate filling with a cavitation solution by allowing any entrapped air bubbles or vapor bubbles to escape. Proximal portion 529 includes attachment mechanism 467 which includes interfacing elements 470 and elongated element 462, three (3) electrodes, a first powered electrode 518, a second powered electrode 519, and a ground electrode 517, and tubular extension 471. Three (3) electrodes, a first powered electrode 518, a second powered electrode 519, and a ground electrode 517 are proximal to proximal end 466 of elongated element, also known as central tube 462.

In another example as illustrated in FIG. 26, electrode configurations similar to that illustrated in adapter 505 and 510 previously described could be positioned proximal to the attachment mechanism 467, instead of at distal portion 506 or distal portion 511. In this case, the cavitation bubble tube 521 or outer tube 484 could be omitted such that the lumen 211 of the balloon catheter 201 would act as cavitation bubble chambers 520 and 491. As shown in FIG. 26, adapter 530 includes a distal portion 531, and a proximal portion 529. Distal portion 531 that includes rapid exchange lumen for guidewire functionality that doesn't require the distal lumen of a medical device catheter. As shown in FIG. 26, electrodes 517, 518, and 519 are positioned at the proximal portion 529, just proximal to the attachment mechanism 467 and just distal to the tubular extension 471. In this configuration, the shockwave generating electrodes can be positioned in the location of the inflatable balloon 202 of an angioplasty balloon catheter parent module 201, instead of in the distal portion 531, distal to the balloon of an angioplasty balloon catheter parent module. The cavitation bubble chamber region, in this case the region of the lumen 211 of the balloon catheter 201 where the electrode set 517, 518, and 519 are positioned, can be filled with a cavitation solution similar to cavitation bubble chamber 520 described previously. Distal portion 531 can also include an opening 539 at the distal end to facilitate filling with a cavitation solution by allowing any entrapped air bubbles or vapor bubbles to escape.

Figure 27:
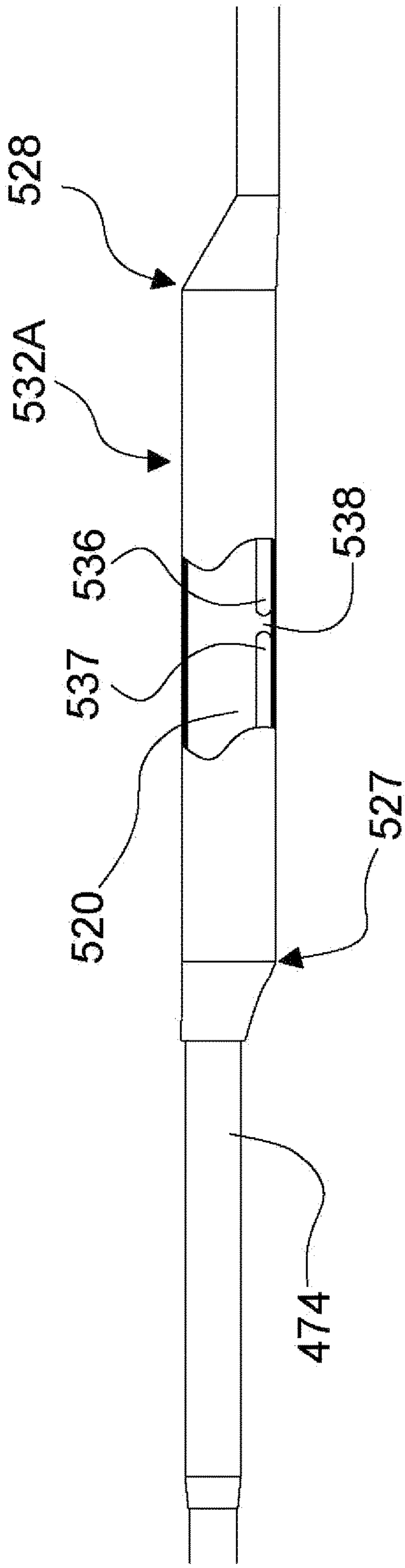
FIG. 27 is a partial schematic longitudinal view with partial cutaway cross-sections of an alternate electrode configuration according to the present disclosure.

FIG. 27 is partial schematic view of an intravascular lithotripsy (IVL) adapter according to an aspect of the present disclosure, showing cutaway section view of distal portion 532A. Distal portion 532A includes a cavitation bubble chamber 520 with a distal end 528 and proximal end 527, runway 474, and co-linear, end-to-end electrodes, 536 and 537, within cavitation bubble chamber 520.

Figure 28:
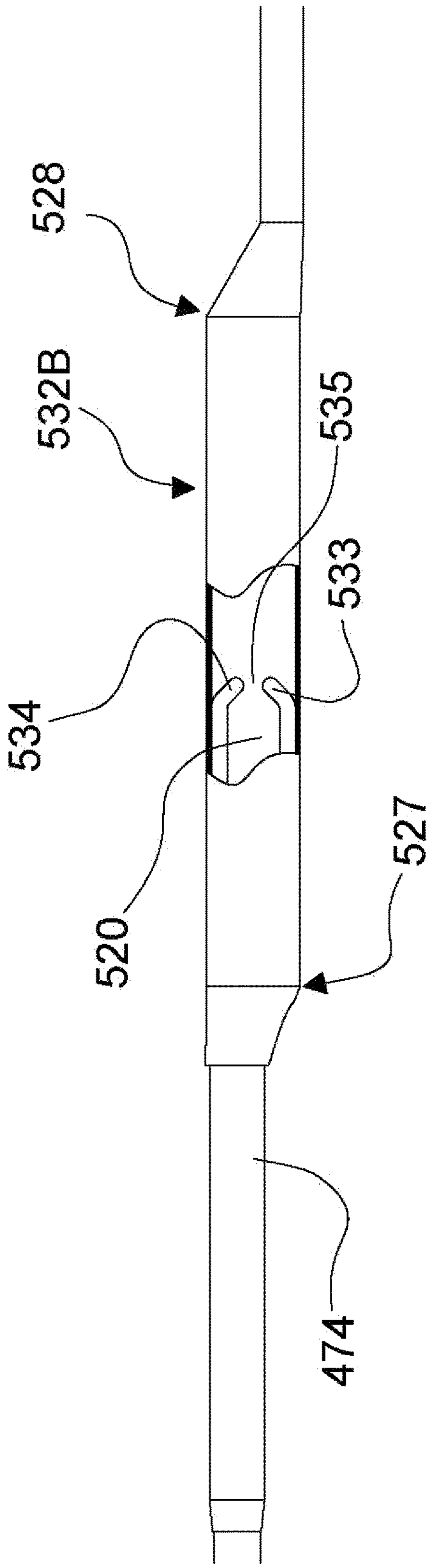
FIG. 28 is a partial schematic longitudinal view with partial cutaway cross-sections of an alternate electrode configuration according to the present disclosure.

FIG. 28 is partial schematic view of an intravascular lithotripsy (IVL) adapter according to an aspect of the present disclosure, showing cutaway section view of distal portion 532B. Distal portion 532B includes a cavitation bubble chamber 520 with a distal end 528 and proximal end 527, runway 474, and parallel, end-to-end electrodes, 533 and 534, within cavitation bubble chamber 520. Instead of mostly parallel wire electrodes as shown in the example of adapters 505 and 510 of the present disclosure, the electrodes in the distal portions 506 and 511, respectively, can be configured in an end-to-end configuration of distal portion 532A and distal portion 532B as shown in FIG. 27 and FIG. 28. The parallel wire electrode configuration as shown in adapters 505 and 510 has advantages in ease of manufacturing but has drawbacks in that there is not a specific location where the arc or spark would occur along the length of the electrode, which may be problematic if the shockwave energy would need to be focused or precisely located. The end-to-end configuration as illustrated in FIG. 27 and FIG. 28 could be arranged to provide a more precise arc or spark location.

FIG. 27 and FIG. 28 are longitudinal views with partial cutaway cross-sections of distal portions 532A and 532B to illustrate the interior of a cavitation bubble chamber 520 and alternate electrode configurations. FIG. 27, illustrates a pair of co-linear, end-to-end electrodes, 536 and 537, within cavitation bubble chamber 520. Applying a sufficiently high voltage potential difference between the set of electrodes 536 and 537 will induce arcing or sparking, generating a shockwave, at the electrode gap 538 between the ends of electrodes 537 and 536 within the cavitation solution, and associated cavitation bubble. FIG. 28 illustrates a pair of parallel, end-to-end electrodes, 533 and 534, within cavitation bubble chamber 520. Applying a sufficiently high voltage potential difference between the set of electrodes 533 and 534 will induce arcing or sparking, generating a shockwave, at the electrode gap 535 between the ends of electrodes 534 and 533 within the cavitation solution, and associated cavitation bubble.

Figures 29, 30:
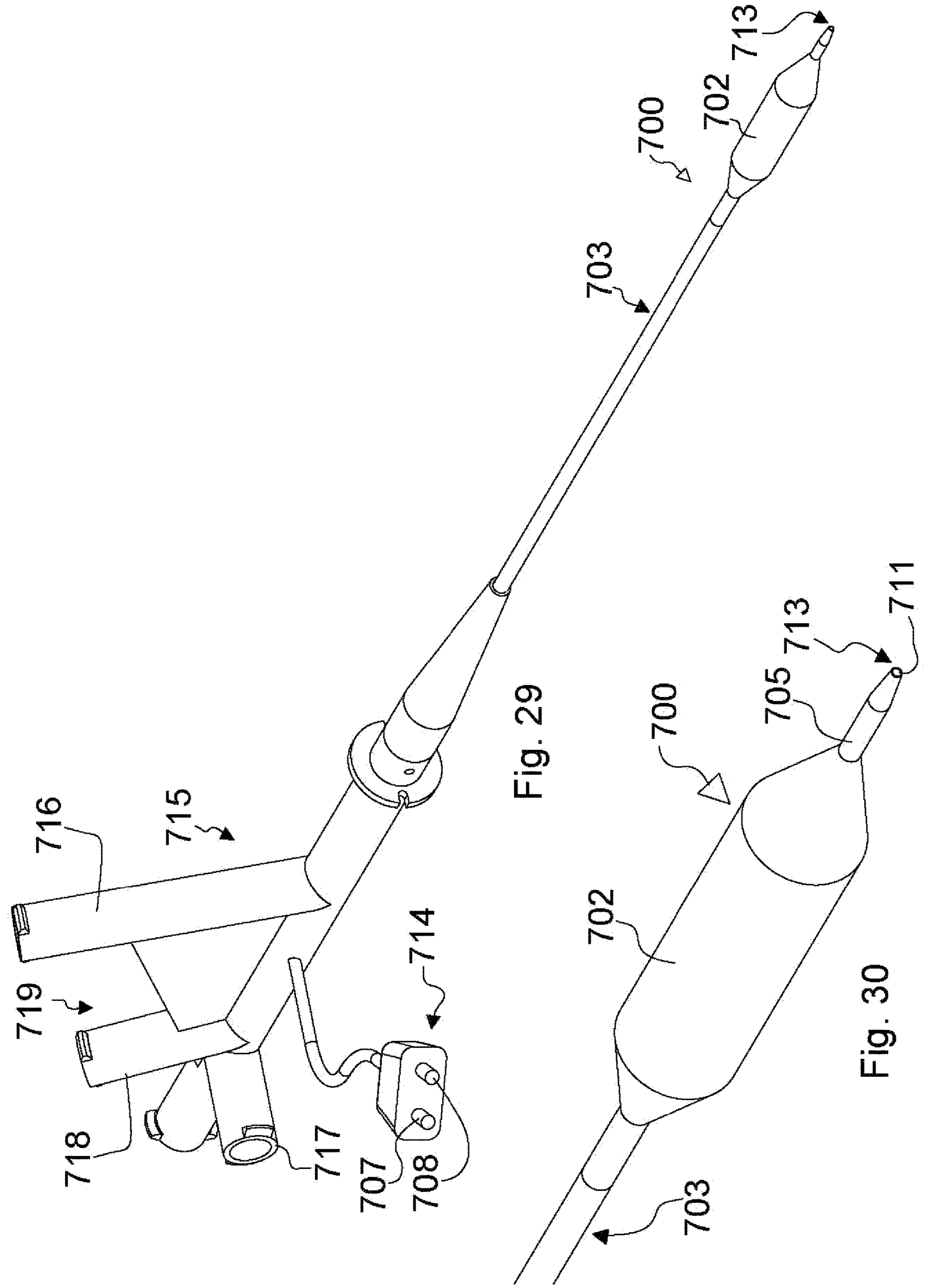
FIG. 29 is a schematic, perspective view of a medical device balloon catheter according to the present disclosure.
FIG. 30 is an enlarged detailed view of FIG. 29, showing part of a distal portion of the catheter.

FIG. 29 and FIG. 30 illustrate the features of a medical device balloon catheter 700 which includes a distal end 713 and proximal end 719. The balloon catheter 700 includes an inflatable balloon 702 positioned near the distal end 713. The inflatable balloon 702 is connected to a fitting assembly 715 near the proximal end 719 of medical device balloon catheter 700 by a catheter shaft 703. The catheter shaft 703 is typically a long tube with one or more lumens, and at least one lumen is used to inflate inflatable balloon 702. This inflation lumen is typically connected to an inflation device to pressurize the inflatable balloon 702, typically with saline solution, at inflation fitting 716, for example. Fitting assembly 715 also includes a first cavitation solution fitting 717, and a second cavitation solution fitting 718 that are connected to a first cavitation solution lumen or cavity and a second cavitation solution lumen or cavity which creates fluid flow paths, or connections, extending between the cavitation bubble chamber and first and second cavitation solution fittings, 717 and 718. Fitting assembly 715 also includes an electrical connector 714 that includes at least two electrical connector pins, a first electrical connector pin 707 and a second electrical connector pin 708. Electrical connector 714 and the first and second electrical connector pins 707 and 708 respectively are adapted to electrically couple, or connect, a high voltage pulse generator to electrode pairs in the cavitation bubble chamber.

The medical device balloon catheter 700 of FIGS. 29-36 is a balloon catheter that may also be conceptualized as an integrated, unitary or "one-piece" design version of the assembled modular catheter system, comprising an intravascular lithotripsy (IVL) adapter attached to a medical device balloon catheter described with reference to FIGS. 1-28. Instead of two modules attached together to combine the features of an inflatable balloon with a cavitation bubble chamber at the distal end to deliver shockwave energy, medical device balloon catheter 700 may integrate the IVL features and inflatable balloon features in a "non-modular" or unitary design. The distal end 713 of medical device catheter 700 is intended to be inserted into a body lumen, such as a vessel, artery, vein, or duct to deliver the shockwave energy and angioplasty in the form of an inflatable and pressurized balloon 702. The proximal end 719 is intended to stay outside the body of the patient and is where the user interfaces with the medical device catheter 700, such as connecting a high voltage pulse generator, pressurizing the inflatable balloon 702, and circulating cavitation solution to the distal end 713.

Figure 31:
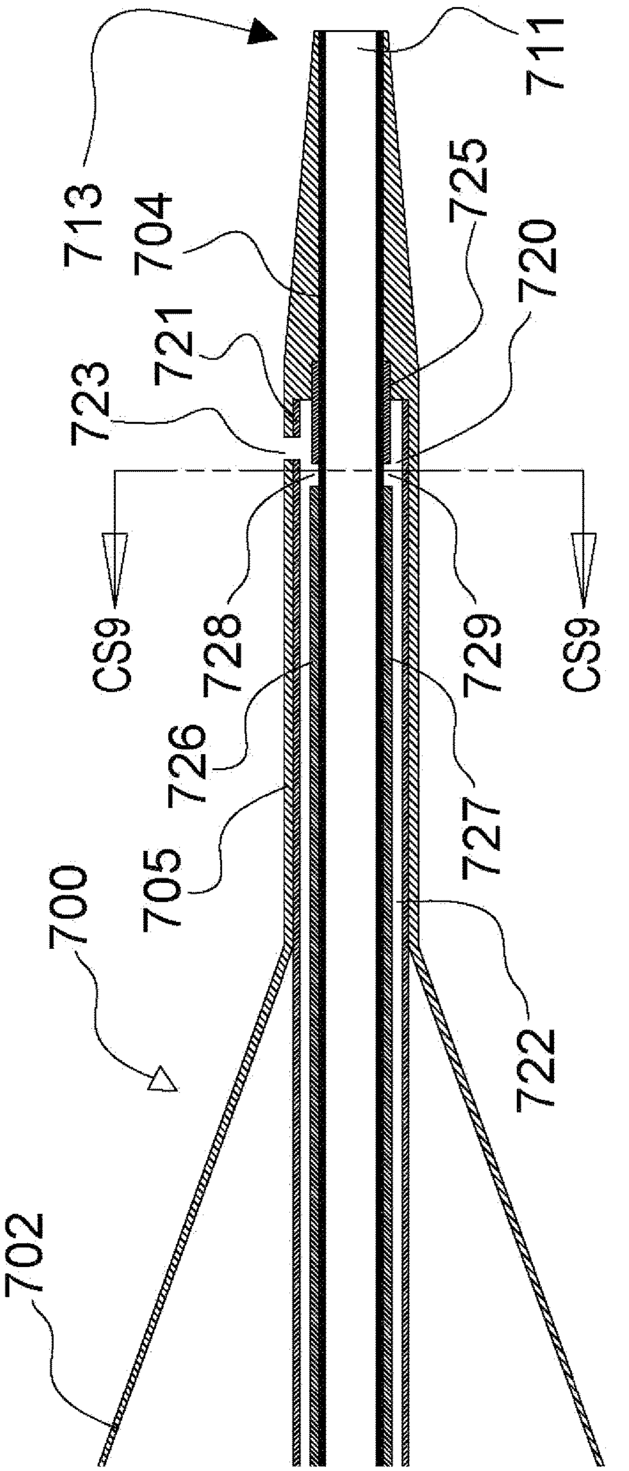
FIG. 31 is a partial schematic, longitudinal cross-sectional view of the distal end of a medical device balloon catheter according to the present disclosure.

FIG. 31 is partial schematic, longitudinal cross-sectional view of a medical device balloon catheter 700 according to an aspect of the present disclosure, showing a sectional view of a portion of medical device catheter 700, including the features at the distal end 713. Medical device balloon catheter 700 includes a guidewire lumen 711 formed by a guidewire tube 704, which extends coaxially through a cavitation bubble chamber 720, an intermediate electrode 725, and the inflatable balloon 702. Cavitation bubble chamber 720 is formed by a tube, cavitation bubble chamber tube 721. Medical device balloon catheter 700 may also include a first electrode 726, a second electrode 727, and a single cavitation solution cavity 722 that extends from the cavitation bubble chamber 720 at the distal end 713 through the inflatable balloon 702 to a location outside the body of the patient, for example at the fitting assembly 715 near the proximal end 719 of medical device balloon catheter 700. When only a single cavitation solution cavity 722 is required, only one of the cavitation solution fittings, for example first cavitation solution fitting 717 as shown in FIG. 29, is needed. In this case, the single cavitation solution cavity 722 creates fluid flow paths, or connections, extending between the cavitation bubble chamber 725 and first cavitation solution fittings, 717. Medical device balloon catheter 700 may also include an inflatable balloon 702 that transitions to a distal balloon tail 705 that seals the distal end of the inflatable balloon 702 near the distal end 713. The distal balloon tail 705 may be composed of a polymer that is the same as the inflatable balloon 702 and forms the outer surface of this portion of the balloon catheter 700, where a similar or compatible polymer may typically be formed into a taper at the distal end 713 where the distal exit of the guidewire lumen 711 is located. FIG. 31 also shows the electrode gap 728 between first electrode 726 and intermediate electrode 725 and electrode gap 729 between second electrode 727 and intermediate electrode 725. The medical device balloon catheter 700 may also include an opening 723, such as a hole, slit, or passage near the cavitation bubble chamber 720 through the distal balloon tail 705 and cavitation bubble chamber tube 721. A suitable cavitation solution, such as saline solution, can be moved to create a one-way flow of solution from the first cavitation solution fitting 717, through the cavitation solution cavity 722, exiting the cavitation bubble chamber 725 at opening 723. A syringe or similar device can be connected to the cavitation solution fitting 717 to inject cavitation solution to accomplish said one-way fluid movement.

Figure 32:
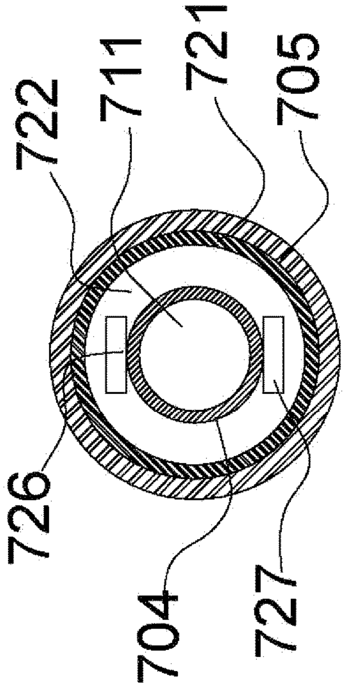
FIG. 32 is a partial schematic, transverse cross-sectional view CS9 of the medical device balloon catheter of FIG. 31.

FIG. 32 is a partial schematic, transverse cross-sectional view of medical device balloon catheter 700 at cavitation bubble chamber 720, or CS9 as illustrated in FIG. 31, and showing guidewire tube 704, guidewire lumen 711, first electrode 726, second electrode 727, cavitation bubble chamber tube 721, distal balloon tail 705, and cavitation solution cavity 722 which is a single lumen cavity.

The electrode configuration of intermediate electrode 725, first electrode 726, and second electrode 727 shown in FIGS. 31 and 32 are like the configuration of intermediate electrode 485, first electrode 486, and second electrode 487 as shown in FIG. 22, where a high voltage pulse generator 457 can be used to generate sparks and associated shockwaves by serially applying a high voltage potential difference between the first electrode 726 and intermediate electrode 725, and between intermediate electrode 725 and second electrode 727. Electrical communication or electrical connection between the first electrode 726 and second electrode 727, and the high voltage pulse generator 457 may be established by electrically coupling or electrically connecting the first electrode 726 to the first electrical connector pin 707 and the second electrode 727 to the second electrical connector pin 708 at the electrical connector 714. Electrical connector 714 may be adapted to be electrically connected to the pulse generator 457 to deliver the required high voltage pulses at electrode gaps 728 and 729.

As illustrated in FIG. 31, the intermediate electrode 725 may comprise a metallic or conductive tube, such as a radiopaque marker band composed of platinum alloy, platinum iridium alloy, or tungsten alloy, as non-limiting examples. In this way, the intermediate electrode 725 provides both the electrical path for the required sparks or arcing between electrodes as well as visible landmarks under x-ray fluoroscopy. Alternatively, the intermediate electrode could be made of a conductive material that is not as radiopaque, such as stainless steel or copper. The cavitation solution cavity 722 provides a lumen to add or refresh an appropriate cavitation solution, such as phosphate buffered saline solution, to the cavitation bubble chamber 720. The cavitation solution cavity 722 lumen may extend to the proximal end 719 of the medical device balloon catheter 700 to enable the user to add an appropriate cavitation solution to the cavitation bubble chamber 720, for example using a syringe filled with the cavitation solution attached to first cavitation solution fitting 717. An opening 723 connecting the cavitation bubble chamber 720 to the environment distal to the inflatable balloon 702, such as a hole, slit, or passage through the cavitation bubble chamber tube 721 and distal balloon tail 705 near or at the cavitation bubble chamber 720, may be added to facilitate adding an appropriate cavitation solution to the cavitation bubble chamber 720 or refresh the cavitation solution after arcing across the electrodes has occurred. The slit, hole, or passage 723 may be effective at venting, allowing entrapped gases and liquids to escape, and new cavitation solution to be added to the cavitation bubble chamber 720 by way of the cavitation solution cavity lumen 722. This is similar to flushing the catheter 700 with saline solution to remove entrapped air prior to a procedure and pre-loading the cavitation bubble chamber 725 with a cavitation solution.

Figure 33:
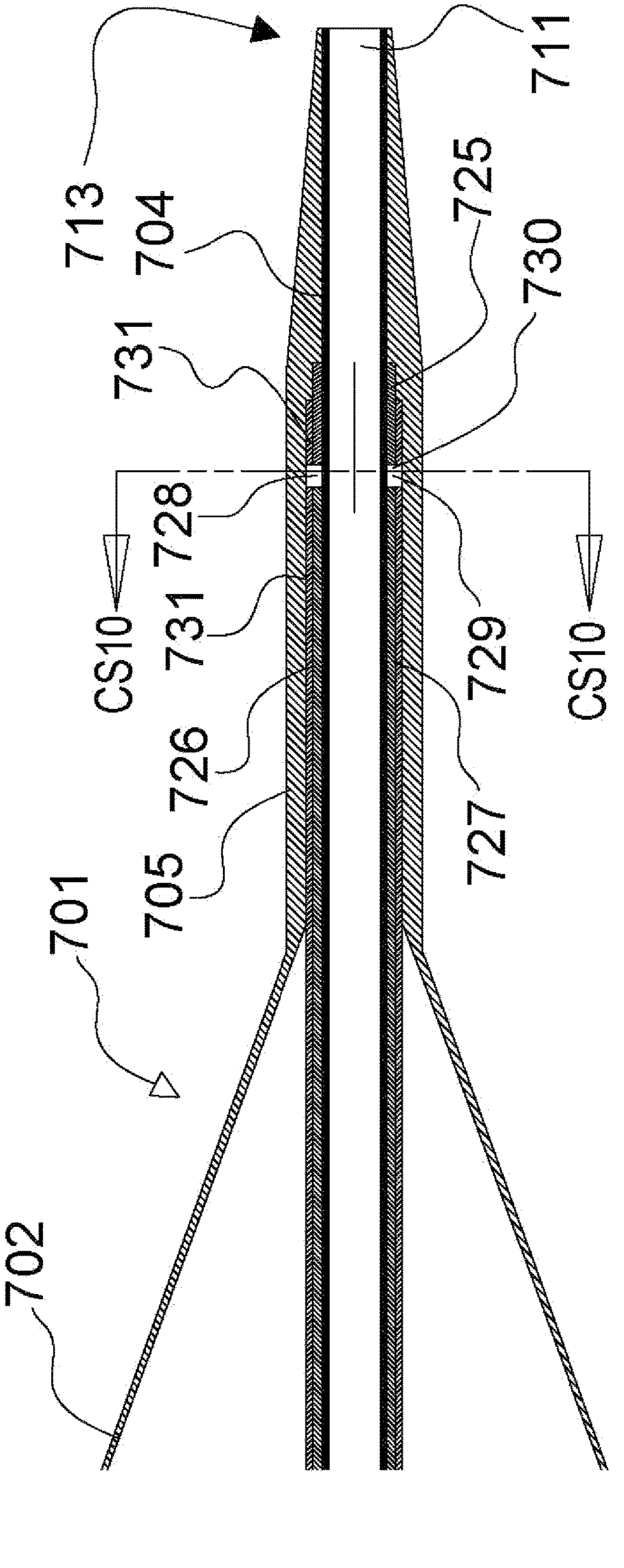
FIG. 33 is a partial schematic, longitudinal cross-sectional view of the distal end of a medical device balloon catheter according to the present disclosure.

FIG. 33 is partial schematic, longitudinal cross-sectional view of a medical device balloon catheter 701 according to an aspect of the present disclosure, showing a sectional view of a portion of medical device balloon catheter 701, including features at the distal end 713. Medical device catheter 701 is similar to medical device catheter 700 and includes a guidewire lumen 711 formed by a guidewire tube 704, which extends coaxially through a cavitation bubble chamber 730, an intermediate electrode 725, and the inflatable balloon 702. Cavitation bubble chamber 730 is formed by a polymer body 731. Medical device catheter 701 may also include a first electrode 726, a second electrode 727, and a two cavitation solution cavities or lumens 734 and 736 that extend from the cavitation bubble chamber 730 at the distal end 713 through the inflatable balloon 702 to a location outside the body of the patient, for example at the fitting assembly 715 near the proximal end 719 of medical device balloon catheter 701. For example, the first cavitation solution lumen 734 may be connected to the first cavitation solution fitting 717, and the second cavitation solution lumen 736 may be connected to the second cavitation solution fitting 718 such that a cavitation solution fluid can circulate from a syringe connected to the first cavitation solution fitting 717 through the first cavitation solution lumen 734, into the cavitation bubble chamber 730, and then back through the second cavitation solution lumen 736 to exit at the second cavitation solution fitting 718. The cavitation solution lumens 734 and 736 create fluid movement flow paths between the cavitation bubble chamber 730 and the proximal end 719 of the medical device balloon catheter 701, enabling fluid communication or fluid connection therebetween.

Cavitation solution cavities or lumens 734 and 736 are formed by cavitation solution tubes 735 and 737 also included in medical device balloon catheter 701. Medical device balloon catheter 701 may also include an inflatable balloon 702 that transitions to a distal balloon tail 705 that seals the distal end of the inflatable balloon 702 near the distal end 713. The distal balloon tail 705 may typically comprise of a polymer that is the same as the inflatable balloon 702 and forms the outer surface of this portion of the balloon catheter 701, where a similar or compatible polymer is typically formed into a taper at the distal end 713 where the distal exit of the guidewire lumen 711 is located. FIG. 33 also shows the electrode gap 728 between first electrode 726 and intermediate electrode 725 and electrode gap 729 between second electrode 727 and intermediate electrode 725.

Figure 34:
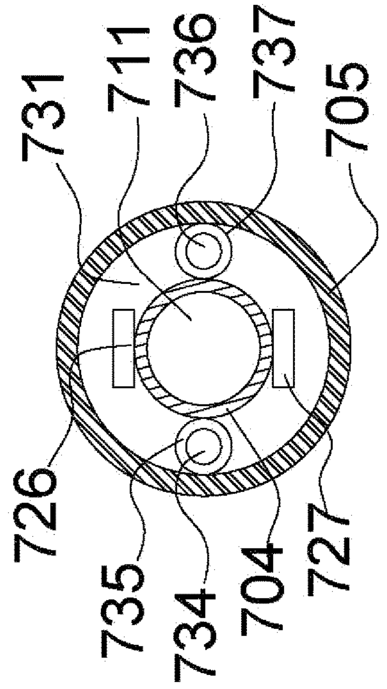
FIG. 34 is a partial schematic, transverse cross-sectional view CS10 of the medical device balloon catheter of FIG. 33.

FIG. 34 is a partial schematic, transverse cross-sectional view of medical device balloon catheter 701 at cavitation bubble chamber 730, or CS10 as illustrated in FIG. 33, showing guidewire tube 704, guidewire lumen 711, first electrode 726, second electrode 727, polymer body 731, distal balloon tail 705, and cavitation solution cavities or lumens 734 and 736 formed by cavitation solution tubes 735 and 737.

The electrode configuration of intermediate electrode 725, first electrode 726, and second electrode 727 shown in FIGS. 33 and 34 are the same as shown in FIGS. 31 and 32. The cavitation solution cavities or lumens 734 and 736 may extend to the proximal end 719 of the medical device catheter 701 to enable the user to add an appropriate cavitation solution to the cavitation bubble chamber 730. The cavitation solution lumens 734 and 736 provide a way to add or refresh an appropriate cavitation solution, such as phosphate buffered saline solution, to the cavitation bubble chamber 730. An advantage of two cavitation solution lumens, such as 734 and 736, is that one of the two lumens can be used to add fresh cavitation solution, while the other may allow cavitation solution liquid or gaseous components to be removed from the closed fluid circuit. For example, the user can pressurize first cavitation solution lumen 734 at the first cavitation solution fitting 717 at the proximal end 719 with a syringe filled with fresh cavitation solution, and discharge cavitation solution that has been circulated through the cavitation bubble chamber 730 by way of the second cavitation solution lumen 736 at the second cavitation solution fitting 718 at the proximal end 719. This will allow the cavitation solution that has been exposed to the high voltage electrical pulses and entrapped gases formed during the sparking events to exit the closed fluid circuit. First and second cavitation lumens 734 and 736 create a fluid flow path between the cavitation bubble chamber 730 and proximal end 719 of medical device balloon catheter 701, enabling fluid communication or fluid connection therebetween. This set of features and implementation can remove the need for an opening 723, such as a hole, slit, or passage, at the distal end 713 near the cavitation bubble chamber 720 to remove or add cavitation solution, such as described with reference to FIG. 31.

The distal ends of first electrode 726 and second electrode 727 terminate at the proximal end of, or within the cavitation bubble chambers 720 and 730. The intermediate electrode 725, which can be a tubular metallic band coaxial with the guidewire tube 704, is spaced a distance away from the distal end of the first and second electrodes, 726 and 727, at an appropriate distance to ensure consistent sparking across the electrode gaps, 728 and 729, and generation of the required shockwave energy. The spacing of this gap may typically range from between about 100 to about 500 microns.

Figure 35:
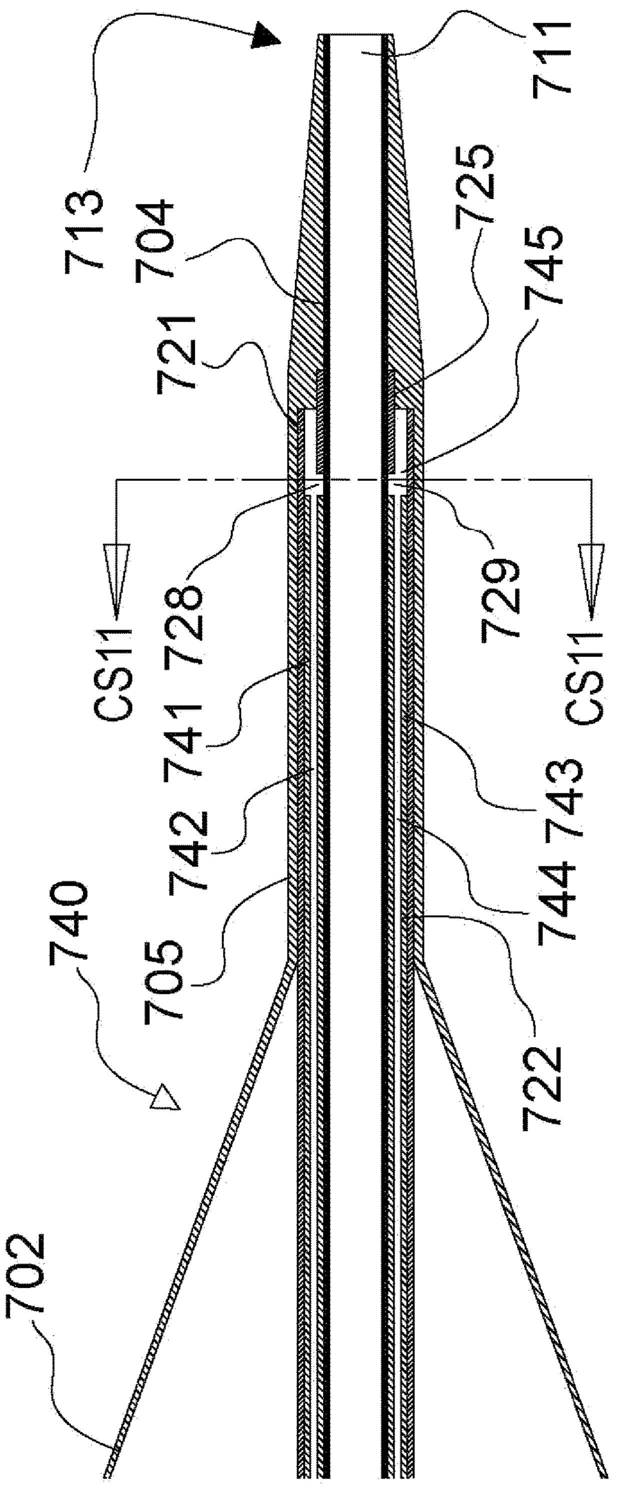
FIG. 35 is a partial schematic, longitudinal cross-sectional view of the distal end of a medical device balloon catheter according to the present disclosure.

FIG. 35 is partial schematic, longitudinal cross-sectional view of a medical device balloon catheter 740 according to an aspect of the present disclosure, showing a sectional view of a portion of medical device balloon catheter 740, including features at the distal end 713. Medical device catheter 740 is similar to medical device catheter 700 and 701 described previously, and includes a guidewire lumen 711 formed by a guidewire tube 704, which extends coaxially through a cavitation bubble chamber 745, an intermediate electrode 725, and the inflatable balloon 702. Cavitation bubble chamber 745 is formed by a tube, cavitation bubble chamber tube 721. Medical device catheter 740 may also include a first electrode tube 741 and a second electrode tube 743. First electrode 741 and second electrode 743 also form two cavitation solution cavities or lumens, a first cavitation solution cavity or lumen 742 and a second cavitation solution cavity or lumen 744 that extend from the cavitation bubble chamber 745 at the distal end 713 through the inflatable balloon 702 to a location outside the body of the patient, for example at the fitting assembly 715 near the proximal end 719 of medical device balloon catheter 740. The first cavitation solution lumen 742 may be fluidly connected to cavitation solution fitting 717 and the second cavitation solution lumen 744 may be fluidly connected to cavitation solution fitting 718. Cavitation solution cavities or lumens 742 and 744 are formed in part by conductive tubes of oval cross-section that also serve as first electrode 741 and second electrode 743. Medical device balloon catheter 740 may also include an inflatable balloon 702 that transitions to a distal balloon tail 705 that seals the distal end of the inflatable balloon 702 near the distal end 713. The distal balloon tail 705 may typically comprise of a polymer that is the same as the inflatable balloon 702 and forms the outer surface of this portion of the balloon catheter 740, where a similar or compatible polymer is typically formed into a taper at the distal end 713 where the distal exit of the guidewire lumen 711 is located. FIG. 35 also shows the electrode gap 728 between first electrode 741 and intermediate electrode 725 and electrode gap 729 between second electrode 743 and intermediate electrode 725.

Figure 36:
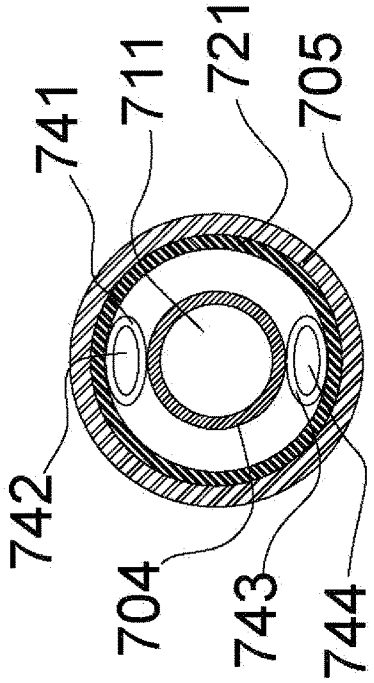
FIG. 36 is a partial schematic, transverse cross-sectional view CS11 of the medical device balloon catheter of FIG. 35.

FIG. 36 is a partial schematic, transverse cross-sectional view of medical device catheter 740 at cavitation bubble chamber 745, or CS11 as illustrated in FIG. 35, showing guidewire tube 704, guidewire lumen 711, first electrode tube 741, second electrode tube 743, cavitation bubble tube 721, distal balloon tail 705, and cavitation solution cavities or lumens 742 and 744 formed by electrode tubes 741 and 743.

In an alternate configuration of medical device catheter 740 illustrated in FIG. 35 and FIG. 36, the tubes 741 and 743 may suitably comprise a conductive material, such as copper or stainless steel, where the tubes 741 and 743 may fulfill dual functions of serving as the electrodes and creating the cavitation solution lumens 742 and 744. This is advantageous because combining both functions into a single feature, i.e. a set of conductive electrode tubes 741 and 743 that both fluidly and electrically connect the cavitation bubble chamber 745 to the proximal end 719 of medical device balloon catheter 740 outside the body of the patient, eliminates the need for separate electrodes and lumens for the cavitation solution, thus enabling a smaller profile medical device catheter 740. Cavitation solution lumens 742 and 744 create a fluid flow path between the cavitation bubble chamber 745 and proximal end 719 of medical device balloon catheter 740, enabling fluid communication or fluid connection therebetween, in the same way cavitation solution lumens 734 and 736 function in reference to FIG. 33 and FIG. 34 describing medical device balloon catheter 701. Electrode tubes 741 and 743 are shown as an oval shape in cross-section instead of round such that the profile of the medical device catheter can be further decreased, however, round tubes may also be suitable depending on the needs of the medical device and procedure.

Figure 37:
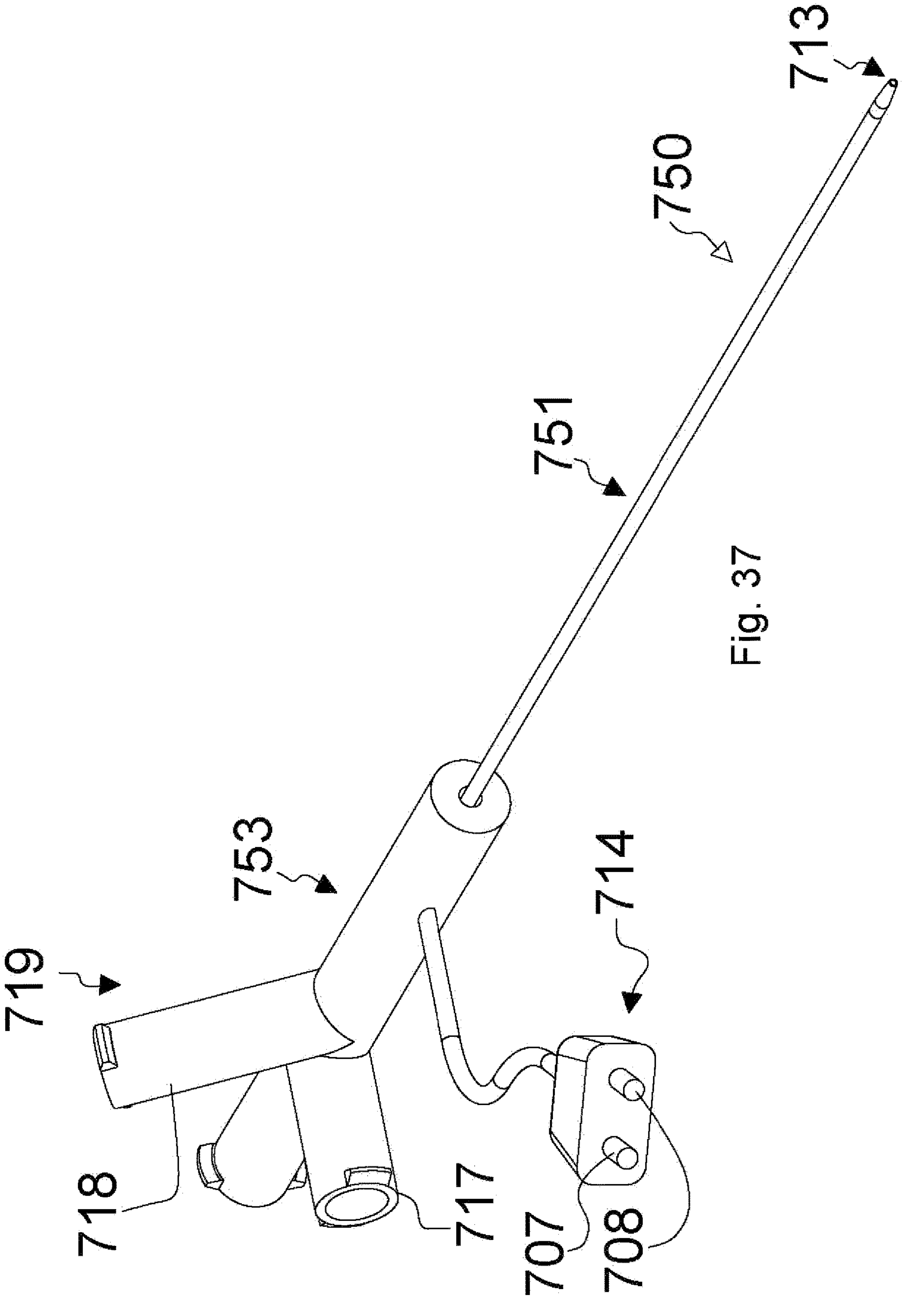
FIG. 37 is a schematic, perspective view of a medical device catheter according to the present disclosure.

In another aspect, a catheter having unitary design is provided without a balloon mechanism or features, but with IVL features such as described previously. FIG. 37 illustrates the features of medical device catheter 750 which includes a distal end 713 and proximal end 719 with a catheter shaft 751 therebetween. Medical device catheter 750 also includes a fitting assembly 753 near the proximal end 719 of medical device catheter 700. The catheter shaft 751 is typically a long tube comprising one or more lumens and one or more electrical conductors. Fitting assembly 753 also includes a first cavitation solution fitting 717, and a second cavitation solution fitting 718 that are connected a first cavitation solution lumen 742 or cavity and a second cavitation solution lumen 744 or cavity which creates fluid flow paths, or connections, extending between the cavitation bubble chamber 745 and first and second cavitation solution fittings 717 and 718. Fitting assembly 753 also includes an electrical connector 714 that includes at least two electrical connector pins, a first electrical connector pin 707 and a second electrical connector pin 708. Electrical connector 714 and the first and second electrical connector pins 707 and 708 respectively are adapted to electrically couple, or connect, a high voltage pulse generator to electrode pairs 741 and 743 in the cavitation bubble chamber 745.

Figure 38:
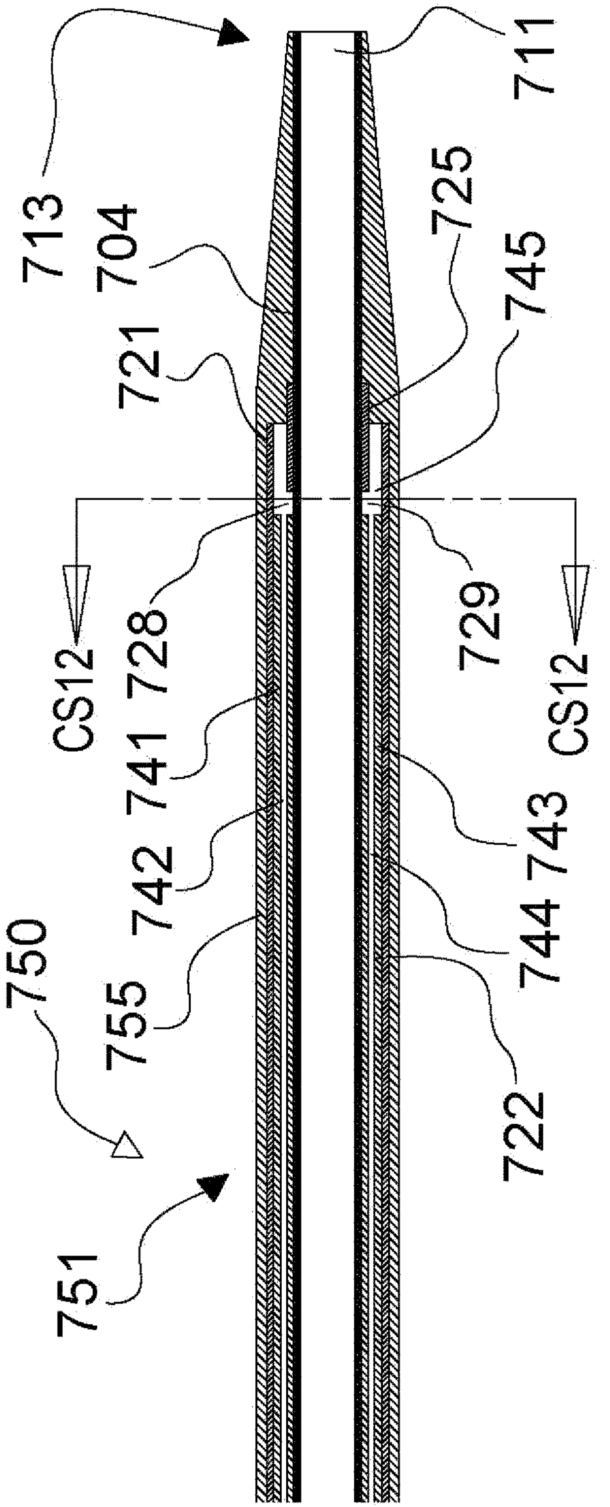
FIG. 38 is a partial schematic, longitudinal cross-sectional view of the distal end of a medical device catheter according to the present disclosure.
Figure 39:
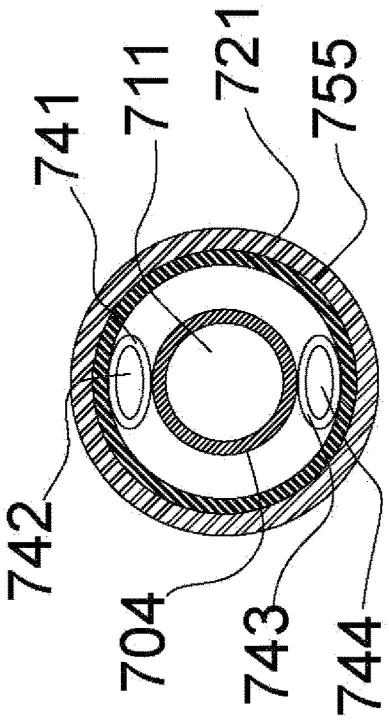
FIG. 39 is a partial schematic, transverse cross-sectional view CS12 of the medical device catheter of FIG. 38.

The medical device catheter 750 of FIGS. 37-39 is a catheter that may also be conceptualized as an integrated, unitary or "one-piece" design version of the assembled modular catheter system, comprising an intravascular lithotripsy (IVL) adapter attached to a medical device catheter. Instead of two modules attached together to combine the features of a catheter with a cavitation bubble chamber at the distal end to deliver shockwave energy, medical device catheter 750 may integrate the IVL features in a "non-modular" or unitary design. The distal end 713 of medical device catheter 750 is intended to be inserted into a body lumen, such as a vessel, artery, vein, or duct to deliver the shockwave energy. The proximal end 719 is intended to stay outside the body of the patient and is where the user interfaces with the medical device catheter 750, such as connecting a high voltage pulse generator, and circulating cavitation solution to the distal end 713.

FIG. 38 is partial schematic, longitudinal cross-sectional view of a medical device catheter 750 according to an aspect of the present disclosure, showing a sectional view of a portion of medical device catheter 750, including features at the distal end 713. Medical device catheter 750 is similar to medical device catheter 740 described previously, and includes a guidewire lumen 711 formed by a guidewire tube 704, which extends coaxially through a cavitation bubble chamber 745, an intermediate electrode 725, but excludes the inflatable balloon 702 features. Catheter shaft 751 includes lumens and conductors connecting the distal end 713 and cavitation bubble chamber 745 to the proximal end 719 therebetween. Cavitation bubble chamber 745 is formed by a tube, cavitation bubble chamber tube 721. Medical device catheter 750 may also include a first electrode tube 741 and a second electrode tube 743. First electrode 741 and second electrode 743 also form two cavitation solution cavities or lumens, a first cavitation solution cavity or lumen 742 and a second cavitation solution cavity or lumen 744 that extend from the cavitation bubble chamber 745 at the distal end 713 to a location outside the body of the patient, for example at the fitting assembly 715 near the proximal end 719 of medical device catheter 740. The first cavitation solution lumen 742 may be fluidly connected to cavitation solution fitting 717 and the second cavitation solution lumen 744 may be connected to cavitation solution fitting 718. Cavitation solution cavities or lumens 742 and 744 are formed in part by conductive tubes of oval cross-section that also serve as first electrode 741 and second electrode 743. The catheter shaft 751 may typically comprise of a polymer covering 755 that forms the outer surface of this portion of the catheter 750, where a similar or compatible polymer is typically formed into a taper at the distal end 713 where the distal exit of the guidewire lumen 711 is located. FIG. 38 also shows the electrode gap 728 between first electrode 741 and intermediate electrode 725 and electrode gap 729 between second electrode 743 and intermediate electrode 725.

FIG. 39 is a partial schematic, transverse cross-sectional view of medical device catheter 750 at cavitation bubble chamber 745, or CS12 as illustrated in FIG. 38, showing guidewire tube 704, guidewire lumen 711, first electrode tube 741, second electrode tube 743, cavitation bubble tube 721, polymer covering 755, and cavitation solution cavities or lumens 742 and 744 formed by electrode tubes 741 and 743.

In an alternate configuration of medical device catheter 750 illustrated in FIG. 38 and FIG. 39, the tubes 741 and 743 may suitably comprise a conductive material, such as copper or stainless steel, where the tubes 741 and 743 may fulfill dual functions of serving as the electrodes and creating the cavitation solution lumens 742 and 744. This is advantageous because combining both functions into a single feature, i.e. a set of conductive electrode tubes 741 and 743 that both fluidly and electrically connect the cavitation bubble chamber 745 to the proximal end 719 of medical device catheter 750 outside the body of the patient, eliminates the need for separate electrodes and lumens for the cavitation solution, thus enabling a smaller profile medical device catheter 750. Cavitation solution lumens 742 and 744 create a fluid flow path between the cavitation bubble chamber 745 and proximal end 719 of medical device catheter 750, enabling fluid communication or fluid connection therebetween, in the same way as cavitation solution lumens 734 and 736 function in reference to FIG. 33 and FIG. 34 describing medical device balloon catheter 701. Electrode tubes 741 and 743 are shown as an oval shape in cross-section instead of round such that the profile of the medical device catheter can be further decreased, however, round tubes may also be suitable depending on the needs of the medical device and procedure.

Figure 40:
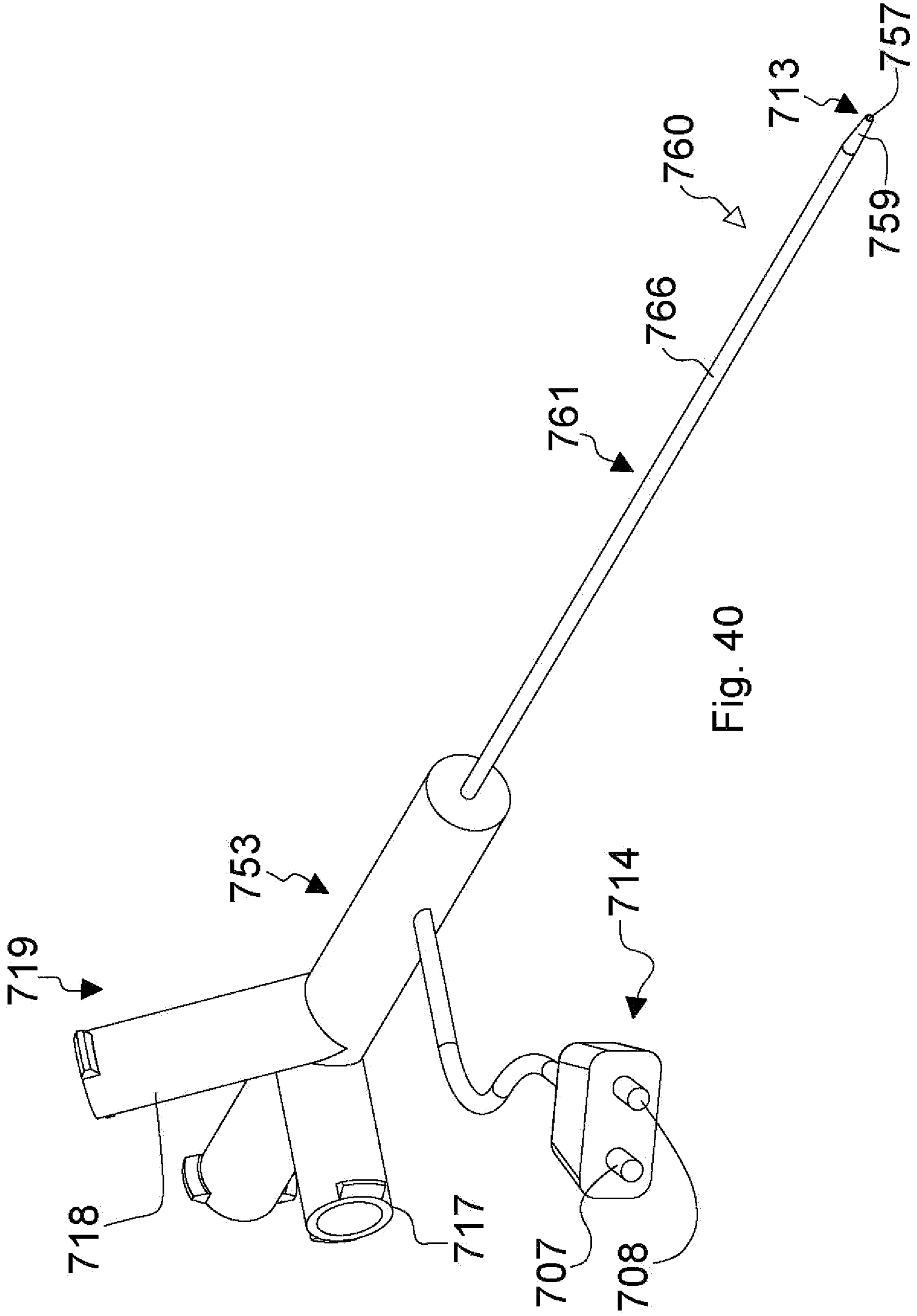
FIG. 40 is a schematic, perspective view of a medical device catheter according to the present disclosure.

In another aspect of the present disclosure, a medical device catheter having unitary design is provided without a balloon mechanism or its features, but with IVL features such as described previously. FIG. 40 illustrates the features of medical device catheter 760 which includes a distal end 713 and proximal end 719 with a catheter shaft 761 therebetween. Medical device catheter 760 also includes a proximal fitting assembly 753 near the proximal end 719 of medical device catheter 760. Catheter shaft 761 is typically a long tube comprising one or more lumens and one or more electrical conductors. Fitting assembly 753 also includes a first cavitation solution fitting 717, and a second cavitation solution fitting 718 that are connected to a first cavitation solution lumen or cavity 763 and a second cavitation solution lumen or cavity 767 which creates fluid flow paths, or connections, extending between the cavitation bubble chamber 765 and first and second cavitation solution fittings, 717 and 718, as will be described in further detail below in reference to FIGS. 41-43, for example. Fitting assembly 753 also includes an electrical connector 714 that includes at least two electrical connector pins, a first electrical connector pin 707 and a second electrical connector pin 708. Electrical connector 714 and the first and second electrical connector pins 707 and 708 respectively are adapted to electrically couple, or connect, a high voltage pulse generator to electrode pairs in the cavitation bubble chamber described further below in reference to FIGS. 41-43, for example. Catheter shaft 761 includes an outer tube 766 that forms at least a portion of the cavitation bubble chamber 765 and at least a portion of second cavitation solution lumen or cavity 767 to create the fluid flow path extending between the cavitation bubble chamber 765 and second cavitation solution fitting 718. In the region of the cavitation bubble chamber 765, the cavity or lumen that forms the second cavitation solution lumen or cavity 767 and cavitation bubble chamber 765 are the same. Catheter shaft 761 also includes a tapered transition 759 to a smaller diameter at the distal end 713 to facilitate the use of a guidewire by way of a guidewire lumen 757.

Figure 41:
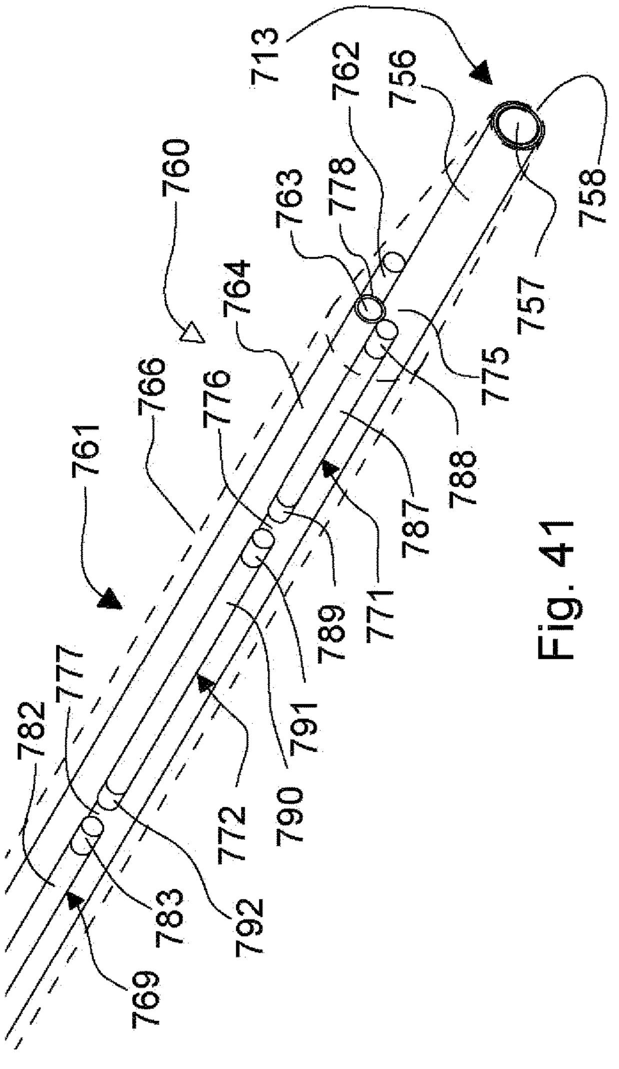
FIG. 41 is an enlarged detailed view of FIG. 40, showing part of a distal portion of the catheter and the internal features and elements of a distal portion of the adapter.

FIG. 41 is an enlarged detailed view of the distal portion of medical device catheter 760 and catheter shaft 761, illustrating the distal end 713 with the outer tube 766 and tapered transition 759 hidden as dotted lines such that the internal features of distal end 713 of catheter shaft 761 can be illustrated. Medical device catheter 760 and catheter shaft 761 include a guidewire tube 756 which has a distal end 758 and a lumen 757 sized to accommodate a guidewire for use during an interventional procedure. Medical device catheter 760 and catheter shaft 761 also include first cavitation solution tube 764 that has a distal end 778 and forms a first cavitation solution lumen or cavity 763. Catheter shaft 761 also includes a series of electrodes for the purposes of creating a series of shockwave producing sparks, arcs, or plasma channels across the electrode gaps formed therein. FIG. 41 illustrates a second powered electrode 769, which includes an insulated covering or coating 782 such that an exposed or uninsulated portion 783 is at the distal end of electrode 769. Similarly, a fourth intermediate electrode 772 is illustrated and includes an insulated covering or coating 790 such that the proximal end 792 and distal end 791 are exposed or uninsulated. A third intermediate electrode 771 is illustrated and includes an insulated covering or coating 787 such that the proximal end 789 and distal end 788 are exposed or uninsulated. A second intermediate electrode 762 is illustrated and is positioned with a portion distal to the distal end 778 of the lumen 763 of first cavitation solution tube 764. As illustrated, the positioning of the second intermediate electrode 762 is such that an insulated covering is not required. FIG. 41 illustrates third electrode gap 775 formed between the second intermediate electrode 762 and the distal uninsulated end 788 of third intermediate electrode 771, fourth electrode gap 776 formed between the proximal uninsulated end 789 of third intermediate electrode 771 and distal uninsulated end 791 of fourth intermediate electrode 772, and fifth electrode gap 777 formed between the proximal uninsulated end 792 of fourth intermediate electrode 772 and distal uninsulated end 783 of second powered electrode 769. The first electrode gap 773 and second electrode gap 774 are shown and described with respect to FIG. 44 below.

Figure 42:
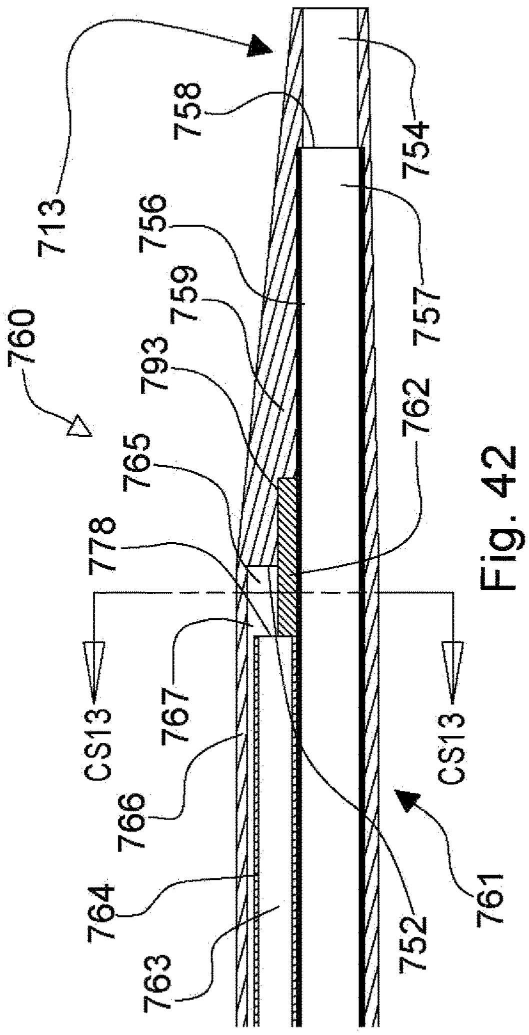
FIG. 42 is a partial schematic, longitudinal cross-sectional view of the distal end of a medical device catheter according to the present disclosure.

FIG. 42 is partial schematic, longitudinal cross-sectional view of a medical device catheter 760 according to an aspect of the present disclosure, showing a sectional view of a portion of medical device catheter 760 and catheter shaft 761, including the features at the distal end 713 as well as second intermediate electrode 762. Catheter shaft 761 includes a guidewire lumen 757 formed by a guidewire tube 756 and a cavity 754 within a tapered transition 759 to a smaller diameter at distal end 713, where cavity 754 is distal to the distal end 758 of guidewire tube 756. Guidewire tube 756 extends through a cavitation bubble chamber 765 and at least a portion of a second cavitation solution lumen or cavity 767. Cavitation bubble chamber 765 and second cavitation solution lumen or cavity 767 are formed by outer tube 766. Within outer tube 766 and cavitation bubble chamber 765 is the distal end 778 of first cavitation solution lumen or cavity 763 formed in part by first cavitation solution tube 764.

Figure 43A:
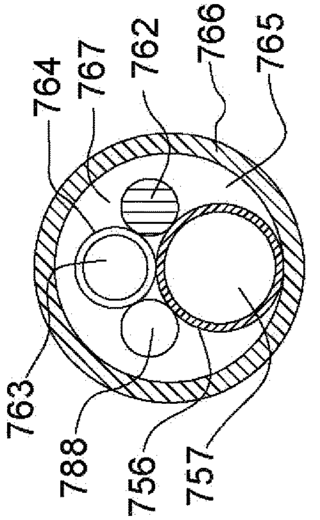
FIG. 43*a* is a partial schematic, transverse cross-sectional view CS13 of the medical device catheter of FIG. 42.

FIG. 43*a* is a partial schematic, transverse cross-sectional view of medical device catheter 760 through a portion of cavitation bubble chamber 765, or CS13 as illustrated in FIG. 42, and showing guidewire tube 756, guidewire lumen 757, uninsulated distal end 788 of third intermediate electrode 771 (shown in FIG. 41), second intermediate electrode 762, outer tube 766, cavitation bubble chamber 765, second cavitation solution lumen or cavity 767, and first cavitation solution lumen or cavity 763 formed by a first cavitation solution tube 764.

Figure 43B:
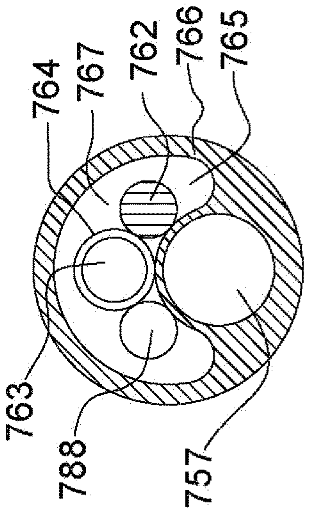
FIG. 43*b* is a partial schematic, transverse cross-sectional view CS13 of the medical device catheter of FIG. 42.

FIG. 43*b* is a partial schematic, transverse cross-sectional view of medical device catheter 760 through a portion of cavitation bubble chamber 765, or CS13 as illustrated in FIG. 42, and showing guidewire lumen 757, uninsulated distal end 788 of third intermediate electrode 771 (shown in FIG. 41), second intermediate electrode 762, outer tube 766, cavitation bubble chamber 765, second cavitation solution lumen or cavity 767, and first cavitation solution lumen or cavity 763 formed by a first cavitation solution tube 764. In this illustration, outer tube 766 is a dual lumen extrusion, one lumen forms the guidewire lumen 757 and the other lumen forms the cavitation bubble chamber 765 and second cavitation solution lumen or cavity 767.

Figure 44:
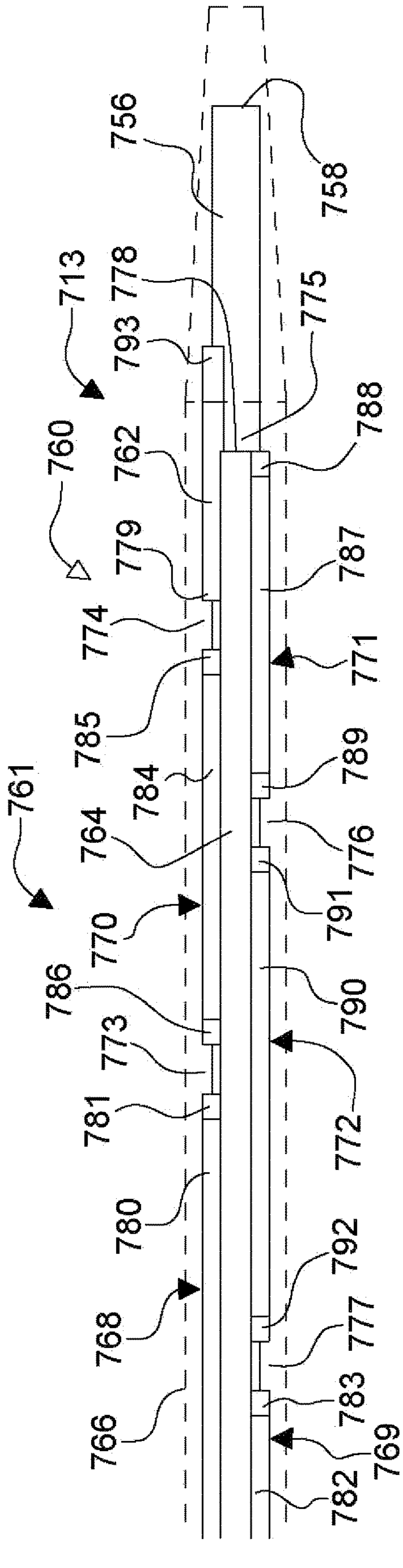
FIG. 44 is a partial schematic, longitudinal top view of the distal end of a medical device catheter according to the present disclosure, showing the internal features and elements of a distal portion of the medical device catheter.

FIG. 44 is a partial schematic longitudinal top view of the distal end 713 of medical device catheter 760 and catheter shaft 761 shown with reference to FIGS. 40-43, with the outer tube 766 and tapered transition 759 hidden as dotted lines such that the internal features of distal end 713 of catheter shaft 761, and electrode configuration can be further illustrated. FIG. 44 can be conceptualized as a top view projection where, for reference, FIG. 42 is a side cross-sectional view projection. With reference to FIG. 44 in addition to the shared features described with reference to FIGS. 40-43 previously, medical device catheter 760 and catheter shaft 761 include a guidewire tube 756 which has a distal end 758 and a lumen 757 sized to accommodate a guidewire for use during an interventional procedure. Medical device catheter 760 and catheter shaft 761 also include first cavitation solution tube 764 that has a distal end 778 and forms a first cavitation solution lumen or cavity 763. Catheter shaft 761 also includes a series of electrodes for the purposes of creating a series of shockwave producing sparks, arcs, or plasma channels across the electrode gaps formed therein. FIG. 44 illustrates a first powered electrode 768, which includes an insulated covering or coating 780 such than an exposed or uninsulated portion 781 is at the distal end of the electrode 768. Similarly, a first intermediate electrode 770 is illustrated and includes an insulated covering or coating 784 such that the proximal end 786 and distal end 785 are exposed or uninsulated. A second intermediate electrode 762 is illustrated and is positioned with a distal portion 793 distal to the distal end 778 of the lumen 763 (see FIGS. 41-43) of first cavitation solution tube 764 and distal to the distal boundary 752 of cavitation bubble chamber 765. As illustrated, the second intermediate electrode 762 has an uninsulated proximal end 779 and the positioning is such that an insulated covering is not required. A third intermediate electrode 771 is illustrated and includes an insulated covering or coating 787 such that the proximal end 789 and distal end 788 are exposed or uninsulated. A fourth intermediate electrode 772 is illustrated and includes an insulated covering or coating 790 such that the proximal end 792 and distal end 791 are exposed or uninsulated. A second powered electrode 769 includes an insulated covering or coating 782 such that an exposed or uninsulated portion 783 is at the distal end of electrode 769.

FIG. 44 illustrates first electrode gap 773 formed between the distal end of the first powered electrode 768 and the proximal uninsulated end 786 of first intermediate electrode 770, second electrode gap 774 formed between the distal uninsulated end 785 of the first intermediate electrode 770 and the proximal uninsulated end 779 of second intermediate electrode 762, third electrode gap 775 formed between the second intermediate electrode 762 and the distal uninsulated end 788 of third intermediate electrode 771, fourth electrode gap 776 formed between the proximal uninsulated end 789 of third intermediate electrode 771 and distal uninsulated end 791 of fourth intermediate electrode 772, and fifth electrode gap 777 formed between the proximal uninsulated end 792 of fourth intermediate electrode 772 and distal uninsulated end 783 of second powered electrode 769.

The medical device catheter 760 of FIGS. 40-44 is a catheter that may also be conceptualized as an integrated, unitary or "one-piece" design version of the assembled modular catheter system, comprising an intravascular lithotripsy (IVL) adapter attached to a medical device catheter. Instead of two modules attached together to combine the features of a catheter with a cavitation bubble chamber at the distal end to deliver shockwave energy, medical device catheter 760 may integrate the IVL features in a "non-modular" or unitary design. The distal end 713 of medical device catheter 760 is intended to be inserted into a body lumen, such as a vessel, artery, vein, or duct to deliver shockwave energy. The proximal end 719 is intended to stay outside the body of the patient and is where the user interfaces with the medical device catheter 760, such as connecting a high voltage pulse generator, and circulating cavitation solution to the distal end 713.

As shown in FIGS. 40-44, a cavitation bubble chamber 765 is formed by an outer tube 766 at the distal end 713 of medical device catheter 760 and catheter shaft 761. In one aspect, cavitation bubble chamber 765 may house within it two (2) powered electrodes, a first powered electrode 768 (shown with respect to FIG. 44) and a second powered electrode 769; four (4) intermediate electrodes, including a first intermediate electrode 770, a second intermediate electrode 762, a third intermediate electrode 771, and a fourth intermediate electrode 772; and a first cavitation solution tube 764 forming a first cavitation solution lumen 763, for example. The electrodes may be positioned along the length of the cavitation bubble chamber 765 to create five (5) electrode gaps, such as first electrode gap 773, second electrode gap 774, third electrode gap 775, fourth electrode gap 776 and fifth electrode gap 777. In this example, a second cavitation solution lumen or cavity 767 is formed by the outer tube 766 such that a cavitation solution, such as saline solution, can be circulated from a first cavitation solution fitting 717 through the first cavitation solution lumen 763, through the cavitation bubble chamber 765 and the second cavitation solution lumen 767 exiting by way of a second cavitation solution fitting 718. In this way, the cavitation solution can be circulated through the cavitation bubble chamber 765 on a continuous or semi-continuous basis during the intravascular lithotripsy process. In alternate examples, the guidewire tube 756 may exit the catheter shaft 761 at a location between the distal end 713 and a proximal fitting assembly 753, which would be useful in a rapid exchange (RX) catheter version. This type of rapid exchange (RX) example is illustrated in rapid exchange (RX) intravascular lithotripsy (IVL) adapter 510 as shown with reference to FIGS. 17-20. In this rapid exchange (RX) example, the guidewire 516 exits at a proximal position 515 to the proximal end 527 of cavitation bubble chamber such that the cavitation solution may be returned by way of lumen 463 of the central tube 462, where lumen 463 is fluidly connected a cavitation bubble chamber such as illustrated by cavitation bubble chamber 765.

In the example illustrated in FIGS. 40-44, when the first powered electrode 768 is connected to a positive channel of a high voltage pulse generator 457 (such as shown and described with respect to FIG. 22) and the second powered electrode 769 is connected to a negative channel of the pulse generator 457, and a sufficiently high voltage pulse is applied between the powered electrodes, then provided the positioning of the electrode gaps are strategically staggered, as illustrated, such that electrical arcing or sparking will occur only at the electrode gaps to complete the high voltage pulse circuit, the electrical arcing or sparking across each electrode gap will create an individual shockwave and may also create an associated cavitation bubble. The continuous or semi-continuous circulation of cavitation solution as described would facilitate sufficient removal of the generated cavitation bubbles to allow subsequent arcing and shockwave generation at a frequency required for the intravascular lithotripsy process. For the purposes of intravascular lithotripsy, shockwave generation frequencies of 1 to 10 hertz would be suitable.

In the example illustrated in FIG. 40-44, the first powered electrode 768, the second powered electrode 769, first intermediate electrode 770, the third intermediate electrode 771, and the fourth intermediate electrode 772 include electrically insulated coverings or coatings 780, 782, 784, 787, and 790 respectively such that only selective portions of the electrodes are uninsulated or exposed, in this case the distal end 781 of first powered electrode 768, the proximal end 786 and distal end 785 of the first intermediate electrode 770, the distal end 788 and proximal end 789 of third intermediate electrode 771, the distal end 791 and proximal end 792 of fourth intermediate electrode 772, and distal end 783 of second powered electrode 769. In this example, the second intermediate electrode 762 is the most electrically positive distal electrode in the electrode chain such that it is positioned to only allow electrical arcing at electrode gaps 774 and 775 without requiring selective electrically insulated coverings or coatings. Further, the uninsulated portions of the other electrodes are positioned to be strategically staggered such that electrical arcing will only occur at electrode gaps 773, 776, and 777. The electrodes can be made of electrically conductive materials for example graphite or metals such as copper, stainless steel, tungsten, platinum, platinum alloys, nitinol, or other metal alloys. Examples of insulative coatings or coverings include enamel, polyurethane, polyamide-imide, and polyimide. Examples of suitable electrically conductive wire for electrodes include magnet wire, which includes a copper core with a polymer coating as an insulated covering. The electrodes are shown as round wire but could also be flat wire, or stranded wire, small or fine wire bundled together to form a conductor, as non-limiting examples.

In the example illustrated in FIG. 40-44, the distal end 778 of the first cavitation solution lumen 763 is near or at the distal end of the cavitation bubble chamber 765 such that filling the cavitation bubble chamber 765 with a cavitation solution through the first cavitation solution lumen 763 would help facilitate removing any generated cavitation bubbles by evacuating the cavitation solution through the second cavitation solution lumen 767 and any lumens proximal and fluidly connected to second cavitation solution lumen 767.

An advantage of the electrode configuration illustrated in FIG. 44 is that the electrode gaps are distributed along the length of the cavitation bubble chamber 765 and on either side of the catheter shaft 761 for a more evenly distributed shockwave generation.

In an alternative configuration of the example illustrated in FIGS. 40-44, the uninsulated distal end 788 of third intermediate electrode 771 can extend distally past the distal boundary 752 of cavitation bubble chamber 765 in a manner similar to second intermediate electrode 762.

Figure 45:
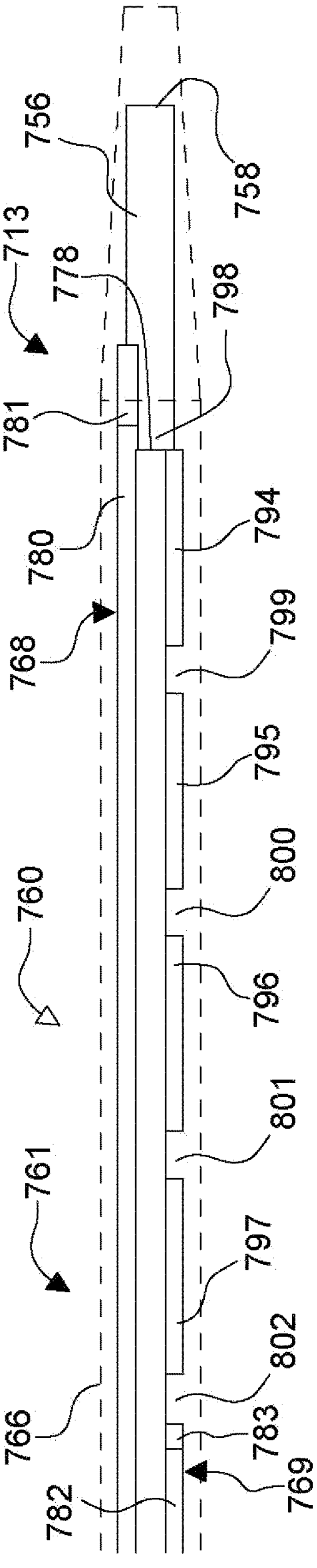
FIG. 45 is a partial schematic, longitudinal top view of the distal end of a medical device catheter according to the present disclosure, showing the internal features and elements of a distal portion of the medical device catheter.

Including shared features described with reference to FIGS. 40-44 previously, FIG. 45 is a partial schematic longitudinal top view of the distal end 713 of medical device catheter 760 and catheter shaft 761, with the outer tube 766 and tapered transition 759 hidden as dotted lines such that the internal features of a cavitation bubble chamber 765, a portion of a second cavitation solution lumen 767, and an alternate electrode configuration can be illustrated. In other words, FIG. 45 is similar to FIG. 44 but showing an example of an alternative electrode configuration.

FIG. 45 illustrates a first powered electrode 768, which includes an insulated covering or coating 780 such than an exposed or uninsulated portion 781 is at the distal end of the electrode 768, a first intermediate electrode 794, a second intermediate electrode 795, a third intermediate electrode 796, a fourth intermediate electrode 797, and a second powered electrode 769, which includes an insulated covering or coating 782 such that an exposed or uninsulated portion 783 is at the distal end of electrode 769. FIG. 45 illustrates first electrode gap 798 formed between the distal end 781 of the first powered electrode 768 and the distal end of first intermediate electrode 794, second electrode gap 799 formed between the proximal end of the first intermediate electrode 794 and the distal end of second intermediate electrode 795, third electrode gap 800 formed between the proximal end of the second intermediate electrode 795 and the distal end of third intermediate electrode 796, fourth electrode gap 801 formed between the proximal end of third intermediate electrode 796 and distal end of fourth intermediate electrode 797, and fifth electrode gap 802 formed between the proximal end of fourth intermediate electrode 797 and distal uninsulated end 783 of second powered electrode 769.

The electrode configuration example shown in FIG. 45 can be conceptualized as a chain of electrodes and electrode gaps where the first powered electrode 768 extends near the distal end of the cavitation bubble chamber 765 to create a first electrode gap 798 starting with the distal end of the first intermediate electrode 794, and subsequent electrode gaps (i.e., second electrode gap 799, third electrode gap 800, fourth electrode gap 801 and fifth electrode gap 802) are created by the subsequent adjacent electrodes in the electrode chain, terminating with the second powered electrode 769 located proximally. As illustrated, the uninsulated distal end 781 of first powered electrode 768 extends distally past the distal boundary 752 of cavitation bubble chamber 765.

In the electrode configuration example shown in FIG. 45, when the first powered electrode 768 is connected to a positive channel of a high voltage pulse generator 457 (such as shown and described with respect to FIG. 22) and the second powered electrode 769 is connected to a negative channel of the pulse generator 457, and a sufficiently high voltage pulse is applied between the powered electrodes, then electrical arcing or sparking across each electrode gap will create individual shockwaves and may also create an associated cavitation bubble. An advantage of this electrode chain configuration is that the intermediate electrodes 794, 795, 796, 797 do not require an insulative coating or covering. Another advantage of this electrode chain configuration is that the first powered electrode 768 could be formed by a conductive tube, similar to first electrode tube 741 such as described with reference to FIG. 38 and FIG. 39, such that it would function both as the first powered electrode 768 and a first cavitation solution lumen 763.

In the example shown in FIG. 45, the intermediate electrodes are represented as round wires of a given length, however, the intermediate electrodes may also comprise ring electrodes similar to intermediate electrode 725 or tubular electrode elements, such as tubular electrode elements 541 describe previously. In this alternative example, the intermediate ring electrodes or tubular electrodes, similar to 725 or 541 described previously, would preferably be coaxial with either the guidewire lumen 757 and guidewire tube 756, or coaxial with the first cavitation solution lumen or cavity 763 and first cavitation solution tube 764. There may be advantages to a combination of intermediate electrodes coaxial with guidewire tube 756 and first cavitation solution tube 764, for example, the distal most intermediate electrode could be coaxial with the guidewire tube 756 and comprised of a radiopaque material such as tungsten or a platinum alloy to provide a marker of location under fluoroscopy during an interventional procedure, and the more proximal intermediate electrodes could be smaller and coaxial with the first cavitation solution tube 764 and comprised of a material that is less expensive such as stainless steel. Intermediate electrodes may suitably comprise partial rings, such as a semicircular cylinders, or even flat wire that is coiled in a spiral to facilitate positioning the intermediate electrodes during manufacturing.

Figure 46:
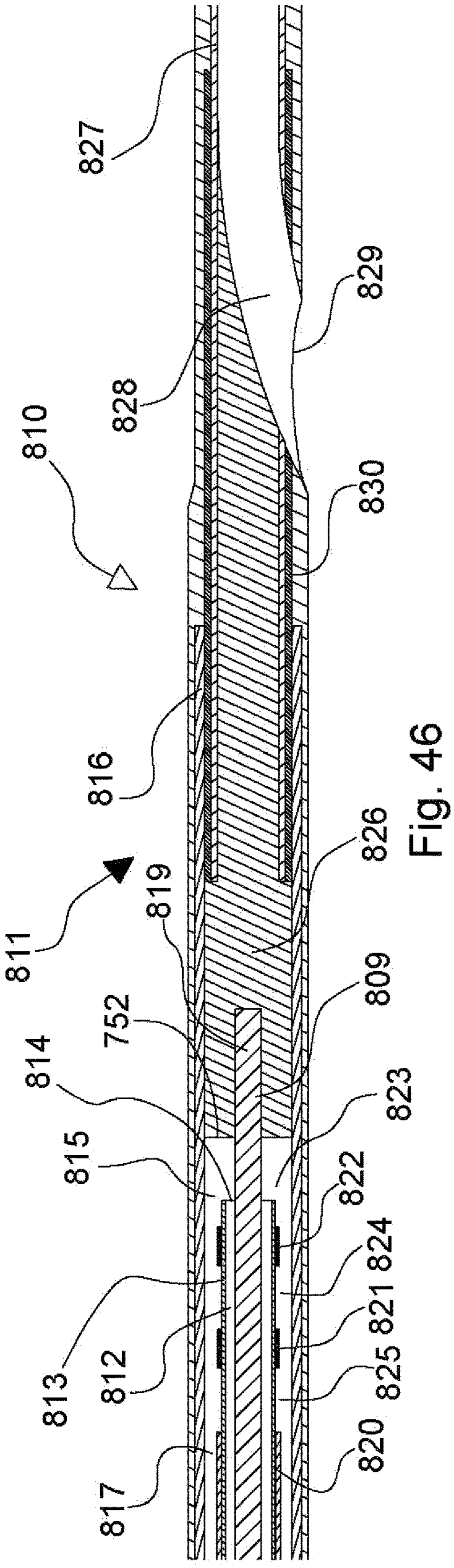
FIG. 46 is a partial schematic, longitudinal cross-sectional view of a cavitation bubble chamber and proximal portion of a guidewire lumen of a medical device catheter according to the present disclosure.

FIG. 46 is partial schematic, longitudinal cross-sectional view of a medical device catheter 810 according to an aspect of the present disclosure, showing a sectional view of a portion of medical device catheter 810 and catheter shaft 811, illustrating features of a cavitation bubble chamber 815, a first tube 813 forming a first cavitation solution lumen 812, a distal opening 814 of first cavitation solution lumen 812, a second cavitation solution lumen 817, a tube 816 forming cavitation bubble chamber 815 and at least a portion of second cavitation solution lumen 817, a first powered electrode 819, a second powered electrode 820, a first intermediate electrode 821, a second intermediate electrode 822, a first electrode gap 823, a second electrode gap 824, a third electrode gap 825, a distal cavitation bubble chamber plug 826, a rapid exchange (RX) guidewire tube 827, a rapid exchange (RX) guidewire lumen 828, a proximal exit 829 for rapid exchange guidewire lumen 828, a reinforcing element 830 at proximal guidewire lumen exit 829, and a jacket 818 covering or encasing tubular outer features such as the tube 816 rapid exchange guidewire tube 827 and reinforcing element 830. In this example, the features would be positioned near the distal end (not shown) of the medical device catheter 810 and catheter shaft 811, such as the distal end 713 shown with reference to FIG. 40 for medical device catheter 760. A distal exit (not shown) for the rapid exchange guidewire lumen 828 is also positioned at the distal end (not shown) of medical device catheter 810. A suitable example of such RX guidewire features is also shown and described with reference to FIGS. 17-21 describing a rapid exchange lumen 513 with a distal end 514 functioning as a distal exit for the guidewire, for example.

Figure 47:
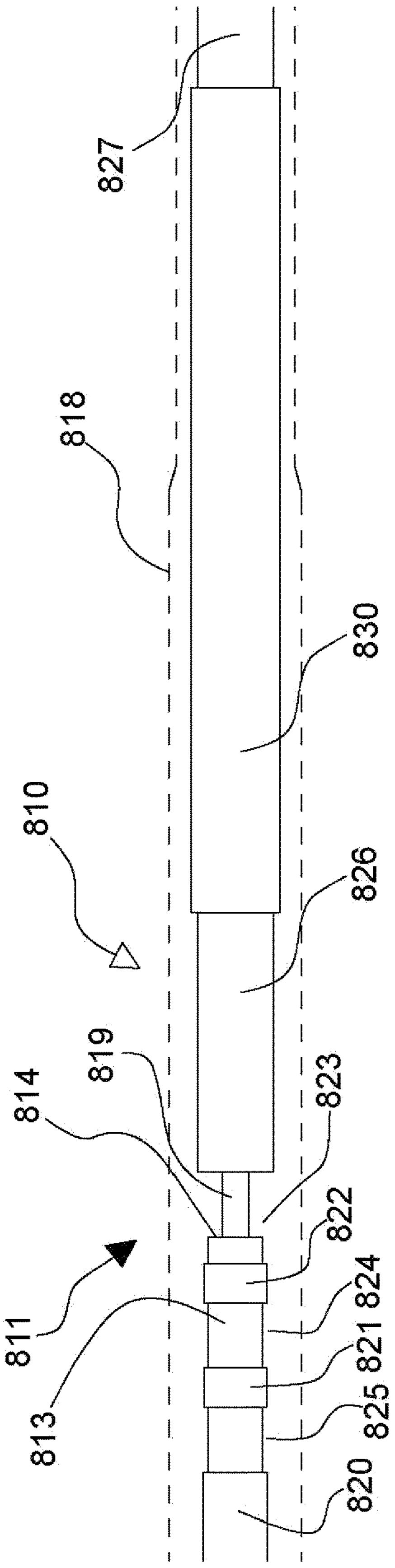
FIG. 47 is a partial schematic, longitudinal top view of a medical device catheter according to the present disclosure, showing the internal features and elements of a cavitation bubble chamber and proximal portion of a guidewire lumen of the medical device catheter.

FIG. 47 is a partial schematic longitudinal top view of the distal end of medical device catheter 810 and catheter shaft 811, with the outer jacket 818 hidden as dotted lines and tube 816 not shown such that the internal features of medical device catheter 810 and catheter shaft 811 and electrode configuration can be further illustrated. FIG. 47 can be conceptualized as a top view projection where, for reference, FIG. 46 is a side cross-sectional view projection. FIG. 47 illustrates the distal opening 814 of a first tube 813, a portion of first powered electrode 819, a portion of second powered electrode 820, a first intermediate electrode 821, a second intermediate electrode 822, a first electrode gap 823, a second electrode gap 824, a third electrode gap 825, a portion of distal plug 826, rapid exchange guidewire tube 827, and reinforcing element 830.

The example illustrated in FIG. 46 and FIG. 47 is a rapid exchange medical device catheter 810 capable of delivering electrohydraulic lithotripsy generated shockwaves to a target calcified artery in a manner like described with reference to medical device catheter 760 previously. Medical device catheter 810 also incorporates features similar to medical device catheter 760 including fitting assembly 715 which includes a first cavitation solution fitting 717, and a second cavitation solution fitting 718 that are connected to a first cavitation solution lumen or cavity 812 and a second cavitation solution lumen or cavity 817 which creates fluid flow paths, or connections, extending between the cavitation bubble chamber 815 and first and second cavitation solution fittings, 717 and 718. Fitting assembly 715 also includes an electrical connector 714 that includes at least two electrical connector pins, a first electrical connector pin 707 and a second electrical connector pin 708. Electrical connector 714 and the first and second electrical connector pins 707 and 708 respectively are adapted to electrically couple, or connect, a high voltage pulse generator to first powered electrode 819 and a second powered electrode 820 in the cavitation bubble chamber 815. The rapid exchange guidewire lumen 828 formed in part by rapid exchange guidewire tube 827 is similar to rapid exchange guidewire lumen 513 of rapid exchange (RX) intravascular lithotripsy (IVL) adapter 510 described previously.

One difference between the rapid exchange guide lumens of medical device catheter 810 and rapid exchange (RX) intravascular lithotripsy (IVL) adapter 510 is that as illustrated in FIGS. 17-20, a portion of rapid exchange guidewire lumen 513 is overlapping and parallel with the cavitation bubble chamber 520, where, as illustrated in FIG. 46 and FIG. 47, rapid exchange guidewire lumen 828 is distal to, and not overlapping with cavitation bubble chamber 815. Rapid exchange guidewire lumen 828 and cavitation bubble chamber 815 could be characterized as substantially co-linear with each other and the cavitation bubble chamber 815 is proximal to tube 827 forming the rapid exchange guidewire lumen 828. This configuration has advantages as the profile of non-overlapping configurations are smaller and lower profile for improved tracking through a tight stenotic arterial segment during a procedure. The rapid exchange guidewire lumen 828 has a proximal exit 829 through openings in the side wall of the RX guidewire tube 827, reinforcing element 830, and jacket 818 which covers the distal end of the catheter shaft 811. The jacket 818 also covers at least a portion of tube 816 forming cavitation bubble chamber 815 and at least a portion of second cavitation solution lumen 817. The opening in the side wall of the catheter shaft 811 forming proximal exit 829 may create a weak point where kinking may occur in use. As illustrated, the reinforcing element 830 is coaxial with a portion of the catheter shaft 811 and reinforces catheter shaft 811 in the region of the proximal exit 829 to minimize the likelihood of kinking during use. Reinforcing element 830 may be manufactured from a metal alloy, such as Stainless Steel or Nitinol, laser cut from a tube to form an opening in the sidewall in the region of the proximal exit 829.

The tube 816 forming cavitation bubble chamber 815 and at least a portion of second cavitation solution lumen 817 may be manufactured at a known diameter or size and is preferably not otherwise inflatable. In one aspect, tube 816 could be manufactured from a thermoset plastic, such as polyimide with a thin wall, on the order of about 0.001" to 0.003" in thickness. In other aspect, tube 816 could be manufactured from common thermoplastic catheter materials, such PEBAX or nylon, to create a sufficiently rigid tubular substrate necessary to form a cavitation bubble chamber 815. Tube 816 may also comprise a composite or laminated structure, including a combination of polymer substrates and braided or coiled metallic or polymer wire or fiber as further reinforcement.

Jacket 818 could comprise a polymer, such as PEBAX or nylon, and be manufactured to cover the distal end of the catheter shaft 811 using a thermal reflow process common in catheter manufacturing. The features of medical device catheter 810 could be incorporated into an adapter design similar to rapid exchange (RX) intravascular lithotripsy (IVL) adapter 510 described previously by further utilizing the tube 816 forming cavitation bubble chamber 815 and at least a portion of second cavitation solution lumen 817 as an elongated element or central tube, such as central tube 462 of attachment mechanism 467 of adapter 510.

FIG. 46 and FIG. 47 further illustrate a distal plug 826 which occludes the lumen of tube 816 to form a distal boundary 752 of the cavitation bubble chamber 815. Distal plug 826 also secures a distal end of the first powered electrode 819, which extends beyond the distal boundary 752 of cavitation bubble chamber 815. Further, in this configuration, the rapid exchange guidewire lumen 828 proximal exit 829 and associated features are positioned distal to the distal boundary 752 of cavitation bubble chamber 815, which may allow for a smaller overall profile of medical device catheter 810 in contrast with designs that require the guidewire lumen to extend through the cavitation bubble chamber 815 and associated electrodes and other IVL features. As illustrated, the first powered electrode 819 may comprise a round, long member like a wire or mandrel and does not require any insulated coating in the portion exposed to the cavitation bubble chamber 815 shown. A portion of first powered electrode 819 may be within and coaxial with the tube 813 forming a portion of the first cavitation solution lumen 812 and may extend distally from the distal opening 814 of the first cavitation solution lumen 812 formed by tube 813. The tube 813 forming at least a portion of the first cavitation solution lumen 812 may be comprised of an insulating material, such as polyimide or polyurethane to ensure first powered electrode is electrically isolated from the second powered electrode 820 and the first intermediate electrode 821 such that electrical arcing or sparking will only occur at the first electrode gap 823 between the first powered electrode 819 and second intermediate electrode 822. Further, the electrode spacing of the first intermediate electrode 821 and second powered electrode 820 are configured such that electrical arcing or sparking also occur at the electrode gap 824 and electrode gap 825 without requiring insulated coverings or coatings of the electrodes. Intermediate electrodes 821 and 822 are illustrated as rings or portions of a tube that are coaxial with and on the outer surface of tube 813 forming at least a portion of first cavitation solution lumen 812. Second powered electrode 820 is also illustrated as a ring or tube that is coaxial with and surrounding a portion of the outer surface of tube 813 forming at least a portion of first cavitation solution lumen 812, but could also be formed from a wire, a partial tube, a spring like coil, or a combination of features. The electrodes can be comprised of conductive materials such as stainless steel, copper, tungsten, platinum alloys, or nitinol as non-limiting examples.

Figure 48:
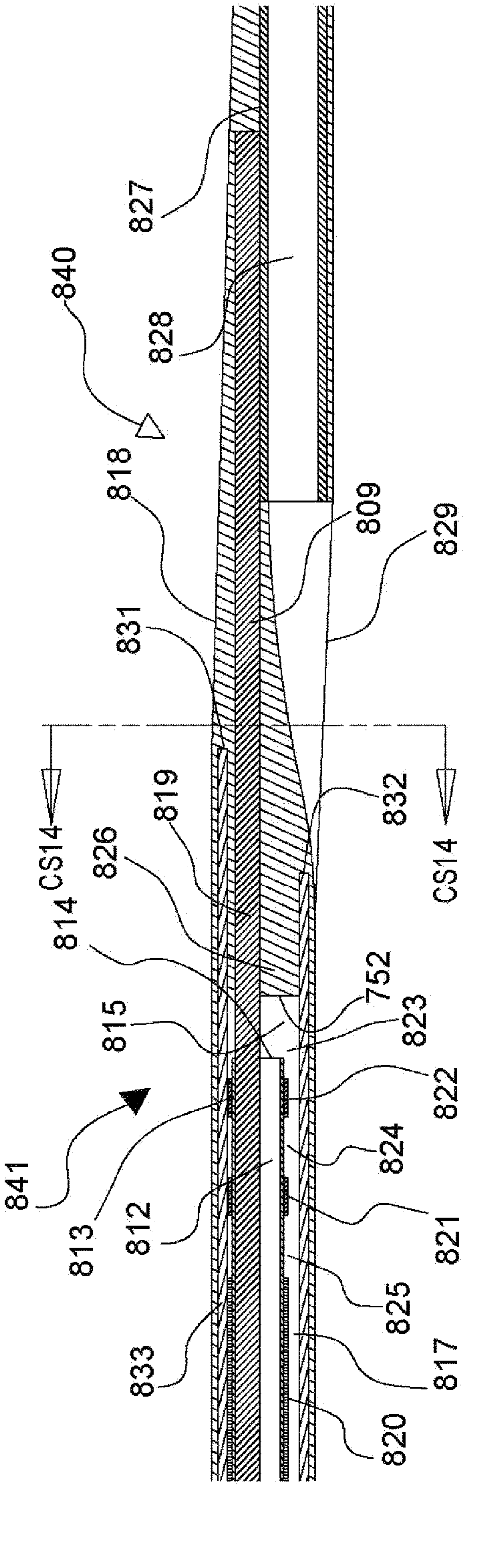
FIG. 48 is a partial schematic, longitudinal cross-sectional view of a cavitation bubble chamber and proximal portion of a guidewire lumen of a medical device catheter according to the present disclosure.

FIG. 48 is partial schematic, longitudinal cross-sectional view of a medical device catheter 840 according to an aspect of the present disclosure, showing a sectional view of a portion of medical device catheter 840 and catheter shaft 841, illustrating features of a cavitation bubble chamber 815, a first cavitation solution lumen 812, a first tube 813 forming first cavitation solution lumen 812, a distal opening 814 of first cavitation solution lumen 812, a second cavitation solution lumen 817, a tube 833 forming cavitation bubble chamber 815 having a distal boundary 752 and at least a portion of second cavitation solution lumen 817, a first powered electrode 819, a second powered electrode 820, a first intermediate electrode 821, a second intermediate electrode 822, a first electrode gap 823, a second electrode gap 824, a third electrode gap 825, a distal cavitation bubble chamber plug 826, a rapid exchange (RX) guidewire tube 827, a rapid exchange (RX) guidewire lumen 828, a proximal exit 829 for rapid exchange guidewire lumen 828, and a jacket 818 covering or encasing tubular outer features such as the tube 833, rapid exchange guidewire tube 827 and at least a portion of a first powered electrode 819. Tube 833 may be manufactured such that the top distal edge 831 extends distally with respect to the bottom proximal edge 832. This feature could be manufactured by cutting the end of tube 833 at an angle such that proximal edge 832 is proximal to distal edge 831. Alternatively, tube 833 could be notched, cut, or machined such that the top distal edge 831 could extend distally beyond edge 832. In this example, the features may be positioned near the distal end (not shown) of a medical device catheter 840 and catheter shaft 841, such as the distal end 713 shown with reference to FIG. 40 for medical device catheter 760. A distal exit (not shown) for the rapid exchange guidewire lumen 828 is also present at the distal end (not shown) of medical device catheter 840. A suitable example of such RX guidewire features is also shown and described with reference to FIGS. 17-21 describing a rapid exchange lumen 513 with a distal end 514 functioning as a distal exit for the guidewire, for example.

Figure 49:
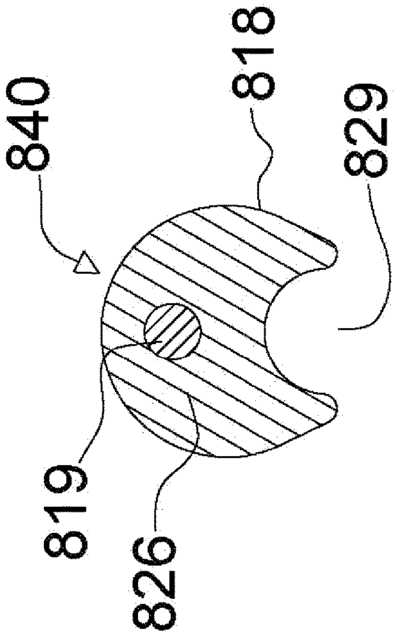
FIG. 49 is a partial schematic, transverse cross-sectional view CS14 of the medical device catheter of FIG. 48.

FIG. 49 is a partial schematic, transverse cross-sectional view of medical device catheter 840 through a portion of catheter shaft 841 in the location of a proximal exit 829 for rapid exchange guidewire lumen 828, distal to the cavitation bubble chamber 815 distal boundary 752 and tube 833 forming cavitation bubble chamber 815, or CS14 as illustrated in FIG. 48, and showing a first powered electrode 819, a portion of distal cavitation bubble chamber plug 826, and a jacket 818 (which also functions to cover or encase tubular outer features such as the tube 833, rapid exchange guidewire tube 827 and at least a portion of a first powered electrode 819 shown in FIG. 48).

The example illustrated in FIG. 48 and FIG. 49 is a rapid exchange medical device catheter 840 capable of delivering electrohydraulic lithotripsy generated shockwaves to a target calcified artery in a manner like described with reference to medical device catheter 760 previously, with features similar to medical device catheter 810, including tube 827 forming rapid exchange guidewire lumen 828 distal to the cavitation bubble chamber 815. However, medical device catheter 840 incorporates a rapid exchange lumen 828 that is not substantially co-linear with the cavitation bubble chamber 815, or tube 833 forming a cavitation bubble chamber 815 and at least a portion of second cavitation solution lumen 817.

Distal plug 826 also secures a distal end 809 of the first powered electrode 819, which extends beyond the distal boundary 752 of cavitation bubble chamber 815. In this configuration, the rapid exchange guidewire lumen 828 proximal exit 829 and associated features are positioned distal to the distal boundary 752 of cavitation bubble chamber 815, which may allow for a smaller overall profile of medical device catheter 810 in contrast with designs that require the guidewire lumen to extend through the cavitation bubble chamber 815 and associated electrodes and other IVL features. To further enable a smaller profile, as illustrated, rapid exchange lumen 828 and cavitation bubble chamber 815 are still substantially parallel, but with an offset axis to accommodate an overlapping portion of first powered electrode 819 with rapid exchange lumen 828 formed by tube 827. By overlapping in this manner, the first powered electrode spans the portion of the catheter shaft 841 at the proximal exit 829 for rapid exchange guidewire lumen 828. Spanning proximal exit 829 in this manner enables the first powered electrode 819 to act as a reinforcing element in this region which would otherwise be potentially weakened or introduce a kinking risk due to the opening of proximal exit 829. If the first powered electrode 819 is manufactured from stainless steel or Nitinol, for example, it could serve as both an electrically conductive electrode and a reinforcing feature, though other conductors having sufficient strength characteristics may be suitable, including but not limited to tungsten and tungsten alloys and nickel and nickel alloys.

As further illustrated in FIG. 48, tube 833 may be manufactured such that the top distal edge 831 extends distally with respect to the bottom proximal edge 832. This feature could be manufactured by cutting the end of tube 833 at an angle such that edge 832 is proximal to edge 831. Alternatively, tube 833 could be notched, cut, or machined such that the top edge 831 could extend distally beyond edge 832.

FIGS. 48 and 49 further illustrate how in this configuration, the distal cavitation bubble chamber plug 826 and jacket 818 could be manufactured to merge into a single polymer body at portions of the catheter shaft 841. This merging could be accomplished through a re-flow heating process where the two polymer components are fixtured together in the desired position and heated until both are melted such that they flow together into a single component or body.

FIG. 49 also illustrates the first powered electrode 819 with a round cross-section but could also have a rectangular, oblong, square or other geometric cross-section as desired, for example, to reduce the overall profile of the catheter shaft 841. FIG. 48 also illustrates how biasing or positioning the first powered electrode 819 to one side of the cavitation bubble chamber 815 enables lowering the overall profile or transverse cross-sectional size of the catheter shaft 841. Second powered electrode 820, tube 813 forming first cavitation solution lumen 812, and intermediate electrodes 821 and 822 may also likewise be biased to one side as shown to achieve the lower overall profile of catheter shaft 841.

Figure 50:
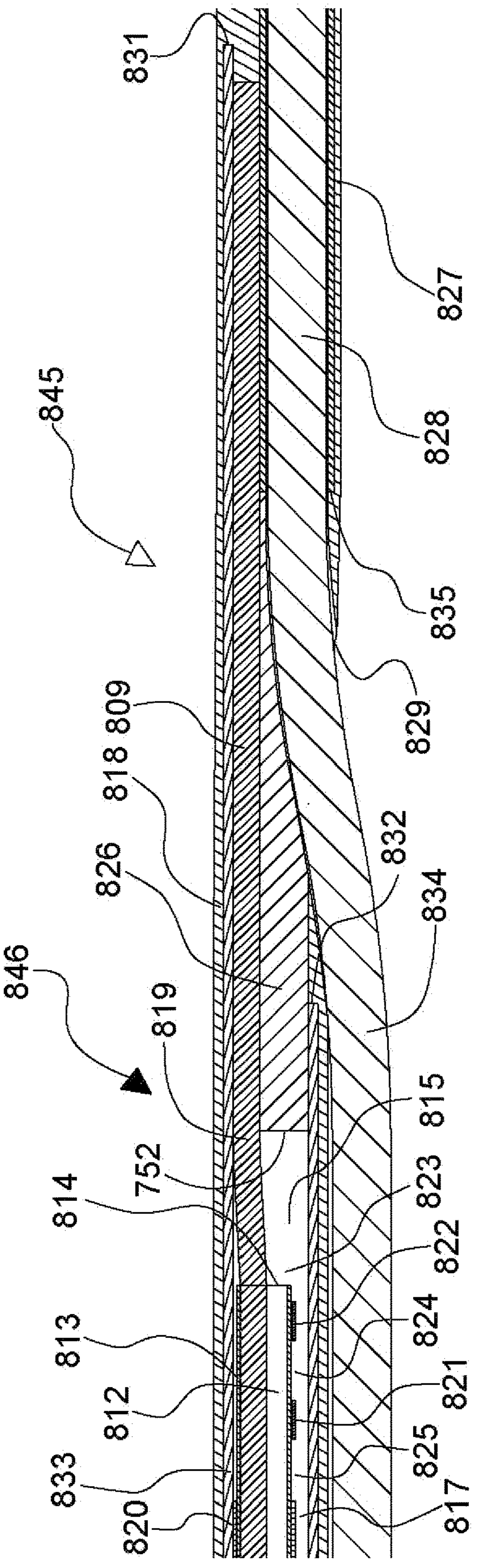
FIG. 50 is a partial schematic, longitudinal cross-sectional view of a cavitation bubble chamber and proximal portion of a guidewire lumen of a medical device catheter according to the present disclosure.

FIG. 50 is partial schematic, longitudinal cross-sectional view of a medical device catheter 845 according to an aspect of the present disclosure, showing a sectional view of a portion of medical device catheter 845 and catheter shaft 846, illustrating features of a cavitation bubble chamber 815 having distal boundary 752, a first cavitation solution lumen 812, a first tube 813 forming first cavitation solution lumen 812, a distal opening 814 of first cavitation solution lumen 812, a second cavitation solution lumen 817, a tube 833 forming cavitation bubble chamber 815 and at least a portion of second cavitation solution lumen 817, a first powered electrode 819, a second powered electrode 820, a first intermediate electrode 821, a second intermediate electrode 822, a first electrode gap 823, a second electrode gap 824, a third electrode gap 825, a distal cavitation bubble chamber plug 826, a rapid exchange (RX) guidewire tube 827, a rapid exchange (RX) guidewire lumen 828 (shown occupied by guidewire 834), a proximal exit 829 for rapid exchange guidewire lumen 828, and a jacket 818 covering or encasing tubular outer features such as the tube 833, rapid exchange guidewire tube 827 having a proximal end 835 and at least a portion of a first powered electrode 819.

FIG. 50 also illustrates the top edge 831 of tube 833 that extends distally beyond bottom edge 832, such that edge 832 of tube 833 is proximal to the edge 831 of tube 833. Also illustrated are guidewire 834 passing through rapid exchange (RX) guidewire lumen 828 of rapid exchange guidewire tube 827. The features may be positioned near the distal end (not shown) of a medical device catheter 845 and catheter shaft 846, such as the distal end 713 shown with reference to FIG. 40 for medical device catheter 760. A distal exit (not shown) for the rapid exchange guidewire lumen 828 is also present at the distal end (not shown) of medical device catheter 845. A suitable example of such RX guidewire features is also shown and described with reference to FIGS. 17-21 describing a rapid exchange lumen 513 with a distal end 514 functioning as a distal exit for the guidewire, for example.

FIG. 50 illustrates another suitable configuration where both the first powered electrode 819, and a portion of tube 833 forming cavitation bubble chamber 815 overlap rapid exchange guidewire tube 827 in a portion distal to the proximal guidewire exit 829, and proximal end 835 of rapid exchange guidewire tube 827. This can be conceptualized where in this overlapped region, the first powered electrode 819 is positioned or located between a portion of the inside surface of tube 833 and a portion of the outside surface of rapid exchange guidewire tube 827. As illustrated, in this region, the tube 833 has been cut, notched, or otherwise manufactured with an edge 831 that extends distally past the distal end 809 of first powered electrode 819, such that tube 833 also has an edge 832 that is proximal to the proximal edge 835 of rapid exchange guidewire tube 827 and proximal guidewire exit 829. Overlapping a portion of the tube 833, first powered electrode 819 and rapid exchange guidewire tube 827 in the region between the proximal end 835 of the rapid exchange guidewire tube 827 and edge 832 of tube 833 where a proximal guidewire exit 829 is formed, provides extra structural support in this region while maintaining a low transfer cross-sectional profile. As described previously, further adding to the low or smaller profile is the configuration of the cavitation bubble chamber 815 and associated electrodes and IVL features being positioned proximal to the separate guidewire lumen 828 and proximal exit 829, such that the guidewire 834 and lumen do not have to pass through those IVL features. It can be appreciated that as shown, rapid exchange guidewire lumen 828 is formed by a tube 827, but as an alternate example, the lumen 828 could be formed by the jacket or polymer body 818 of the catheter shaft 851 in that portion, without the need for a separate tube.

FIG. 50 further illustrates distal cavitation bubble chamber plug 826 as a distinct feature that does not necessarily merge with jacket 818 covering or encasing tubular outer features such as the tube 833 and rapid exchange guidewire tube 827. Distal cavitation bubble chamber plug 826 seals a distal portion of tube 833 and encapsulates and secures a portion of first powered electrode 819, as well as defines the distal boundary 752 of cavitation bubble chamber 815, keeping it proximal to guidewire proximal exit 829 as described. Further, distal cavitation bubble chamber plug 826 biases first powered electrode 819 in an off-axis position with respect to the axis of cavitation bubble chamber 815 such that at least a portion of the first powered electrode 819 axis is not coaxial with cavitation bubble chamber 815. Likewise, first cavitation solution tube 813 and first cavitation solution lumen 813 are biased to be positioned off axis with respect to the cavitation bubble chamber 815 axis.

FIG. 50 further illustrates first and second intermediate electrodes 821 and 822 as rings or portions of a tube that do not form a complete circle. For example, the first and second intermediate electrodes 821 and 822 may be semi-circular cylinders having a transverse cross-sectional arc of 180 degrees, or more preferably, an arc of more than 180 degrees but less than 360. This configuration would bias the arcing to the bottom side of the cavitation bubble chamber 815 as illustrated.

Figure 51A:
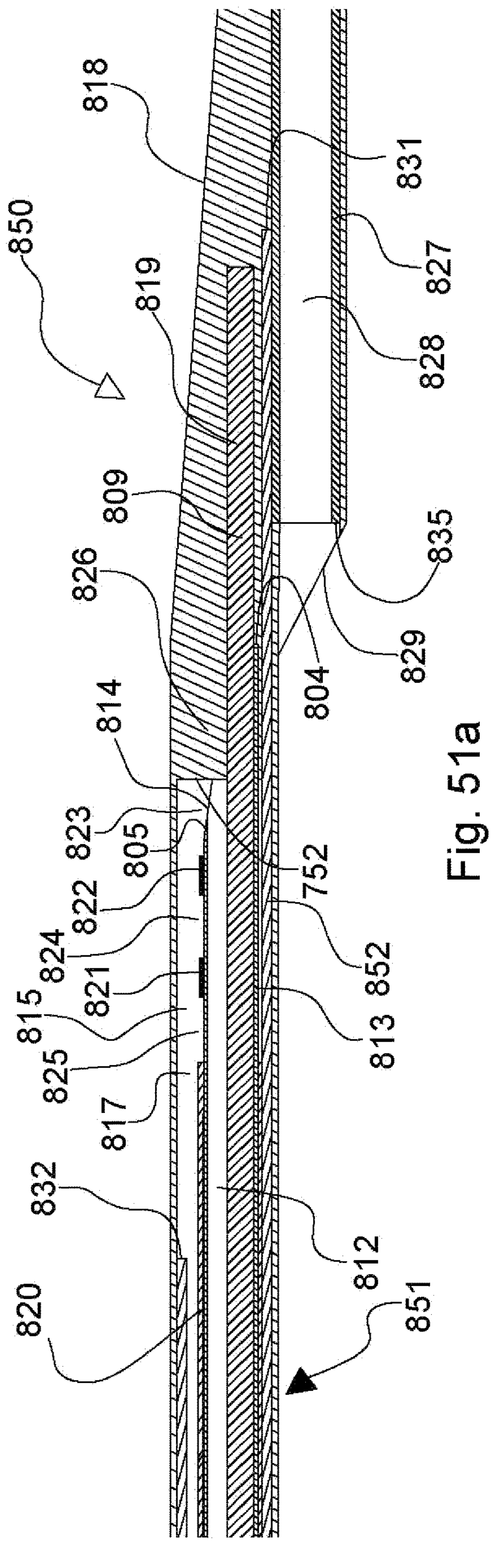
FIG. 51*a* is a partial schematic, longitudinal cross-sectional view of a cavitation bubble chamber and proximal portion of a guidewire lumen of a medical device catheter according to the present disclosure.
Figure 51B:
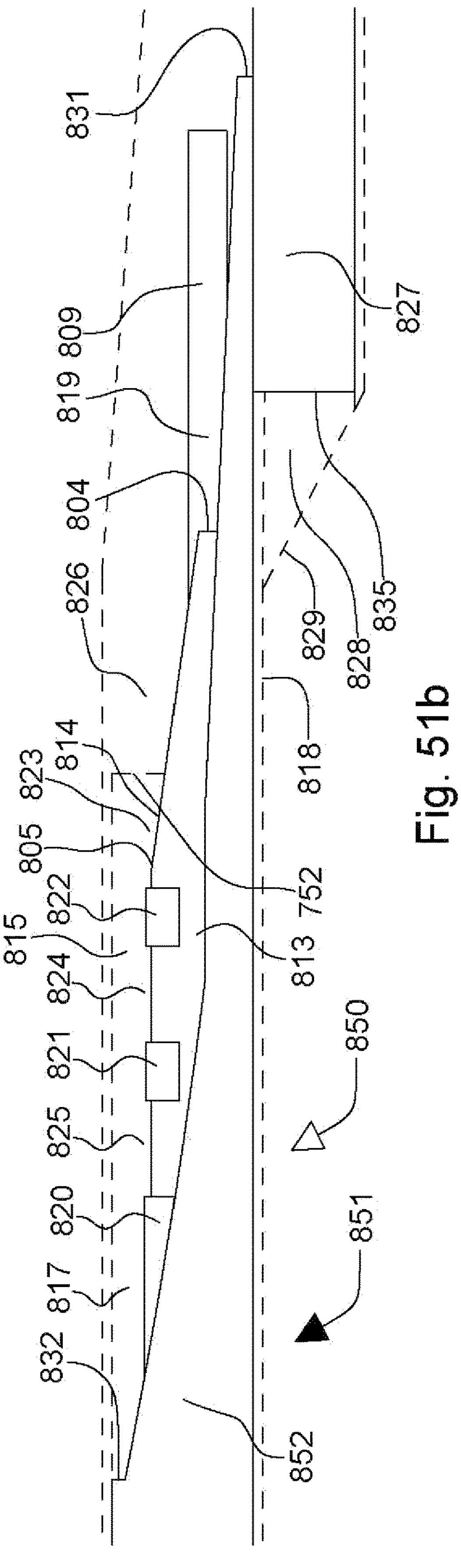
FIG. 51*b* is a partial schematic, longitudinal side view of a cavitation bubble chamber and proximal portion of a guidewire lumen of a medical device catheter according to the present disclosure, showing internal features and elements of the medical device catheter.

FIG. 51*a* is partial schematic, longitudinal cross-sectional view of a medical device catheter 850 according to an aspect of the present disclosure, showing a sectional view of a portion of medical device catheter 850 and catheter shaft 851, and FIG. 51*b* is partial schematic, longitudinal view of a medical device catheter 850 according to an aspect of the present disclosure, showing a longitudinal view of a portion of medical device catheter 850 and catheter shaft 851 with outer polymer jacket shown as hidden dotted lines. FIGS. 51*a* and 51*b* illustrate features of a cavitation bubble chamber 815 (also partially hidden with dotted lines in FIG. 51*b*) having distal boundary 752, a first tube 813 forming first cavitation solution lumen 812 (not shown in FIG. 51*b*, but illustrated in FIG. 51*a*), a distal opening 814 of first cavitation solution lumen 812, a second cavitation solution lumen 817, a tube 852 forming a portion of cavitation bubble chamber 815 and at least a portion of second cavitation solution lumen 817, a first powered electrode 819, a second powered electrode 820, a first intermediate electrode 821, a second intermediate electrode 822, a first electrode gap 823, a second electrode gap 824, a third electrode gap 825, a distal cavitation bubble chamber plug 826, a rapid exchange (RX) guidewire tube 827, a rapid exchange (RX) guidewire lumen 828, a proximal exit 829 for rapid exchange guidewire lumen 828, and a jacket 818 (illustrated with hidden lines to show internal features) covering or encasing tubular outer features such as the tube 852, rapid exchange guidewire tube 827 having a proximal end 835 and at least a portion of a first powered electrode 819. FIG. 51*a* and FIG. 51*b* also illustrate the bottom distal edge 831 of tube 852 that extends distally beyond top proximal edge 832, such that edge 832 of tube 852 is proximal to the edge 831 of tube 852, electrode gap 825 and cavitation bubble chamber 815, likewise, first tube 813 forming at least a portion of a first cavitation solution lumen 812 includes a top proximal edge 805 at the distal opening 814 of a first cavitation solution lumen 812 and a bottom distal edge 804 which extends distally past the distal boundary 752 of cavitation bubble chamber 815. These features may be positioned near the distal end (not shown) of medical device catheter 850 and catheter shaft 851, such as the distal end 713 shown with reference to FIG. 40 for medical device catheter 760. A distal exit (not shown) for the rapid exchange guidewire lumen 828 is also at the distal end (not shown) of medical device catheter 850. A suitable example of such RX guidewire features is also shown and described with reference to FIGS. 17-21 describing a rapid exchange lumen 513 with a distal end 514 functioning as a distal exit for the guidewire, for example.

FIGS. 51*a* and 51*b* illustrate another suitable configuration where both the first powered electrode 819, and a portion of tube 852 forming a bottom portion of cavitation bubble chamber 815 overlap rapid exchange guidewire tube 827 in a portion distal to the proximal guidewire exit 829 and proximal end 835 of rapid exchange guidewire tube 827. This can be conceptualized where in this overlapped region, the first powered electrode 819 is positioned or located next to a portion of the inside surface of tube 852 and a portion of the outside surface of rapid exchange guidewire tube 827 is positioned next to or adjacent the outside surface of tube 852. This can be further conceptualized as the first powered electrode 819, a portion of tube 852, and a portion of rapid exchange guidewire tube 827 form a structure where a portion of the tube 852 is disposed between a portion of the first powered electrode 819 and a portion of the rapid exchange guidewire tube 827. As illustrated, in this region, the tube 852 has been cut, notched, or otherwise manufactured with an edge 831 that extends distally past the distal end 809 of first powered electrode 819, such that tube 852 also has an edge 832 that is proximal to third electrode gap 825. As illustrated, cavitation bubble chamber 815 is formed by a portion of tube 852 and outer jacket 818. Overlapping a portion of first powered electrode 819, a portion the tube 852, and rapid exchange guidewire tube 827 in the region between the proximal end 835 of the rapid exchange guidewire tube 827 is formed, provides extra structural support in this region and further enables the smaller overall profile of medical device catheter 850. An advantage of this configuration is that the proximal guidewire exit 829 and guidewire tube 827 takes a path that is generally parallel with the tube 852 and catheter shaft 851 such that a guidewire would not need to bend significantly at the proximal guidewire exit 852 in use. This contrasts with the path of guidewire 834 illustrated in FIG. 50 that requires an "S" bend as it exits the proximal guidewire exit 829.

FIGS. 51*a* and 51*b* also illustrate biasing the first powered electrode 819 to a side of the cavitation bubble chamber 815 closer to the rapid exchange guidewire tube 827, such that the axis of the first powered electrode 819 is not coaxial relative to the cavitation bubble chamber 815 but rather first powered electrode 819 is biased to have an axis, a portion of which is biased off-axis or biased away from the axis of the cavitation bubble chamber 815. Second powered electrode 820, tube 813 forming first a cavitation solution lumen 812, and intermediate electrodes 821 and 822 are also likewise biased to one side as shown. It can be appreciated that as shown, rapid exchange guidewire lumen 828 is formed in part by jacket 818 and tube 827, but as an alternate example, the lumen 828 could be formed by the jacket or polymer body 818 of the catheter shaft 851 in that portion, without the need for a separate tube. In this example, the first powered electrode 819 and portion of tube 852 would overlap the lumen 828 in a region just distal to the proximal guidewire exit 829, to reinforce the region of the catheter shaft 851 just proximal to the proximal guidewire exit 829. Further, in this example, a portion of the outer surface of tube 852 in the overlap region could form a portion of the wall of lumen 828.

FIGS. 51*a* and 51*b* further illustrate the portion of the distal opening 814 of first cavitation solution lumen 812 proximal to the distal boundary 752 of cavitation bubble chamber 815 provides a fluid communication path between the first cavitation solution lumen 812, the cavitation bubble chamber 815, and the second cavitation solution lumen 817.

FIGS. 51*a* and 51*b* further illustrate first and second intermediate electrodes 821 and 822 as rings or portions of a tube that do not form a complete circle. For example, the first and second intermediate electrodes 821 and 822 may be half cylinders, having a transverse cross-sectional arc of 180 degrees. This configuration would bias the arcing to the top side of the cavitation bubble chamber 815 as illustrated. Further, it may be appreciated that first powered electrode 819 does not require any insulative coating in the region of the cavitation bubble chamber 815 or in the first cavitation solution lumen 812 because first cavitation solution tube 813 functions as an electrical barrier separating first powered electrode 819 from the intermediate 821, 822 and second powered electrodes 820.

FIGS. 51*a* and 51*b* also illustrates first cavitation solution tube 813 has been cut, notched, or otherwise manufactured with a distal edge 804 that extends distally past the distal boundary 752 of the cavitation bubble chamber 815 and a proximal edge 805 at the distal opening 814 of first cavitation solution lumen 812. As illustrated, distal edge 804 of first cavitation solution tube 813 is secured to and oriented relative to first powered electrode by way of the distal plug 826. This configuration ensures the desired orientation of the intermediate electrodes 821 and 822 relative to the first powered electrode 819, including to bias the spark gap 823 to occur between the top of the first powered electrode 819 as illustrated and the nearest intermediate electrode 822 where there is more cavitation solution volume present.

Figure 52:
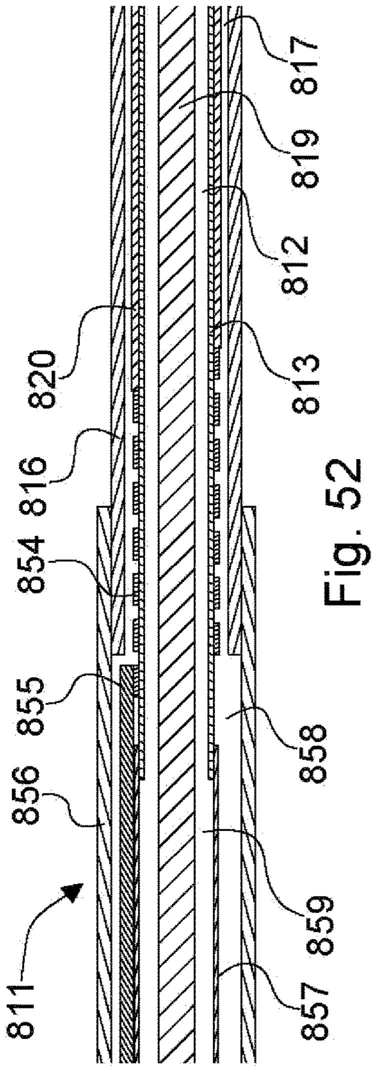
FIG. 52 is a partial schematic, longitudinal cross-sectional view of a medical device catheter according to the present disclosure.

FIG. 52 is partial schematic, longitudinal cross-sectional view of a portion of catheter shaft 811 showing the internal features at a section proximal to a cavitation bubble chamber. FIG. 52 illustrates first powered electrode 819, second powered electrode 820, tube 813 forming a portion of first cavitation solution lumen 812, tube 816 forming a portion of second cavitation solution lumen 817, an intermediate second powered electrical conductor 854 formed in a coil or spiral and coaxial with tube 813 and electrically connected or coupled to second powered electrode 820, a proximal second powered electrical conductor 855 electrically connected or coupled to an intermediate second electrical conductor 854, a proximal first cavitation solution lumen tube 857 forming a proximal first cavitation solution lumen 859 fluidly connected to first cavitation solution lumen 812, and a proximal second cavitation solution lumen tube 856 forming a proximal second cavitation solution lumen 858 fluidly connected to second cavitation solution lumen 817. Any jacket or outer polymer body, such as jacket 818 shown in previous Figures, is not illustrated for clarity.

FIG. 52 illustrates a transition at a position proximal to the cavitation bubble chamber, for example cavitation bubble chamber 815 in the catheter shaft 811 shown and described with reference to previous Figures and embodiments, where the effective size of the first cavitation solution lumen 812 and the second cavitation solution lumen 817 are increased to increase the net capacity for cavitation solution fluid flow. The effective annular space or lumen size at lumens 858 and 859 are larger than the effective annular space or lumen size at lumens 817 and 812 respectively. As illustrated tube 856 is coaxial and overlaps with tube 816 and is coupled together, either through an adhesive bonding operation or a polymer jacket reflowed over both, creating a contiguous structure. Similarly, tube 857 is coaxial and overlaps with tube 813. Also illustrated is an electrical continuity configuration of a second powered electrode circuit which includes the second powered electrode 820 beginning at the proximal end of the cavitation bubble chamber 815, transitioning to an intermediate second powered electrical conductor 854 and further transitioning to a proximal second powered electrical conductor 855. A proximal end of second powered electrode 820 may be welded, soldered, brazed or otherwise electrically connected to a distal end of electrical conductor 854 where the proximal end of electrical conductor 854 may also be welded, soldered, brazed or otherwise electrically connected to a distal end of electrical conductor 855. Electrical conductor 854 is illustrated as a coil or spiral coaxial with tube 813. This coil configuration would create a more flexible catheter shaft 811 structure but still maintain the necessary electrical continuity. If space permitted, the electrical conductor 854 may comprise a straight electrically conductive wire, for example a flat wire of copper or stainless steel. An alternative configuration may comprise a contiguous electrically conductive wire, for example a flat wire of copper or stainless steel, spanning the entire length necessary for second powered electrode 820, intermediate electrical conductor 854 a portion of proximal electrical conductor 855.

Figure 53:
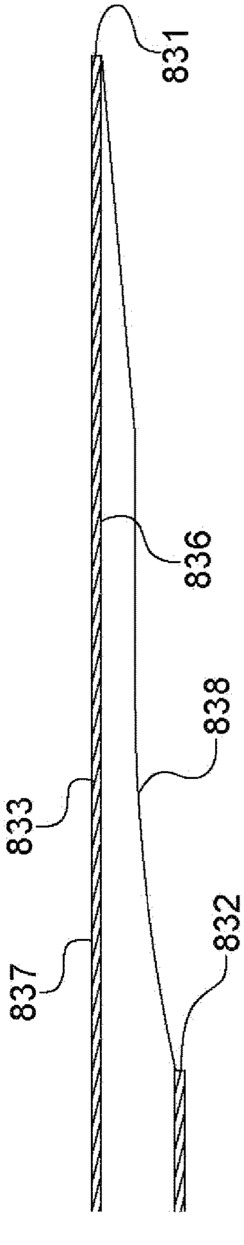
FIG. 53 is a partial schematic, longitudinal cross-sectional view of a tube forming a portion of a cavitation bubble chamber of a medical device catheter according to the present disclosure.

FIG. 53 is partial schematic, longitudinal cross-sectional view of a tube 833 suitable for use in the medical device catheter 845 configuration shown and described with reference to FIG. for example, and forming cavitation bubble chamber 815 (not shown) and at least a portion of second cavitation solution lumen 817 (not shown) according to an aspect of the present disclosure. FIG. 53 illustrates a notch or cut 838 formed or created at the distal end of tube 833 forming a distal edge 831 at the top of the tube 833 and a proximal edge 832 at the bottom of the tube 833. FIG. 53 further illustrates tube 833 has an inside or inner surface 836 and an outside or outer surface 837. It is appreciated that if tube 833 as illustrated in FIG. 53 were mirrored about a longitudinal axis, the distal edge 831 would be on the bottom and proximal edge 832 would be on the top, thus making it suitable for use as tube 852 such as illustrated and descried with reference to FIG. 51, for example.

Figure 54:
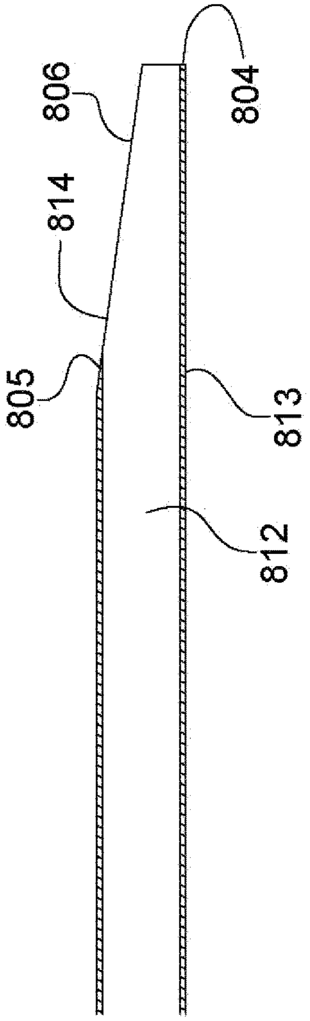
FIG. 54 is a partial schematic, longitudinal cross-sectional view of a tube forming a first cavitation solution lumen of a medical device catheter according to the present disclosure.

FIG. 54 is partial schematic, longitudinal cross-sectional view of a tube 813 suitable for use in the medical device catheter 850 configuration shown and described with reference to FIGS. 51*a* and 51*b*, for example, and forming a first cavitation solution lumen 812 having a distal opening 814 according to another aspect of the present disclosure. FIG. 54 illustrates a notch or cut 806 formed or created at the distal end of tube 813 forming a distal edge 804 at the bottom of the tube 813 extending beyond a proximal edge 805 at the top of the tube 813 around distal opening 814.

In the embodiments of FIGS. 46-54, cavitation solution may be circulated by means of pressurizing first cavitation solution lumen 812 at the first cavitation solution fitting 717 at the proximal end 719 with a syringe filled with fresh cavitation solution and applying suction at the second cavitation solution fitting 718 to help evacuate the cavitation solution in the cavitation bubble chamber 815 by way of the second cavitation solution lumen 817. A syringe or similar vacuum generating device can be attached to accomplish the suction. Sufficient cavitation solution circulation may be accomplished by simultaneously pressurizing first cavitation solution fitting 717 and suctioning at second cavitation solution fitting 718 as well as pressurizing solely or suctioning solely provided there is a sufficient reservoir of cavitation solution connected to the first cavitation solution fitting 717.

In the example electrode configurations illustrated in FIG. 44 to FIG. 51, the electrodes could be fixed or positioned using an appropriate adhesive or a polymer by way of a re-flow heating process. Additionally, tubes 816, 833, and 852 that form the cavitation bubble chamber 815 may comprise a round or non-round cross-section, and manufactured from a suitable polymer such as polyimide, PEBAX, or Nylon as non-limiting examples.

It may be appreciated that any of the IVL adapter structures, elements, configurations, features, or functions disclosed and discussed previously with respect to FIGS. 1-28 may likewise be incorporated or utilized in a unitary or "one-piece" catheter design, including and beyond those explicitly discussed with reference to FIGS. 29-54. In other words, the embodiments described with reference to FIGS. 29-54 are non-limiting examples of how IVL features and functionality may be incorporated into such unitary catheter designs. Likewise, the embodiments described with reference to FIGS. 29-54 may also be incorporated into a modular catheter system such as described previously, and not limited to the specific examples discussed with reference to FIGS. 1-28. It may also be appreciated that any common or shared elements, functions or features of any particular embodiment or aspect described with reference to FIGS. 1-54 may likewise be used and are enabled for use in combination or conjunction with any of the other embodiments or aspects described herein, and that some shared elements may not share the same reference numeral or designation but may nonetheless be the same, similar or functional equivalent and be likewise enabled for the same or similar uses.

A potential advantage of the unitary design embodiments of the present disclosure is that they may be constructed to have a smaller profile, thereby enabling the medical device catheter to be used for certain procedures that the modular system may not be suitable for depending on location of the therapy and patient vasculature considerations.

Furthermore, with respect to any of the embodiments described above with reference to FIGS. 1-54, other alternatives may be appreciated for certain structures, configurations and functions of the medical device catheter modular system or unitary design. For example, other suitable electrode set configurations include end-to-end and parallel electrode configurations, or electrode configurations that include combinations of end-to-end and parallel electrodes. This may include, for example, an end of an electrode positioned or configured to create an electrode gap with a parallel electrode. The electrodes could be formed from wire, tubing, formed or cut conductive materials, sheet metal, or many other materials and forms. For example, one or more of the electrodes could include one or more "teeth like" features, "pointy" features, sharpened features, laser cut features, shaped features, or screw thread type features, along the length or at the ends that could concentrate the current density for targeted or optimized electric arcing.

Further it may be appreciated by those skilled in the art that any appropriate electrode gap or spacing between electrodes may be configured to generate a sufficient arc, shockwave and cavitation bubbles for lithotripsy procedures, and is not limited to between about 100 to about 500 microns. The relative surface areas (including their ratios) and geometries of electrodes may also be configured to generate sufficient arcs, shockwaves and cavitation bubbles.

Calcium rich lesions within the vasculature is an issue affecting the cardiovascular health of many people. Lithotripsy, specifically the use of shockwaves to disrupt calcium, can be an effective method to modify vascular calcium structures and improve outcomes during angioplasty procedures. According to the present disclosure, a novel modular catheter system and adapter are provided, as well as a unitary design option, to enable lithotripsy procedures to be performed more effectively and flexibly by a physician.

While the invention has been described with reference to an exemplary embodiment(s), it will be understood by those skilled in the art that various changes may be made and equivalents may be substituted for elements thereof without departing from the scope of the invention. In addition, modifications may be made to adapt a particular situation or material to the teachings of the invention without departing from the essential scope thereof. Therefore, it is intended that the invention is not limited to the particular embodiment(s) disclosed, but that the invention will include all embodiments falling within the scope of the appended claims.

The invention claimed is:

1. A medical device catheter, comprising:

a first tube comprising a first cavitation solution lumen having a distal opening, a second tube housing the first tube, and comprising a cavitation bubble chamber, a second cavitation solution lumen in fluid communication with the first cavitation solution lumen through the distal opening, and a distal plug at a distal end of the cavitation bubble chamber to create a distal boundary of the cavitation bubble chamber;

a proximal rapid exchange guidewire exit positioned distal to the distal boundary of the cavitation bubble chamber and in communication with a guidewire lumen; and a first powered electrode extending through the first tube and the first cavitation solution lumen and cavitation bubble chamber and into the distal plug beyond the distal boundary of the cavitation bubble chamber.

2. The medical device catheter of claim 1, wherein a portion of the second tube overlaps a portion of the guidewire lumen.

3. The medical device catheter of claim 2, wherein a distal end of the second tube comprises a distal edge that extends beyond a proximal edge of the second tube and the distal edge overlaps the portion of the guidewire lumen.

4. The medical device catheter of claim 1, wherein the first powered electrode overlaps a portion of the guidewire lumen.

5. The medical device catheter of claim 1, wherein the distal opening of the first cavitation solution lumen is proximal to the distal boundary of the cavitation bubble chamber.

6. The medical device catheter of claim 1, wherein at least a portion of the second cavitation solution lumen is disposed around the outside of the first tube.

7. The medical device catheter of claim 6, wherein at least a portion of the second tube forms the cavitation bubble chamber and at least a portion of the second cavitation solution lumen.

8. The medical device catheter of claim 1, wherein a distal end of the first tube comprises a distal edge that extends beyond a proximal edge of the tube.

9. The medical device catheter of claim 1, wherein the first tube is biased off-axis relative to the second tube.

10. The medical device catheter of claim 1, wherein the first powered electrode is biased off-axis relative to the first tube or the second tube.

11. The medical device catheter of claim 1, wherein a portion of the second tube is disposed between a portion of the first powered electrode and a portion of the guidewire lumen.

12. The medical device catheter of claim 1, wherein a portion of the first powered electrode is disposed between a portion of the second tube and a portion of the guidewire lumen.

13. The medical device catheter of claim 1, further comprising a second powered electrode disposed outside of the first tube.

14. The medical device catheter of claim 13, further comprising at least one intermediate electrode disposed outside of the first tube to create a first electrode gap between the at least one intermediate electrode and the first powered electrode, and a second electrode gap between the at least one intermediate electrode and the second powered electrode.

15. The medical device catheter of claim 14, wherein the at least one intermediate electrode comprises a semi-circular cylinder.

16. The medical device catheter of claim 15, wherein the at least one intermediate electrode is coaxial with the first cavitation solution lumen.

17. The medical device catheter of claim 1, wherein the first powered electrode does not comprise an insulative coating in the region of the cavitation bubble chamber.

18. The medical device catheter of claim 1, further comprising a polymer jacket forming at least a portion of the second tube and the cavitation bubble chamber.

19. The medical device catheter of claim 1, further comprising an inflatable balloon proximal to the cavitation bubble chamber.

20. The medical device catheter of claim 1, wherein a portion of the guidewire lumen comprises a third tube.

* * * * *